US011866702B2

(12) United States Patent
Klein et al.

(10) Patent No.: US 11,866,702 B2
(45) Date of Patent: Jan. 9, 2024

(54) NUCLEIC ACID MOLECULES FOR PSEUDOURIDYLATION

(71) Applicants: University of Rochester, Rochester, NY (US); ProQR Therapeutics II B.V., Leiden (NL)

(72) Inventors: Bart Klein, Leiden (NL); Janne Juha Turunen, Leiden (NL); Lenka Van Sint Fiet, Leiden (NL); Pedro Duarte Morais Fernandes Arantes Da Silva, Leiden (NL); Julien Auguste Germain Boudet, Leiden (NL); Yi-Tao Yu, Pittsford, NY (US); Hironori Adachi, Rochester, NY (US); Meemanage De Zoysa, Rochester, NY (US)

(73) Assignees: University of Rochester, Rochester, NY (US); ProQR Therapeutics II B.V., Leiden (NL)

( * ) Notice: Subject to any disclaimer, the term of this patent is extended or adjusted under 35 U.S.C. 154(b) by 83 days.

(21) Appl. No.: 17/041,148

(22) PCT Filed: Mar. 27, 2019

(86) PCT No.: PCT/US2019/024282
§ 371 (c)(1),
(2) Date: Sep. 24, 2020

(87) PCT Pub. No.: WO2019/191232
PCT Pub. Date: Oct. 3, 2019

(65) Prior Publication Data
US 2021/0010002 A1    Jan. 14, 2021

Related U.S. Application Data

(60) Provisional application No. 62/648,648, filed on Mar. 27, 2018.

(51) Int. Cl.
*C07H 21/04* (2006.01)
*C12N 15/113* (2010.01)

(52) U.S. Cl.
CPC ...... *C12N 15/113* (2013.01); *C12N 2310/315* (2013.01); *C12N 2310/321* (2013.01); *C12N 2310/335* (2013.01)

(58) Field of Classification Search
None
See application file for complete search history.

(56) References Cited

U.S. PATENT DOCUMENTS 6,531,456 B1   3/2003  Kurtzman et al.
8,603,457 B2   12/2013 Yu et al.

FOREIGN PATENT DOCUMENTS

| EP | 3353299 B1 | 3/2020 |
|---|---|---|
| WO | WO-1998/50586 A1 | 11/1998 |
| WO | WO-2005094370 A2 | 10/2005 |
| WO | WO-2007/064952 A2 | 6/2007 |
| WO | WO-2010115206 A2 | 10/2010 |
| WO | WO-2012006241 A2 | 1/2012 |
| WO | WO-2014011053 A1 | 1/2014 |
| WO | WO-2017050306 A1 | 3/2017 |

OTHER PUBLICATIONS

Adachi et al. (2019) Methods Mol. Biol., 1870: 219-235.
Bortolin et al. (1999) "Elements essential for accumulation and function of small nucleolar RNAs directing site-specific pseudouridylation of ribosomal RNAs," EMBO J., 18(2): 457-469.
Carlile et al. (2014) Nature, 515: 143-146.
Chen et al. (2010) Mol. Cell Biol., 30: 4108-4119.
Darzacq et al. (2002) EMBO J., 21(11): 2746-2756.
Fernandez et al. (2013) Nature, 500: 107-110.
Ge et al. (2013) Trends Biochem. Sci., 38(4): 210-218.
International Search Report for PCT/US2019/024282, dated Nov. 19, 2019 (8 pgs.).
Jady (2001) "A small nucleolar guide RNA functions both in 2'-O-ribose methylation and pseudouridylation of the U5 spliceosonal RNA," EMBO J., 20(3): 541-551.
Karijolich et al. (2011) "Converting nonsense codons into sense codons by targeted pseudouridylation," Nature, 474 (7351): 395-398.
Kiss et al. (1995) Genes Dev., 9(11): 1411-1424.
Lancaster et al. (2014) Science, 345(6194): 1247125.
Leverette et al. (1992) Cell, 71(7): 1215-1221.
Li et al. (2006) Nature, 443: 302-307.
Li et al. (2011) Genes Dev., 25: 2409-2421.
Pappu et al. (1998) J. Phys. Chem. B., 102: 9725-9742.
Richard et al. (2006) "Cotranscriptional Recognition of Human Intronic Box H/ACA snoRNAs Occure in a Splicing-Independent Manner," Mol. Cell. Biol., 26(7): 2540-2549.

(Continued)

*Primary Examiner* — Kimberly Chong
(74) *Attorney, Agent, or Firm* — Sterne, Kessler, Goldstein & Fox P.L.L.C.

(57) ABSTRACT

The invention relates to nucleic acid molecules for pseudouridylation of a target uridine in a target RNA in a mammalian cell, wherein the nucleic acid molecule comprises a guide region capable of forming a partially double stranded nucleic acid complex with the target RNA comprising the target uridine, wherein the partially double stranded nucleic acid complex is capable of engaging a mammalian pseudouridylation enzyme, wherein the guide region assists in positioning the target uridine in the partially double stranded nucleic acid complex for it to be converted to a pseudouridine by the mammalian pseudouridylation enzyme.

24 Claims, 21 Drawing Sheets

Specification includes a Sequence Listing.

(56) References Cited

OTHER PUBLICATIONS

Scott et al. (2009) "Human miRNA Precursors with Box H/ACA snoRNA Features," Plos Computational Biology, 5(9): e1000507.
Wang et al. (2004) "Architecture and assembly of mammalian H/ACA small nucleolar and telomerase ribonucleoproteins," EMBO J., 23(8): 1857-1867.
Woeller et al. (2008) EMBO Reports, 9(5): 446-451.
Written Opinion for PCT/US2019/024282, dated Nov. 19, 2019 (10 pgs.).
Wu et al. (2015) "Pseudouridine in mRNA: Incorporation, Detection, and Recoding" in "Protein Engineering," Methods in Enzymology, 560: 187-217.
Wu et al. (2016) "Pseudouridines in U2 snRNA stimulate the ATPase activity of Prp5 during spliceosome assembly," EMBO J., 35(6): 654-667.
Xiao et al. (2009) "Functionality and substrate specificity of human box H/ACA guide RNAs," RNA, 15: 176-186.
Yu et al. (2014) RNA Biology, 11: 1483-1494.
Zhang et al. (1998) RNA, 4(7): 801-815.
Zhao et al. (2002) "An H/ACA guide RNA directs Us pseudouridylation at two different sites in the branchpoint recognition region in Xenopus oocytes," RNA, 12" 1515-1525.
International Preliminary Report on Patentability for PCT/US2019/024282, completed May 20, 2020 (18 pgs.).
Aruscavage, P. J., and Bass, B. L., "A Phylogenetic Analysis Reveals an Unusual Sequence Conservation Within Introns Involved in RNA Editing," RNA 6(2):257-269, Cold Spring Harbor Laboratory Press, United States (Feb. 2000).
Garncarz, W., et al., "A High-throughput Screen to Identify Enhancers of ADAR-mediated RNA-editing," RNA Biology 10(2):192-204, Landes Bioscience, United States (Feb. 2013).
Lomeli, H., et al., "Control of kinetic properties of AMPA receptor channels by nuclear RNA editing," Science 266(5191):1709-1713, American Association for the Advancement of Science, United States (Dec. 1994).
Macbeth, M. R., et al., "Evidence for Auto-inhibition by the N Terminus of hADAR2 and Activation by dsRNA Binding," RNA 10:1563-1571, Cold Spring Harbor Laboratory Press, United States (Oct. 2004).
Montiel-Gonzalez, M.F., et al., "Correction of Mutations Within the Cystic Fibrosis Transmembrane Conductance Regulator by Site-directed RNA Editing," Proc Natl Acad Sci USA 110(45):18285-18290, National Academy of Sciences, United States (2013).
Rieder, L.E., et al., "Tertiary Structural Elements Determine the Extent and Specificity of Messenger RNA Editing," Nature Communications 4:2232, Nature Publishing Group, United Kingdom (Aug. 2013).
Stefl, R., and Allain, F. H., "A Novel RNA Pentaloop Fold Involved in Targeting ADAR2," RNA 11(5):592-597, Cold Spring Harbor Laboratory, United States (May 2005).
Wong, S.K., et al., "Substrate Recognition by ADAR1 and ADAR2," RNA 7:846-858, Cold Spring Harbor Laboratory, United States (Jun. 2001).
Woolf, T.M., et al., "Toward the Therapeutic Editing of Mutated RNA Sequences," Proc Natl Acad Sci USA 92(18):8298-8302, National Academy of Sciences, United States (1995).
Savva, Y.A., et al. "The ADAR protein family," Genome Biology 13:252, BioMed Central, United States (Dec. 2012).

(Uridine)    (Ψ)

A                   B gcgcccaatacgcaaaccgcctctccccgcgcgttggccgattcattaatgcagctggcacgacaggtttcccga
ctggaaagcgggcagtgagcgcaacgcaattaatgtgagttagctcactcattaggcaccccacactttatgctt
ccggctcgtatgttgtgtggaattgtgagcggataacaatttcacacaggaaacagctatgaccatgattacgcc
aagctcggatcctagagatatactgagtcattagggactttccaatggghtttgcccagtacataaggtcaatag
gggtgaatcaacaggaaagtcccattggagccaagtacactgagtcaatagggactttccattgggttttgccca
gtacaaaaggtcaataggggtgagtcaatgggttttcccattattggcacgtacataaggtcaataggggtga
gtcattgggttttccagccaatttaattaaaacgccatgtactttcccaccattgacgtcaatgggctattgaa
actaatgcaacgtgacctttaaacggtactttcccatagctgattaatgggaaagtaccgttctcgagccaatac
acgtcaatgggaagtgaaagggcagccaaaacgtaacaccgccccggttttcccctggaaattccatattggcac
gcattctattggctgagctgcgttctacgtgggtataagaggcgcgaccagcgtcggtaccgtcgcagtcttcgg
tctgaccaccgtagaacgcagatcgaattgatcccgcgcagacactgaccttcagcgcctcggctccagcgccat
ggcttccaaggctcgagctcagtacatcaagagcttcgtggagcgcgtgctgaagaacgagcagtacATGGTGCA
CCTGACTCCTGAGGAGAAGTCTGCCGTTACTGCCCTGTGGGGCAAGGTGAACGTGGATGAAGTTGGTGGTGAGGC
CCTGGGCAG*GTAAGTCGAC*GTGGGAGATTCTGCCTCGGACAGAGAGAAACTCTG
CTGTGTCTGAGAGTTGATCTCCCTATAGTGACCCTGCCTTCTTGCCC
CGGGACGAAATGAGAGAAATCGTAACGGGAGTTTACGAGGCAGACAG
GT*TGACTCTCTCTTTTCCCCTGCAG*GCTGCTGGTGGTCTACCCTTGGACCCAGAGGTTCTTTGAGTCCTTTGGG
GATCTGTCCACTCCTGATGCTGTTATGGGCAACCCTAAGGTGAAGGCTCATGGCAAGAAAGTGCTCGGTGCCTTT
AGTGATGGCCTGGCTCACCTGGACAACCTCAAGGGCACCTTTGCCACACTGAGTGAGCTGCACTGTGACAAGCTG
CACGTGGATCCTGAGAACTTCAGGgtgagtctgatgggcacctcctgggtttccttcccctggctattctgctca
accttcctatcagaaaaaaggggaagcgattctagggagcagtctccatgactgtgtgtggagtgttgacaaga
gttcggatatttattctctactcagaattgctgctcccccctcactctgttctgtgttgtcatttcctctttctt
tggtaagcttttaatttccagttgcattttactaaattaattaagctggttatttacttcccatcctgatatcag
cttcccctcctccttttcctcccagtccttctctctctcctctctctttctctaatcctttcctttccctcagttc
atttcttcttcttgtatctacgtttgtttgtcttttttaaatattgccttgtaacttgctcagaggacaaggaaga
tatgtccctgtttcttctcatagctctcaagaatagtagcataattggcttttatgccagggtgacaggggaaga
atatattttacatataaattctgtttgacataggattcttataataatttgtcagtagtttaaggttgcaaacaa
atgtctttgtaaataagcctgcagtatctggtattttgctctacagttatgttgatggttcttccatattccca
cagctcctgggcaatatgatcgtgattgtgctgggccaccacctgggcaaggatttcacccccgctgcacaggct
gccttccagaaggtggtggctggagtggccactgccctggctcacaagtaccactaaaccccctttcctgctctt
gcctgtgaacaatggttaattgttcccaagagagcatctgtcagttgttggcaaaatgatagacatttgaaaatc
tgtcttctgacaaataaaaagcatttatgttcactgcaatgatgtttaaattatttgtctgtgtcatagaaggg
tttatgctaagttttcaagatacaaagaagtgagggttcaggtctgaccttggggaaataaatgaattacacttc
aaatgtgtgggacagcaagcagtaagccacagatcctattgccatgcctaaacactcagagaaaaattcaacaa
atggtttcatttacacactacattatgattacatttatgtaaattatttgttttttctactcttccacataaa
tgtcttttttttcctcttacctacccagcacttcacagttctcaagccaataattttctttttgtaaaactaccat
tattctctaaacttttccctctgtgtttaccaagcaacattatttatcttttcataaatcctgttgccttagaca
gcttcagtagcaatagaggtaggattaaggagagaatagaagtgccctgtttgtcataccatgcctgcacagtca
atagtcactatgggatttcaaatggcactttgcctgggacctttacacttcacaccatactctggcttgagttag
gagttaagaatgagagaaatataagtctagagagaataagaatatctagttttaaggctcattactggggtctt
atgaaatttccataatacctgtaaatggaagcatttattttttcaataaatctatcttgaatatccagtgtggg
ttaggattaaatctctccttcatacagttggactgctttatttatatggagttactagagttaattcactggcc
gtcgttttacaacgtcgtgactgggaaaaccctggcgttacccaacttaatcgccttgcagcacatccccctttc
gccagctggcgtaatagcgaagaggcccgcaccgatcgcccttcccaacagttgcgcagcctgaatggcgaatgg
cgcctgatgcggtattttctccttacgcatctgtgcggtatttcacaccgcatatggtgcactctcagtacaatc
tgctctgatgccgcatagttaagccagccccgacacccgccaacacccgctgacgcgccctgacgggcttgtctg
ctcccggcatccgcttacagacaagctgtgaccgtctccgggagctgcatgtgtcagaggttttcaccgtcatca
ccgaaacgcgcgagacgaaaggcctcgtgatacgcctatttttataggttaatgtcatgataataatggtttct
tagacgtcaggtggcacttttcggggaaatgtgcgcggaaccccatttgtttatttttctaaatacattcaaat
atgtatccgctcatgagacaataaccctgataaatgcttcaataatattgaaaaaggaagagtatgagtattcaa
catttccgtgtcgcccttattcccttttttgcggcattttgccttcctgtttttgctcacccagaaacgctggtg
aaagtaaaagatgctgaagatcagttgggtgcacgagtgggttacatcgaactggatctcaacagcggtaagatc

FIG. 13

```
cttgagagttttcgccccgaagaacgttttccaatgatgagcactttaaagttctgctatgtggcgcggtatta
tcccgtattgacgccgggcaagagcaactcggtcgccgcatacactattctcagaatgacttggttgagtactca
ccagtcacagaaaagcatcttacggatggcatgacagtaagagaattatgcagtgctgccataaccatgagtgat
aacactgcggccaacttacttctgacaacgatcggaggaccgaaggagctaaccgcttttttgcacaacatgggg
gatcatgtaactcgccttgatcgttgggaaccggagctgaatgaagccataccaaacgacgagcgtgacaccacg
atgcctgtagcaatggcaacaacgttgcgcaaactattaactggcgaactacttactctagcttcccggcaacaa
ttaatagactggatggaggcggataaagttgcaggaccacttctgcgctcggccttccggctggctggtttatt
gctgataaatctggagccggtgagcgtgggtctcgcggtatcattgcagcactggggccagatggtaagccctcc
cgtatcgtagttatctacacgacggggagtcaggcaactatggatgaacgaaatagacagatcgctgagataggt
gcctcactgattaagcattggtaactgtcagaccaagtttactcatatatactttagattgatttaaaacttcat
ttttaatttaaaaggatctaggtgaagatcctttttgataatctcatgaccaaaatcccttaacgtgagttttcg
ttccactgagcgtcagaccccgtagaaaagatcaaaggatcttcttgagatcctttttttctgcgcgtaatctgc
tgcttgcaaacaaaaaaaccaccgctaccagcggtggtttgtttgccggatcaagagctaccaactctttttccg
aaggtaactggcttcagcagagcgcagataccaaatactgtccttctagtgtagccgtagttaggccaccacttc
aagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgcc
acgcttcccgaagggagaaaggcggacaggtatccggtaagcggcagggtcggaacaggagagcgcacgagggag
cttccaggggaaacgcctggtatctttatagtcctgtcgggtttcgccacctctgacttgagcgtcgattttg
tgatgctcgtcaggggggcggagcctatggaaaaacgccagcaacgcggccttttacggttcctggccttttgc
tggccttttgctcacatgttctttcctgcgttatcccctgattctgtggataaccgtattaccgcctttgagtga
gctgataccgctcgccgcagccgaacgaccgagcgcagcgagtcagtgagcgaggaagcggaaga
```

FIG. 13 (CONTINUED)

```
CCATTCGCCATTCAGGCTGCGCAACTGTTGGGAAGGGCGATCGGTGCGGGCCTCTTCGCTATTACGCCAGCTGGC
GAAAGGGGGATGTGCTGCAAGGCGATTAAGTTGGGTAACGCCAGGGTTTTCCCAGTCACGACGTTGTAAAACGAC
GGCCAGTGCCAAGCTGATCTATACATTGAATCAATATTGGCAATTAGCCATATTAGTCATTGGTTATATAGCATA
AATCAATATTGGCTATTGGCCATTGCATACGTTGTATCTATATCATAATATGTACATTTATATTGGCTCATGTCC
AATATGACCGCCATGTTGACATTGATTATTGACTAGTTATTAATAGTAATCAATTACGGGGTCATTAGTTCATAG
CCCATATATGGAGTTCCGCGTTACATAACTTACGGTAAATGGCCCGCCTGGCTGACCGCCCAACGACCCCCGCCC
ATTGACGTCAATAATGACGTATGTTCCCATAGTAACGCCAATAGGGACTTTCCATTGACGTCAATGGGTGGAGTA
TTTACGGTAAACTGCCCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTGGCAGTACATCTACGT
ATTAGTCATCGCTATTACCATGGTGATGCGGTTTTGGCAGTACACCAATGGGCGTGGATAGCGGTTTGACTCACG
GGGATTTCCAAGTCTCCACCCCATTGACGTCAATGGGAGTTTGTTTTGGCACCAAAATCAACGGGACTTTCCAAA
ATGTCGTAATAACCCCGCCCCGTTGACGCAAATGGGCGGTAGGCGTGTACGGTGGGAGGTCTATATAAGCAGAGC
TCGTTTAGTGAACCGTCAGAATTGATCTACCATGGACTACAAAGACGATGACGACAAGCTTATGGACTACAAGGA
CGACGATGACAAGCATATGGTGCACCTGACTCCTGAGGAGAAGTCTGCCGTTACTGCCCTGTGGGCAAGGTGAA
CGTGGATGAAGTTGGTGGTGAGGCCCTGGGCAGGTTGGTATCAAGGTTACAAGACAGGTTTAAGGAGACCAATAG
AAACTGGGCATGTGGAGACAGAGAAGACTCTTGGGTTTCTGATAGGCACTGACTCTCTCTGCCTATTGGTCTATT
TTCCCACCCTTAGGCTGCTGGTGGATGGAGAACAACTCTAGGCAGAGGTCTCAAAATTTGGGGATCTGTCCACTC
CTGATGCTGTTATGGGCAACCCTAAGGTGAAGGCTCATGGCAAGAAAGTGCTCGGTGCCTTTAGTGATGGCCTGG
CTCACCTGGACAACCTCAAGGGCACCTTTGCCACACTGAGTGAGCTGCACTGTGACAAGCTGCACGTGGATCCTG
AGAACTTCAGGGGTGAGTCTATGGGACCCTTGATGTTTTCTTTCCCCTTCTTTTCTATGGTTAAGTTCATGTCATA
GGAAGGGGATAAGTAACAGGGTACAGTTTAGAATGGGAAACAGACGAATGATTGCATCAGTGTGGAAGTCTCAGG
ATCGTTTTAGTTTCTTTTATTTGCTGTTCATAACAATTGTTTTCTTTTGTTTAATTCTTGCTTTCTTTTTTTTTC
TTCTCCGCAATTTTTACTATTATACTTAATGCCTTAACATTGTGTATAACAAAAGGAAATATCTCTGAGATACAT
TAAGTAACTTAAAAAAAAACTTTACACAGTCTGCCTAGTACATTACTATTTGGAATATATGTGTGCTTATTTGCA
TATTCATAATCTCCCTACTTTATTTTCTTTTATTTTTAATTGATACATAATCATTATACATATTTATGGGTTAAA
GTGTAATGTTTTAATATGTGTACACATATTGACCAAATCAGGGTAATTTTGCATTTGTAATTTTAAAAAATGCTT
TCTTCTTTTAATATACTTTTTTTGTTTATCTTATTTCTAATACTTTCCCTAATCTCTTTCTTTCAGGGCAATAATG
ATACAATGTATCATGCCTCTTTGCACCATTCTAAAGAATAACAGTGATAATTTCTGGGTTAAGGCAATAGCAATA
TCTCTGCATATAAATATTTCTGCATATAAATTGTAACTGATGTAAGAGGTTTCATATTGCTAATAGCAGCTACAA
TCCAGCTACCATTCTGCTTTTATTTTATGGTTGGGATAAGGCTGGATTATTCTGAGTCCAAGCTAGGCCCTTTTG
CTAATCATGTTCATACCTCTTATCTTCCTCCCACAGCTCCTGGGCAACGTGCTGGTCTGTGTGCTGGCCCATCAC
TTTGGCAAAGAATTCACCCCACCAGTGCAGGCTGCCTATCAGAAAGTGGTGGCTGGTGTGGCTAATGCCCTGGCC
CACAAGTATCACTAAGCTCGCTTTCTTGCTGTCCAATTTCTATTAAAGGTTCCTTTGTTCCCTAAGTCCAACTAC
TAAACTGGGGGATATTATGAAGGGCCTTGAGCATCTGGATTCTGCCTAATAAAAAACATTTATTTTCATTGCAAT
GATGTATTTAAATTATTTCTGAATATTTTACTAAAAAGGGAATGTGGGAGGTCAGTCTAGAGGATCCCGGGTGGC
ATCCCTGTGACCCCTCCCCAGTGCCTCTCCTGGCCCTGGAAGTTGCCACTCCAGTGCCCACCAGCCTTGTCCTAA
TAAAATTAAGTTGCATCATTTTGTCTGACTAGGTGTCCTTCTATAATATTATGGGGTGGAGGGGGGTGGTATGGA
GCAAGGGGCAAGTTGGGAAGACAACCTGTAGGGCCTGCGGGGTCTATTGGGAACCAAGCTGGAGTGCAGTGGCAC
AATCTTGGCTCACTGCAATCTCCGCCTCCTGGGTTCAAGCGATTCTCCTGCCTCAGCCTCCCGAGTTGTTGGGAT
TCCAGGCATGCATGACCAGGCTCAGCTAATTTTTGTTTTTTTGGTAGAGACGGGGTTTCACCATATTGGCCAGGC
TGGTCTCCAACTCCTAATCTCAGGTGATCTACCCACCTTGGCCTCCCAAATTGCTGGGATTACAGGCGTGAACCA
CTGCTCCCTTCCCTGTCCTTCTGATTTTAAAATAACTATACCAGCAGGAGGACGTCCAGACACAGCATAGGCTAC
CTGGCCATGCCCAACCGGTGGGACATTTGAGTTGCTTGCTTGGCACTGTCCTCTCATGCGTTGGGTCCACTCAGT
AGATGCCTGTTGAATTGGGTACGCGGCCAGCTTGGCTGTGGAATGTGTGTCAGTTAGGGTGTGGAAAGTCCCCAG
GCTCCCCAGCAGGCAGAAGTATGCAAAGCATGCATCTCAATTAGTCAGCAACCAGGTGTGGAAAGTCCCCAGGCT
CCCCAGCAGGCAGAAGTATGCAAAGCATGCATCTCAATTAGTCAGCAACCATAGTCCCGCCCCTAACTCCGCCCA
TCCCGCCCCTAACTCCGCCCAGTTCCGCCCATTCTCCGCCCCATGGCTGACTAATTTTTTTTATTTATGCAGAGG
CCGAGGCCGCCTCGGCCTCTGAGCTATTCCAGAAGTAGTGAGGAGGCTTTTTTGGAGGCCTAGGCTTTTGCAAAA
AGCTCCTCGAGGAACTGAAAAACCAGAAAGTTAATTCCCTATAGTGAGTCGTATTAAATTCGTAATCATGTCATA
GCTGTTTCCTGTGTGAAATTGTTATCCGCTCACAATTCCACACAACATACGAGCCGGAAGCATAAAGTGTAAAGC
CTGGGGTGCCTAATGAGTGAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAAGGCCAGGAACCGTAA
```

FIG. 14

```
AAAGGCCGCGTTGCTGGCGTTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAACTACGG
CTACACTAGAAGAACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGGCTTACCATCTGGCCC
CAGTGCTGCAATGATACCGCGAGA
```

FIG. 14 (CONTINUED)

Zoom and higher contrast

NUCLEIC ACID MOLECULES FOR PSEUDOURIDYLATION

CROSS REFERENCE TO RELATED APPLICATIONS

This application is a § 371 National Stage Application of PCT/US2019/024282, filed Mar. 27, 2019, which claims priority to and the benefit of U.S. Provisional Patent Application No. 62/648,648, filed on Mar. 27, 2018, the entire disclosures of each of which are incorporated herein by reference for all purposes.

SEQUENCE LISTING

The instant application contains a Sequence Listing which has been submitted electronically in ASCII format and is hereby incorporated by reference in its entirety. Said ASCII copy, created on Mar. 21, 2019, is named PQR_021WO_SL25.txt and is 32,768 bytes in size.

FIELD OF THE INVENTION

The invention relates to the field of medicine. More in particular, the invention relates to the field of pseudouridylation, whereby an RNA molecule in a cell is targeted by a nucleic acid molecule, such as an oligonucleotide, to recruit a pseudouridine synthase to convert a specific uridine present in the RNA sequence into pseudouridine. More specifically, the invention relates to oligonucleotides and intron-embedded snoRNAs that promote pseudouridylation of a uridine in a target RNA and methods of use thereof.

BACKGROUND OF THE INVENTION

Pseudouridine (ψ) is the most abundant post-transcriptionally modified nucleotide in stable RNAs, including tRNA, rRNA, snRNA and mRNA, constituting approximately 5% of total ribonucleotides. The conversion of uridine to ψ (pseudouridylation) requires two distinct chemical reactions: the breaking of the C1'-N1 glycosydic bond and the making of a new carbon (C1'-C5) bond that relinks the base to the sugar. Pseudouridylation is a true isomerization reaction, which creates an extra hydrogen bond donor and thereby influences a wide variety of functional aspects depending on the type of RNA that carries the ψ and the position within the RNA sequence, such as protein synthesis, increased stop-codon read-through and frame shifting (Yu and Meier, 2014, RNA Biology 11:1483-1494). FIG. 1 shows the structures of uridine and ψ. Many of the mRNA ψs reside in coding regions, and the majority of them respond to environmental stress, indicating functional significance (Carlile et al. 2014, Nature 515:143-146).

In eukaryotes and archaea, pseudouridylation is introduced among other proteins by box H/ACA ribonucleoproteins (RNPs), each of which contains a unique small RNA (box H/ACA RNA, one of the two major classes of small nucleolar RNAs, or 'snoRNAs') and four core proteins (NAP75/dyskerin/Cbf5, Nhp2, Nop10 and Gar1). NAP75/dyskerin/Cbf5 catalyses the chemical reactions, converting the target uridine to ψ. The RNA component serves as a guide that specifies, through base-pairing interaction with its substrate RNA, the target uridine for pseudouridylation (Ge and Yu, 2013, Trends Biochem Sci 38 (4):210-218). Based on this guide-substrate base-pairing scheme, Karijolich and Yu (2011, Nature 474:395-398) designed an artificial box H/ACA RNA to introduce ψ into mRNA at a Premature Termination Codon (PTC) in *S. cerevisiae*. They demonstrated that ψ was indeed incorporated into TRM4 mRNA at the PTC. Remarkably, pseudouridylated PTC promoted nonsense suppression by altering ribosome decoding (Fernandez et al. 2013, Nature 500:107-110; Wu et al. 2015, Methods in Enzymology 560:187-217; U.S. Pat. No. 8,603,457). Using a similar strategy, others showed that artificial H/ACA RNAs could site-specifically pseudouridylate pre-mRNA after microinjection into *Xenopus* oocytes (Chen et al. 2010, Mol Cell Biol 30:4108-4119). In both examples, the artificial H/ACA RNAs were modified to alter the loops that serve as the guide sequence, but otherwise these snoRNAs were unaltered and still full length.

Mammalian H/ACA snoRNAs are generally embedded (positioned) within pre-mRNA intronic regions of protein-coding genes. During transcription elongation, several proteins with a functional role in pseudouridylation, such as Nop10, dyskerin or Nhp2 bind to the nascent H/ACA snoRNA sequences, particularly to their structural core motifs. Following splicing, the guide RNAs are processed through debranching and exonucleolytic processing, resulting in a RNA-protein complex called 'small nuclear ribonucleoproteins' (snRNPs, or snRNP complex). Once in the mature form, these particles are intra-nuclearly trafficked from the transcription sites to the site where they are functionally active for pseudouridylation, mostly in the nucleolus but also in the Cajal bodies. During spliceosome-assembly these snRNPs are sequentially recruited on to a pre-mRNA substrate, onto which short RNA-RNA hybrids will form allowing specification of the pseudouridylation sites. Box H/ACA snoRNAs have no preference for localization relative to the 5' or 3' ends of the intron and can be present in small or very large introns, as opposed to box CID snoRNAs, which are usually localized 60-90 nucleotides upstream the 3'-splice site and are encoded in relatively small introns. Leverette et al. (1992, Cell 71 (7):1215-1221) proposed that some snoRNAs could be present in intronic regions of pre-mRNAs. Kiss and Filipowicz (1995, Genes Dev 9 (11):1411-1424) suggested that a given snoRNA sequence could be excised and fully processed from an intronic region of any given actively spliced mRNA. To show the feasibility of this approach, they artificially imbedded several snoRNAs (U17a, U17b and U19) into the second intron of the human β-globin gene and expressed the resulting vector in fibroblast-like cells. After transfection, they found that the artificial, intronically delivered snoRNAs were properly processed from the human β-globin intron and the globin pre-mRNA was correctly spliced. Notably, this did not happen when the guide RNA sequence was artificially embedded in an exon. Darzacq et al. (2002, EMBO J 21(11); 2746-2756) corroborated that other guide RNAs could be inserted into the second intron of the human β-globin gene using an expression vector under the control of the cytomegalovirus (CMV) promoter and be delivered to mammalian cells via transfection.

In spite of the above, and the fact that snoRNAs could be delivered to cells and be processed from intronic regions, no one—to the knowledge of the inventors of the present invention—has ever shown targeted pseudouridylation using snoRNAs in a mammalian system. The artificial H/ACA snoRNAs described in the prior art are typically in the range of about 140 nt and they consist of RNA, which makes that they tend to be quite unstable in vivo. Manufacturing and delivery of such molecules in a therapeutic setting therefore remains a challenge.

SUMMARY OF THE INVENTION

The present invention relates to a nucleic acid molecule for pseudouridylation of a target uridine in a target RNA in a mammalian cell, wherein the nucleic acid molecule comprises a guide region capable of forming a partially double stranded nucleic acid complex with the target RNA comprising the target uridine, wherein the partially double stranded nucleic acid complex is capable of engaging a mammalian pseudouridylation enzyme, wherein the guide region assists in positioning the target uridine in the partially double stranded nucleic acid complex for it to be converted to a pseudouridine by the mammalian pseudouridylation enzyme. Preferably, the pseudouridylation enzyme is part of a ribonucleoprotein (RNP) complex capable of acting on an H/ACA-snoRNA. In one embodiment of the invention, the nucleic acid molecule is shorter than a wild type H/ACA snoRNA and comprises one or more nucleosides and/or inter-nucleosidic linkages that are non-naturally modified compared to the wild type H/ACA snoRNA. In one particularly preferred aspect, the nucleic acid molecule comprises a single guide region corresponding to one of the two hairpin structures of the wild type H/ACA snoRNA, preferably the hairpin structure at the 3' terminal part of the wild type H/ACA snoRNA, more preferably wherein the 5' terminal nucleotide corresponds to a nucleotide from a region between the two hairpin structures of the wild type H/ACA snoRNA.

In another embodiment, the invention relates to a nucleic acid molecule according to the invention, wherein the nucleic acid molecule is positioned in an intron sequence from which it is expressed, and wherein the intron sequence is located between an upstream exon A sequence and a downstream exon B sequence. Preferably, the exon A/intron/exon B sequence is present in a vector, preferably a plasmid or a viral vector.

In yet another embodiment, the invention relates to a nucleic acid molecule according to the invention, wherein the nucleic acid molecule is present in a vector, such as a plasmid, and wherein the nucleic acid molecule is transcribed from a CMV or a pol-III promoter, preferably a U6 or an H1 promoter.

In a particularly preferred aspect, the invention relates to a nucleic acid molecule according to the invention, wherein the guide region is capable of forming a partially double stranded complex with the target RNA, which comprises a mutation that is associated with a genetic disorder, preferably wherein the mutation results in a Premature Termination Codon (PTC), wherein the PTC is the cause of the genetic disorder, and wherein the target uridine is in the PTC.

In another embodiment, the invention relates to a method for converting a uridine in a target RNA molecule into a pseudouridine, comprising the steps of contacting a target RNA comprising a target uridine with a nucleic acid molecule according to the invention in the presence of a pseudouridylation enzyme or RNP complex and allowing the uridine to be converted thereby, preferably wherein the pseudouridylation enzyme or RNP complex is present in a mammalian cell, preferably a human cell.

The invention also relates to a vector comprising an intron sequence that is located between an upstream exon A sequence and a downstream exon B sequence, wherein the exon A sequence and the exon B sequence are of a gene that is not the natural gene for the intron sequence, and wherein the intron sequence comprises a snoRNA sequence encoding a nucleic acid molecule comprising a guide region capable of forming a partially double stranded nucleic acid complex with a target RNA comprising a target uridine, wherein the partially double stranded nucleic acid complex is capable of engaging a mammalian pseudouridylation enzyme to form a functional RNP complex, in a cell, wherein the guide region correctly positions the target uridine for it to be converted by the RNP complex, and wherein the target uridine is converted by the RNP complex to a pseudouridine. Preferably, the vector is a plasmid or a viral vector.

The invention further relates to a method for converting a uridine in a target RNA molecule into a pseudouridine in a cell, preferably a human cell, comprising the steps of administering to the cell a vector according to the invention; allowing the transcription of the exon A/intron/exon B sequence; allowing splicing and the formation of the snoRNA positioned in the intron; and allowing the snoRNA to form a partially double stranded nucleic acid complex with the target RNA molecule, wherein the partially double stranded nucleic acid complex is capable of engaging a mammalian pseudouridylation enzyme to form a functional RNP complex, wherein the snoRNA correctly positions the target uridine for it to be converted by the RNP complex, and wherein the target uridine is converted by the RNP complex to a pseudouridine.

AGUAUAACUAUAAAUAGUAAUGCUG CCUGUGU-CCUUCAGACAAAA-3' (SEQ ID NO:5).

The two 28s rRNA sequences are as follows: 5'-aaagugaagaaauucaaugaagcgcggg-3' (SEQ ID NO:6; U3709; left guide region), and 5'-gaauccgacu-guuuaauuaaaaca-3' (SEQ ID NO:7; U3618; right guide region). In both 28s rRNAs the uridine that is converted to pseudo-U is underlined. The basic structure of the shortened pseudouridylation guide RNA as described herein is given on the right (B) and has the following sequence, which differs at the 5'-end because of residual nucleotides from the transcription, and which differs in the target loop because the sequence of the target mRNA differs from the 28s rRNA sequence (SEQ ID NO:7): 5'-GGAAUUGAAGGCU GGUUCGCAGUAUAACUAUAAAUAGUAAUGCUGC-CUGUGUCCUUCAGACAAAA-3' (SEQ ID NO:8).

Figure 5:
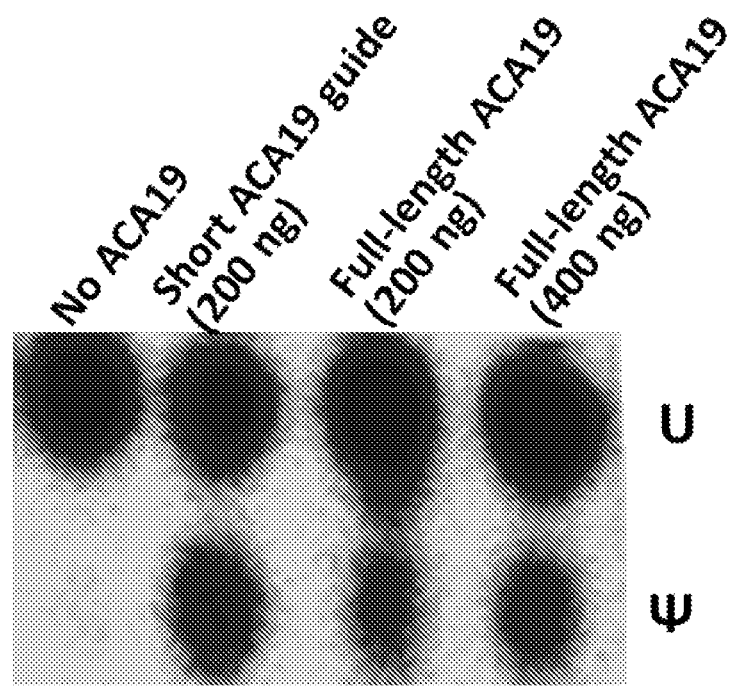

FIG. 5 shows results from a pseudouridylation assay of a radioactively labelled substrate RNA using either no guide (as the negative control), the shortened pseudouridylation guide RNA or the full-length ACA19 snoRNA at the amount indicated. U and Ψ indicate the migration of uridine and pseudouridine in the thin layer chromatography, respectively.

Figure 6:
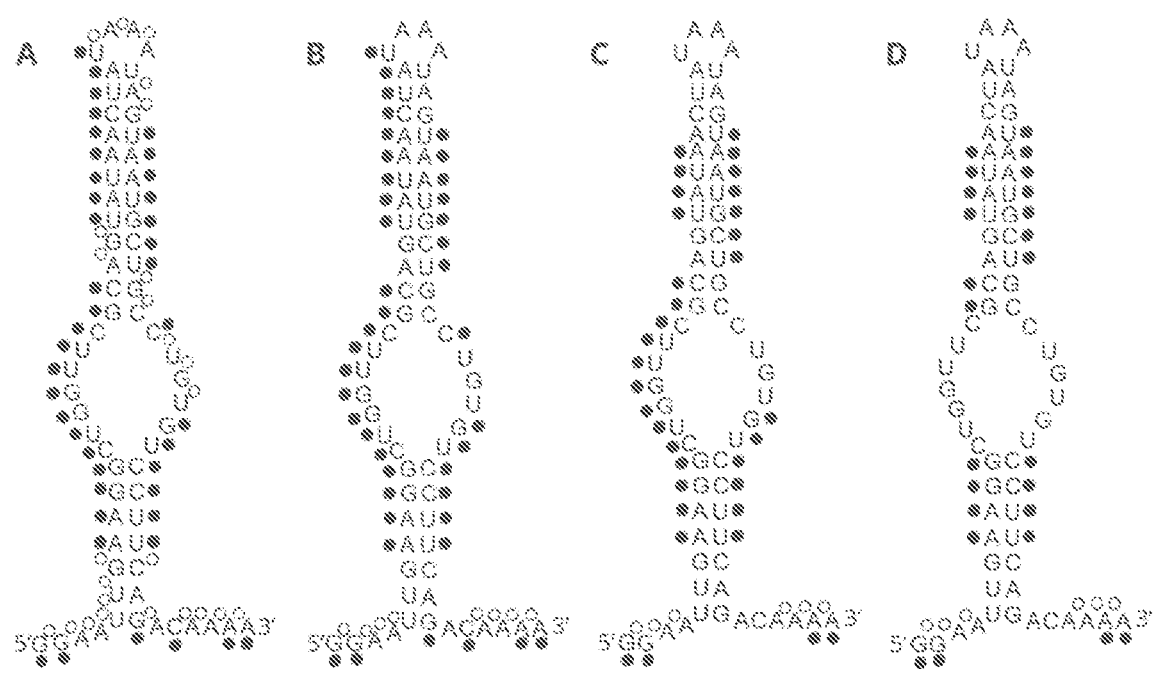

FIG. 6 shows the four ACA19 pseudouridylating editing oligonucleotides (psEONs), all with the sequence of SEQ ID NO:8, and the positions of the chemical modifications that were introduced: black dots indicate 2'-OMe modifications on the ribose moiety of that nucleotide, and open dots indicate PS modifications of the inter-nucleosidic linkage.

Figure 7:
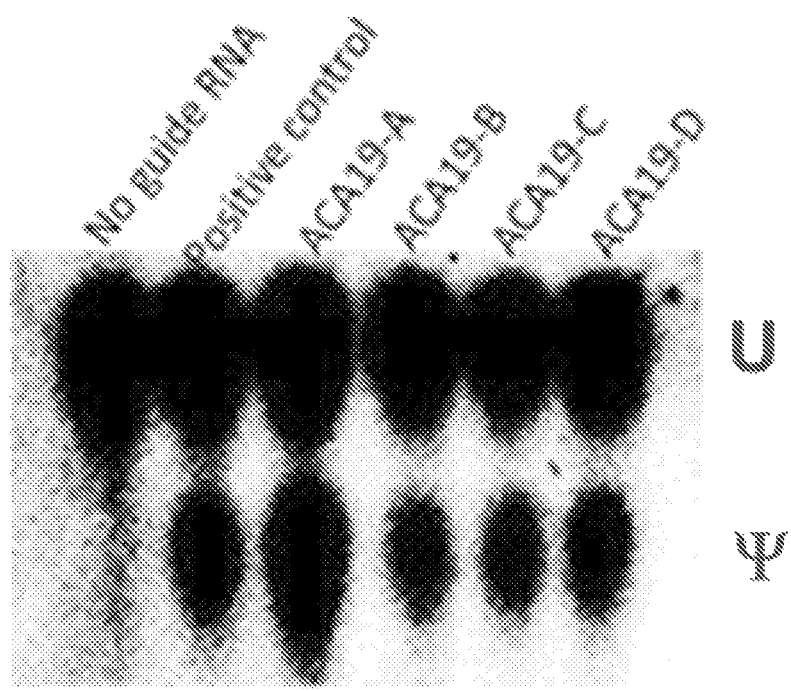

FIG. 7 shows the result of pseudouridylation using the four ACA19 psEONs together with the corresponding guide RNA (lacking chemical modifications) as a positive control and a negative control (no guide RNA). U and Ψ indicate the migration of uridine and pseudouridine in the thin layer chromatography, respectively.

Figure 8:
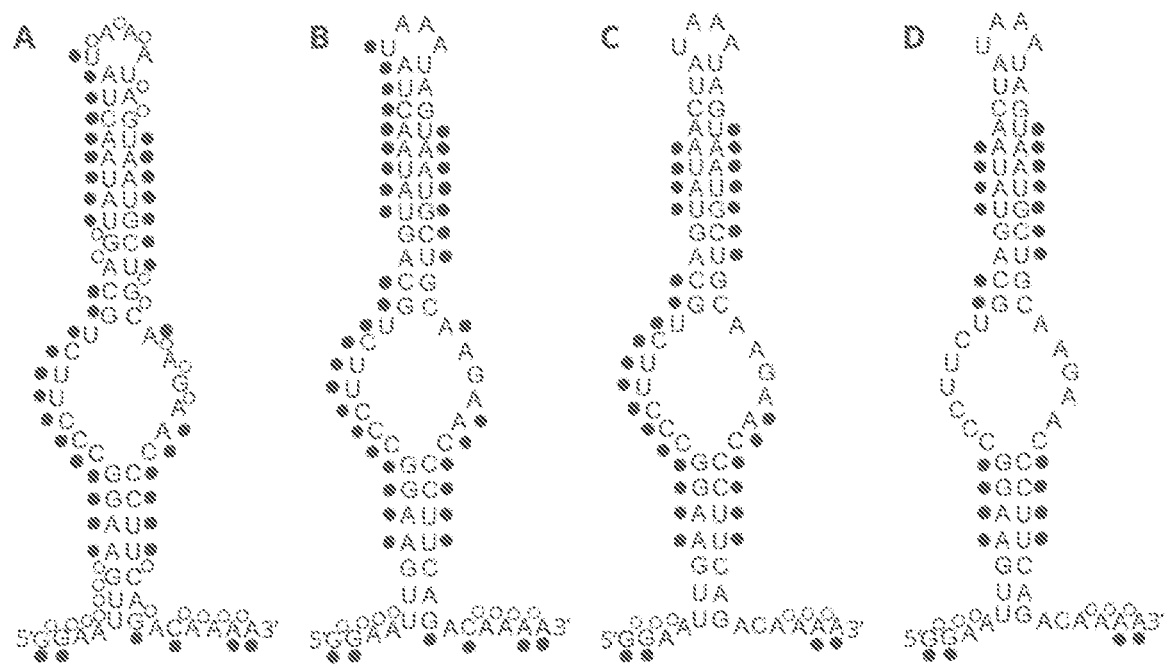

FIG. 8 shows the four CFTR-G542X psEONs (the guide pocket sequence is changed to target CFTR substrate in the same ACA19 backbone) and the positions of the chemical modifications that were introduced: dark dots indicate 2'-OMe modifications on the ribose moiety of that nucleotide, and open dots indicate phosphorothioate modification of the inter-nucleosidic linkage. The sequence for all these four psEONs is: 5'-GGAAUUGAAGGCCCUUCUGC-AGUAUAACU AUAAAU-AGUAAUGCUGCAAGAACCCUUCAGACAAAA-3' (SEQ ID NO:9).

Figure 9:
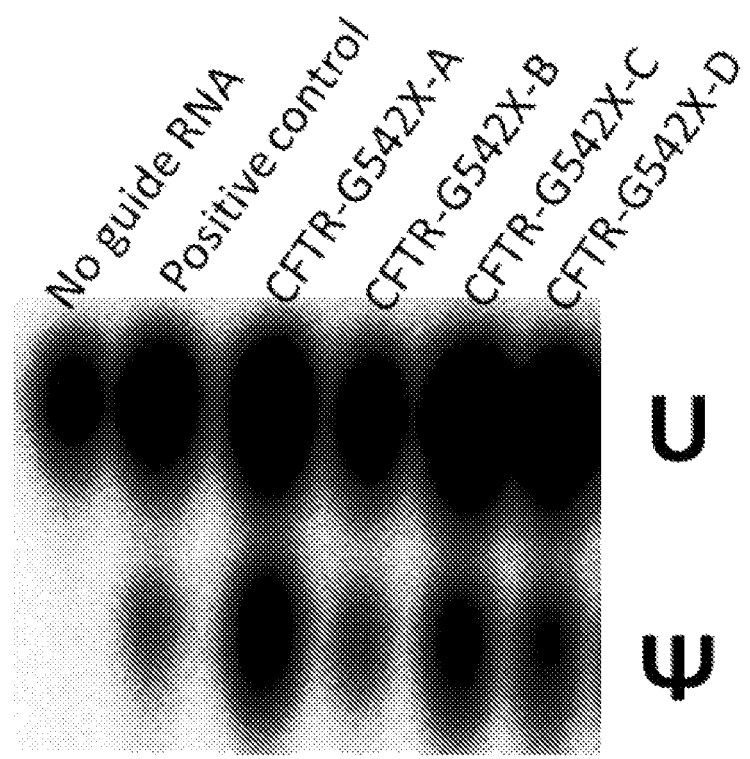

FIG. 9 shows the result of pseudouridylation using the four CFTR-G542X psEONs in parallel with the corresponding guide RNA (lacking chemical modifications) as a positive control and no guide RNA as a negative control. U and Ψ indicate the migration of uridine and pseudouridine in the thin layer chromatography, respectively.

Figure 10:
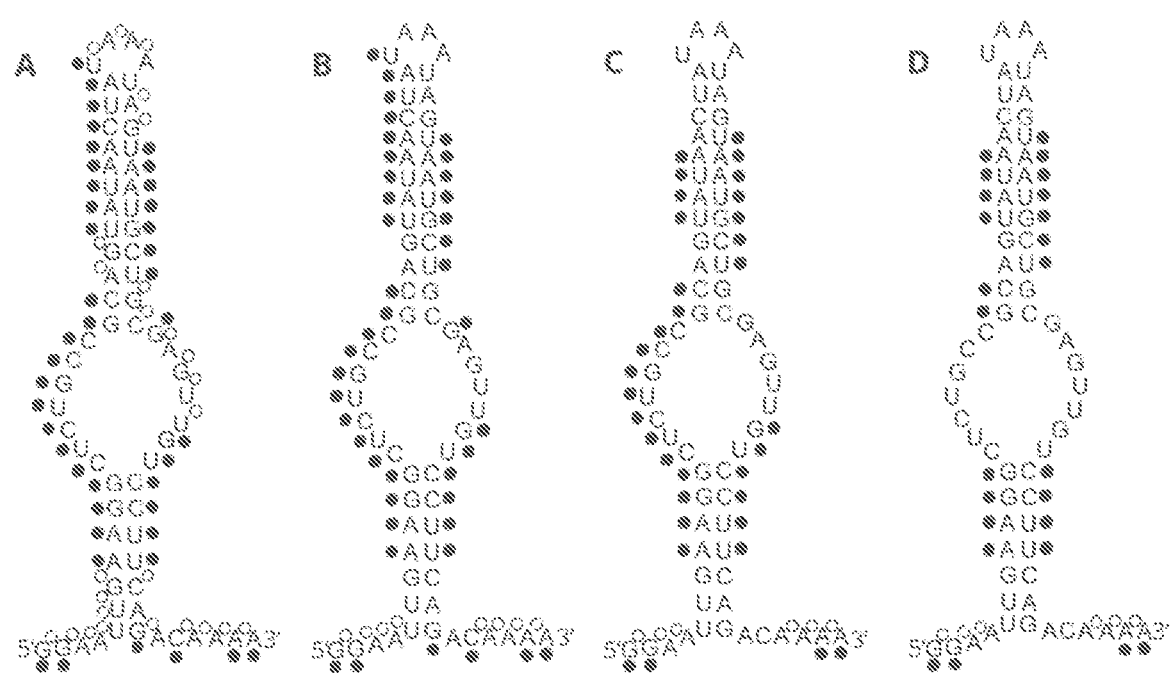

FIG. 10 shows the four Idua-W392X psEONs (from left to right Idua-A, -B, -C and -D) and the positions of the chemical modifications that were introduced: black dots indicate 2'-OMe modifications on the ribose moiety of that nucleotide, and open dots indicate PS modification of the inter-nucleosidic linkage. The sequence for all these four psEONs is: 5'-GGAAUUGA AGGCUCUGCCGC-AGUAUAACUAUAAAUAGUAAUGCUGCGAGUUGU-CCUUCAGAC AAAA-3' (SEQ ID NO:10).

Figure 11:
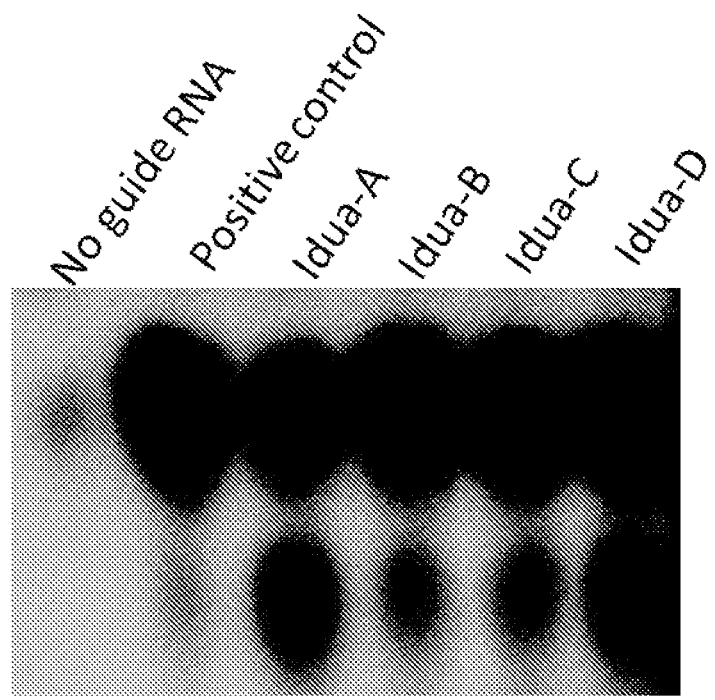

FIG. 11 shows the result of pseudouridylation using the four Idua-W392X psEONs (Idua-A, -B, -C and -D) in parallel with the corresponding guide RNA (lacking chemical modifications) as a positive control and no guide RNA as a negative control. U and Ψ indicate the migration of uridine and pseudouridine in the thin layer chromatography, respectively.

Figure 12:
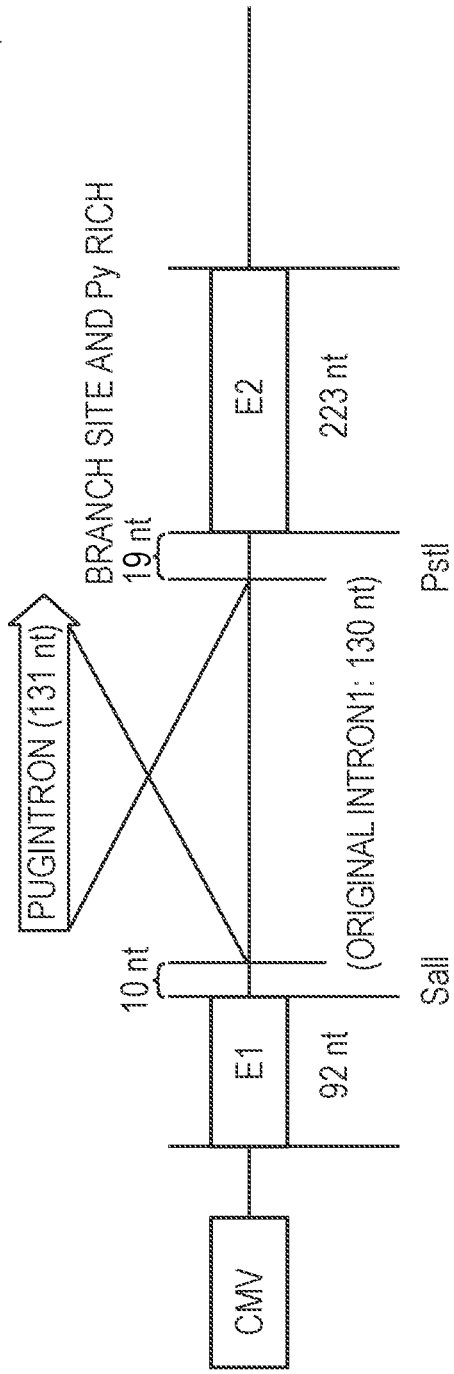

FIG. 12 shows a schematic view of the pugIntron-IDUA construct displaying the introduction of the 131 nt pugIntron insert located between the SalI site on the 5' end and the PstI site on the 3' end, with the 92 nt exon 1 (E1) and the 223 nt exon 2 (E2) of the human β-globin gene up- and downstream thereof, respectively. Transcription is driven by a CMV promoter.

FIG. 13 shows the entire nucleotide sequence of the pugIntron-mIDUA plasmid (SEQ ID NO:11) as shown schematically in FIG. 12, carrying the to-be-spliced out guide RNA. The plasmid sequences are given in lower case. The 131 nt guide RNA is given in a large font. The guide RNA is spliced out together with 10 nt upstream and 23 nt downstream. The upstream 92 nt exon 1 (E1 in FIG. 12) and the downstream 223 nt exon 2 (E2 in FIG. 12) are given in upper case and bold. The SalI and PstI restriction enzyme recognition sites are underlined.

FIG. 14 shows the entire sequence of the target pFLAG-GL39-IDUA swap expression vector (SEQ ID NO:12; originated from pFLAG2CMV2-HBB). The 33 nt mIDUA PTC region is in bold, and the TAG premature termination codon is underlined.

Figure 15:
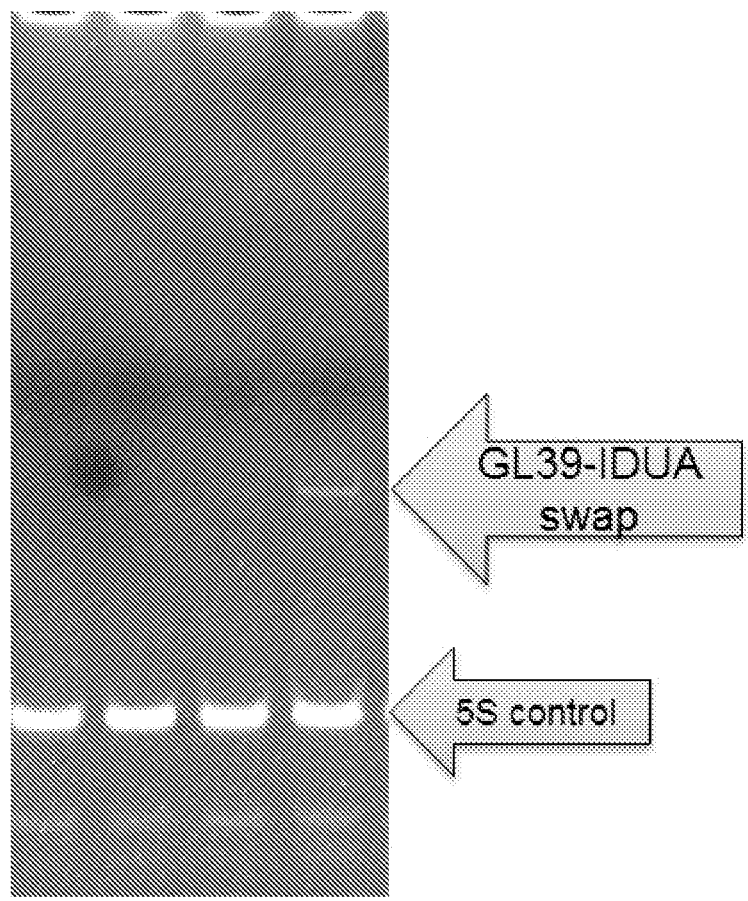

FIG. 15 shows the RT PCR analysis of β-globin mRNAs from HEK293 cells transfected with substrate plasmid "GL39-IDUA swap with or without pugIntronOpt-IDUA. The GL39 arrow indicates the product observed after RT-PCR. Lane 1 and 3 represent 15 PCR cycles and lane 2 and 4 represent 18 PCR cycles. Globin mRNA level was normalized by 5S control (lower arrow) and was found to be 0.00437 in lane 2, and 0.1617 in lane 4. Guide-induced RNA modification (here: pseudouridylation) suppressed NMD and upregulated the intact mRNA level 37-fold.

Figure 16:
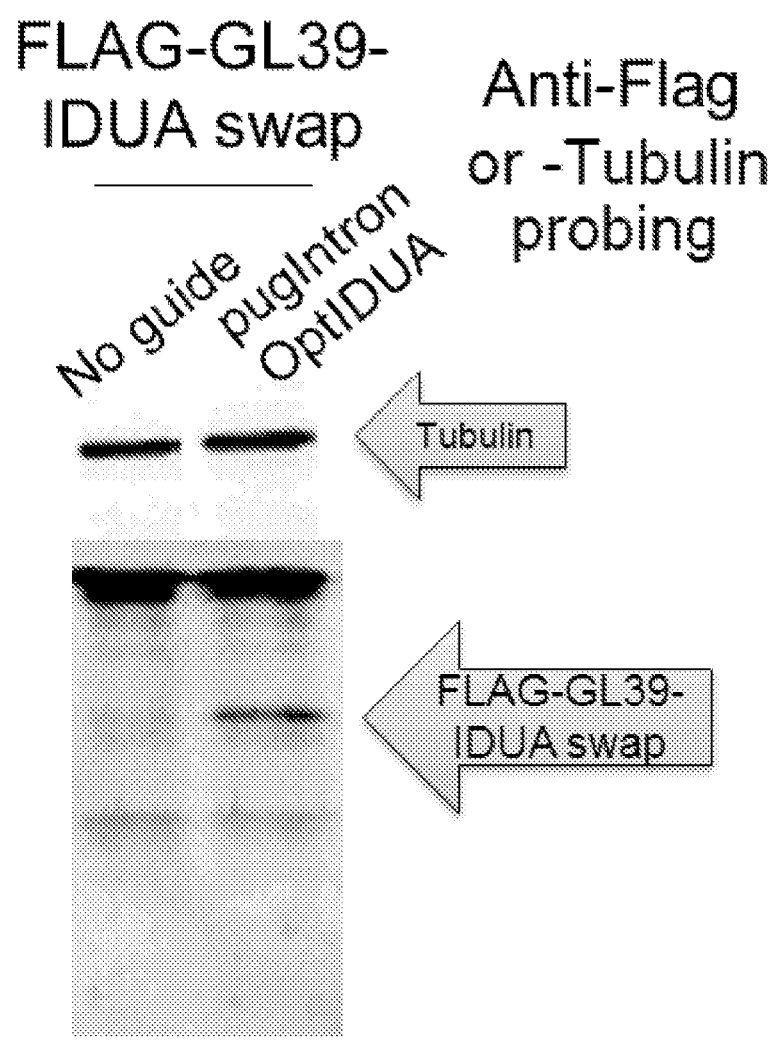

FIG. 16 shows the western blot analysis of flag-tagged globin proteins from HEK293 cells transfected with substrate FLAG-GL39-IDUA swap plasmid and guide pugIntron-IDUA plasmid. Cells were transfected with 250 ng substrate and 2.5 μg guide using PEI at 100% confluency.

Figure 17:
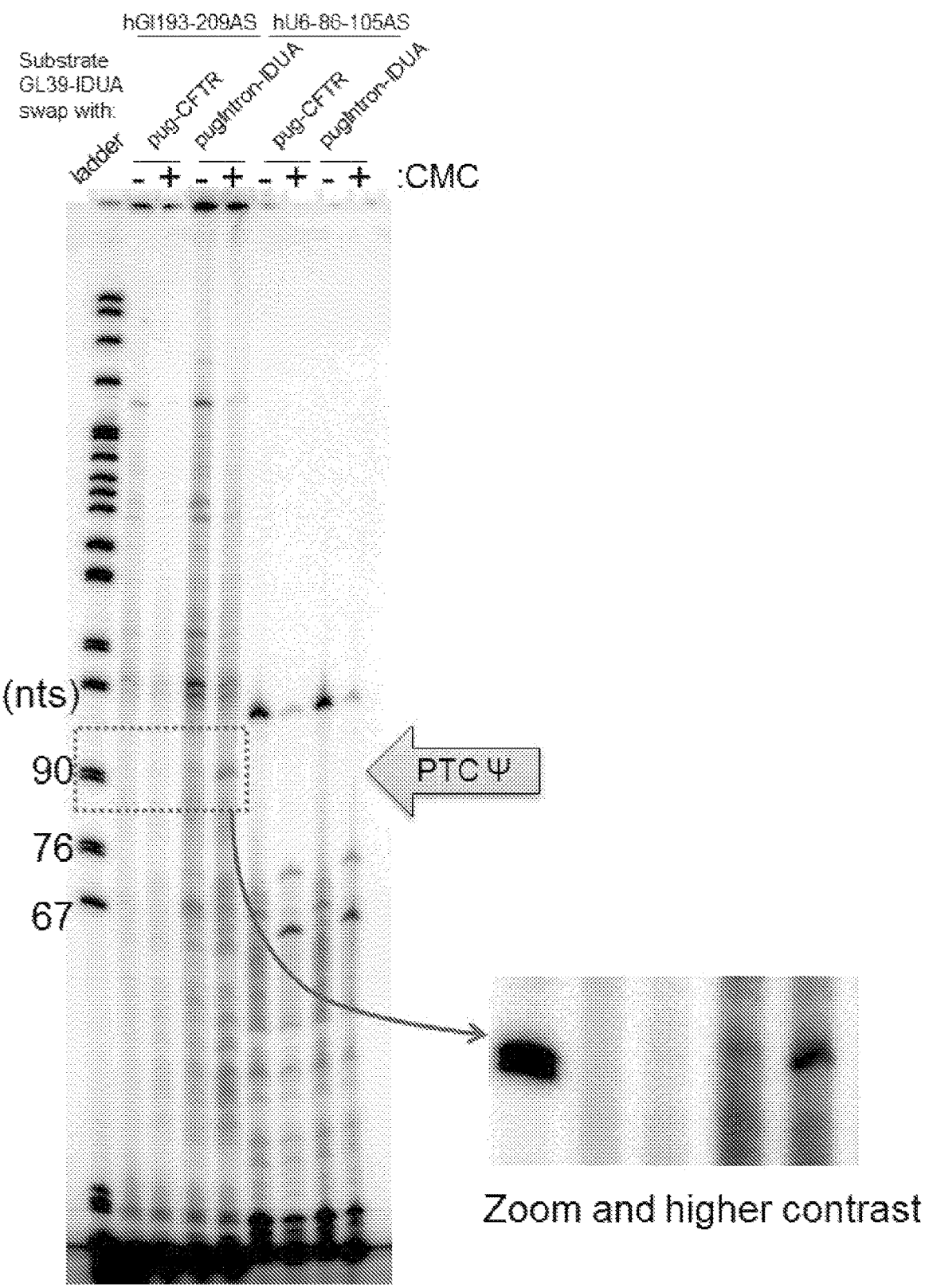

FIG. 17 shows the results of a primer extension experiments using total RNA obtained from HEK293T cells transfected with the substrate GL39-IDUA swap plasmid with pugIntron-IDUA as the guide RNA expressing plasmid or pug-CFTR as the negative control plasmid. RNA was treated with CMC and primer extension was carried out with a globin-specific primer and with a U6 specific primer as a control. The position of the 92 nt product terminated at the ψ-CMC residue is given by an arrow. This area is again represented in the zoomed-in panel. GL39+72 is the hG1193-209AS globin-specific primer. 90, 76 and 67 are size references from a pBR322-MspI digest (NEB #N3032).

Figure 18:
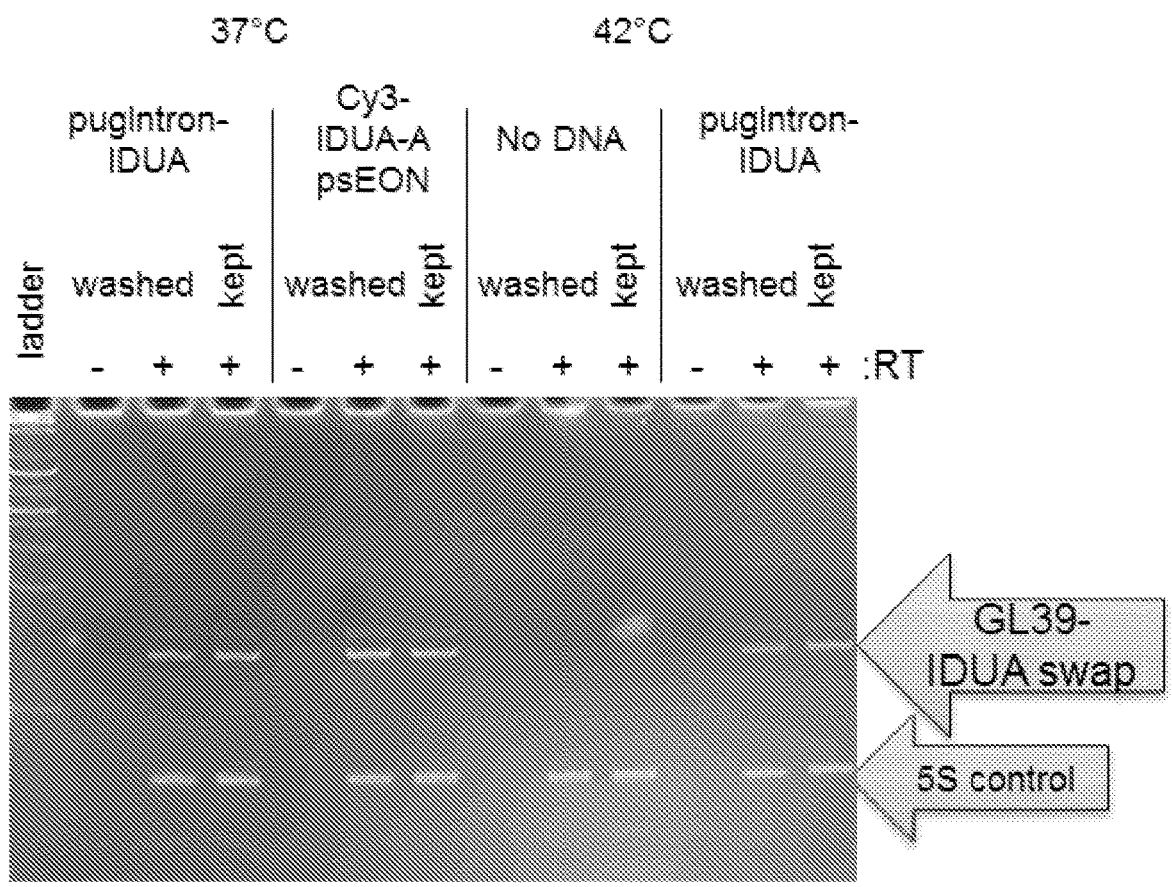

FIG. 18 shows the RT-PCR products from total RNA obtained from cells transfected with the GL39-IDUA swap substrate plasmid and the pugIntron-IDUA guide RNA expressing plasmid or with the Cy3-IDUA-A psEON (wherein the guide RNA is not intronically embedded). The GL39-IDUA arrow indicates the product observed after RT-PCR. The 5S control is also given with an arrow. No difference was observed when cells were washed (wash), or when the medium was kept (kept) on the cells after transfection. RT means reverse transcriptase (+ yes, or – no).

Figure 19:
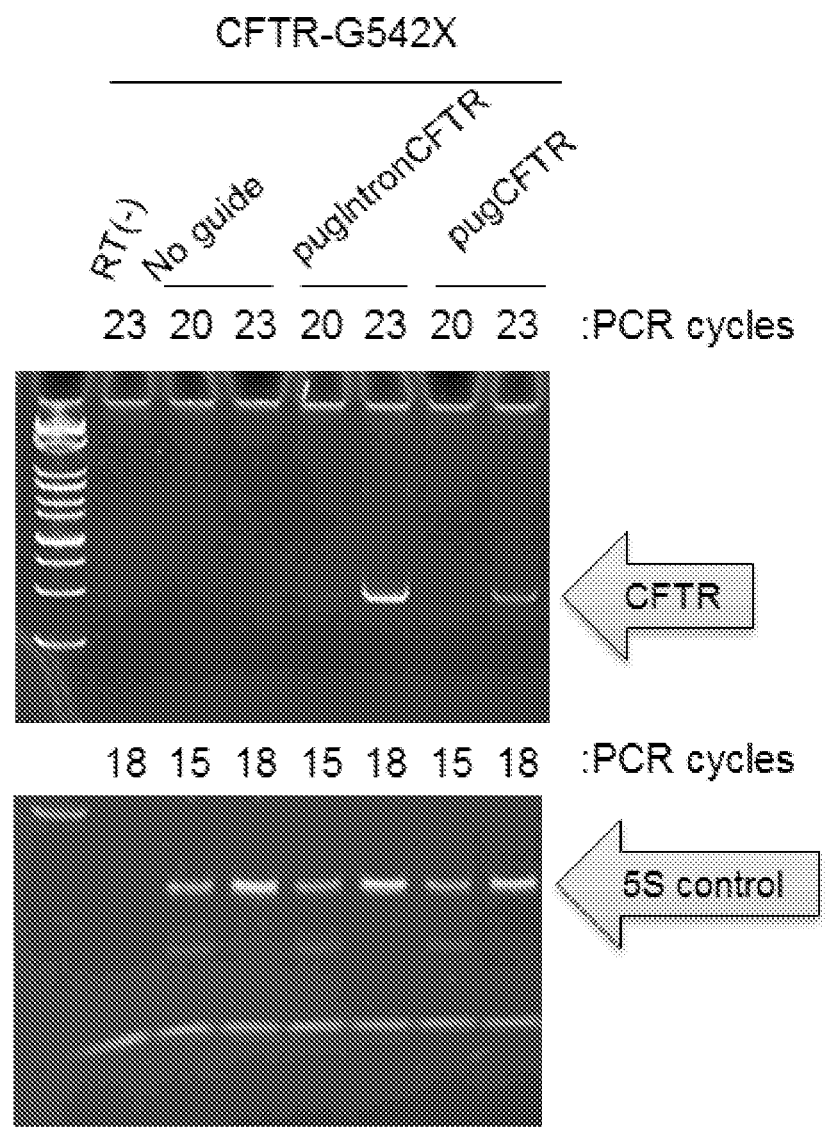

FIG. 19 shows the RT-PCR analysis of CFTR mRNAs from HEK293 cells transfected with substrate plasmid carrying the CFTR-G542X mutation, with either no guide (lanes 2 and 3 right from the ladder), negative control pugCFTR (lanes 6 and 7 right from the ladder) and guide snoRNA carrying plasmid pugIntCFTR (lanes 4 and 5 right from the ladder). The arrow indicates the product observed after RT-PCR. Lane 1 after the ladder represents the PCR without RT. Lanes 2, 4 and 6 represent product after 20 PCR cycles, while lanes 1, 3, 5, and 7 represent the product obtained after 23 cycles. The lower panel shows the 5S control after respectively 15 and 18 PCR cycles (instead of 20 and 23). The presence of the guide RNA expressed from pugIntCFTR clearly leads to NMD suppression as a stronger PCR product signal is observed.

DETAILED DESCRIPTION OF THE INVENTION

It is known in the art that full length H/ACA RNAs (snoRNAs) can be used to site-specifically convert a target uridine to pseudouridine (w). By changing the nucleic acid sequence of the two major loops that serve as guide for the natural substrate RNA, it was shown that other sequences than the natural sequence can be pseudouridylated in yeast and *Xenopus* systems. The inventors of the present invention, having the desire to perform targeted pseudouridylation in mammalian systems, with target RNAs that are potential therapeutic targets, asked themselves whether it would be possible to generate smaller pseudouridylation guide RNAs that would still be catalytically active and perhaps even have increased pseudouridylation effects. On top of that the inventors wondered whether it would be possible to increase the stability and/or specificity of such smaller oligonucleotides through chemical modifications. If such would work, these could potentially be used in vivo as pharmaceutically active compounds to be applied in therapeutic settings. Such guides could then potentially be used in the treatment of any genetic disorder in which a uridine (which may represent a mutation) would be converted to a ψ, and thereby either influence the content of the translated protein, or influence splicing, or increase (or decrease) protein translation from the resulting mRNA. Given the relatively low efficiency of the H/ACA snoRNAs in pseudouridylation as shown thus far in the art, there remains a need for improving the potency and pharmacokinetic properties of pseudouridylation guides. The present invention relates to such pseudouridylation guide compounds (also referred to herein as pseudouridylating editing oligonucleotides, or psEONs) that are shorter (in respect of nucleotide length) than the ones used in the art thus far, that carry one or more chemical modifications that influence the efficiency of pseudouridylation, or that are embedded in intronic regions to enable efficient delivery to mammalian cells. According to yet another embodiment, a nucleic acid sequence is provided that is or comprises a guide for targeted pseudouridylation, expressed as a pol-III expression construct, using a pol-III promoter such as U6 or H1. Such nucleic acid molecule may be provided as an expression construct, in a plasmid or viral vector, such as an AAV vector or the like.

The originally identified ('full length') H/ACA RNAs have a median length of 133 nucleotides forming an evolutionary conserved hairpin-hinge-hairpin-tail secondary structure that carries a consensus ANANNA sequence in the hinge region (H box) and an ACA triplet exactly three positions from the 3'-end (ACA box). Identification of target uridines is achieved by two 3-10 nucleotide-long antisense elements in the bulge of one or both hairpins (pseudouridylation pocket) directly 5' and 3' of the upper stem. These two elements hybridize to sequences immediately 5' and one nucleotide 3' of the target uridine thereby framing it. This positions the target uridine 14-15 nucleotides from the H or ACA box.

Many chemical modifications exist in the generation of (single stranded and/or antisense) recombinant oligonucleotides. In the search for improved properties, the inventors of the present invention found that a 2'-O-methyl (2'-OMe) modification of the ribose moiety of nucleotides is not only compatible with targeted pseudouridylation, but—surprisingly—leads to more efficient site-specific pseudouridylation of target mRNA molecules. Another surprising finding was that phosphorothioate (PS) inter-nucleoside linkages are also compatible with targeted pseudouridylation. Combinations of (non-natural) chemical modifications, such as the 2'-OMe ribose and the PS inter-nucleosidic linkages can also be used, without abolishing enzyme engagement or catalytic (pseudouridylation) activity. The present inventors have identified preferred sites. Whereas certain beneficial properties of 2'-OMe and PS and many more chemical modifications in antisense oligonucleotides and siRNAs are known as such, for example increased nuclease stability or other pharmacokinetic properties, the compatibility thereof with pseudouridylation, let alone the enhancing effect on catalysis, was unknown and could not have been predicted. Hence, in addition to having found ways to shorten these artificial guide RNAs, the present inventors have unravelled ways to chemically modify them to impose improved pharmacokinetic and pharmacodynamics properties. These and other advantages will become clear from the disclosure of the present invention.

The present invention relates to a nucleic acid molecule, capable of forming a double stranded complex with a target RNA molecule in a system (e.g. a cellular extract, a cell, a tissue or organ (e.g. on a chip), a living organism, preferably of mammalian origin), and capable of forming a functional (i.e. capable of pseudouridylation) RNA protein (RNP) complex, wherein the target RNA molecule comprises a target uridine for conversion into ψ, wherein the nucleic acid molecule is (a) shorter than (preferably about half the length or less of) a natural H/ACA snoRNA and/or (b) comprises a (non-natural) chemical modification of one or more nucleotides or inter-nucleosidic linkages. Such nucleic acid sequences according to the invention will also be referred to herein as 'pseudouridylating editing oligonucleotides', or 'psEONs' for short.

One preferred embodiment is a shortened version of an H/ACA snoRNA comprising only one hairpin structure with a guide loop (as opposed to two such hairpin structures typically found in natural H/ACA RNA structures and the artificial snoRNAs described in the art). Another preferred embodiment is a nucleic acid molecule that comprises at least one nucleotide carrying a 2'-OMe ribose modification and at least one PS inter-nucleoside linkage modification. Even more preferred are nucleic acid molecules that are shortened and have non-natural ribose and/or non-natural inter-nucleosidic linkage modifications.

psEONs according to the invention are preferably synthetic oligonucleotides. psEONs according to the invention are preferably oligoribonucleotides (full RNA), but may comprise DNA. Alternatively, especially when exclusively consisting of nucleotides or linkages that can be expressed in a biological system, psEONs may be expressed in situ, e.g. from a plasmid or a viral vector. In addition, psEONs may be a mix of biologically expressed components and synthetic components, such as tags or linkers. psEONs may be used as such ('naked'), or conjugated to other components, such as ligands for targeting, for uptake and/or for intracellular trafficking. psEONs may be used in aqueous solutions (generally pharmaceutically acceptable carriers and/or solvents), or formulated using transfection agents, liposomes or nanoparticulate forms (e.g. SNALPs, LNPs and the like). Such formulations may comprise functional ligands to enhance bioavailability and the like.

Among the rich variety of non-coding RNAs, small nucleolar RNAs are divided in two categories: the box C/D and the box H/ACA snoRNAs. Both contribute to the modification of ribosomal RNAs after transcription. Using endogenous RNP enzymes, synthetic oligonucleotides can potentially mimic the guiding H/ACA snoRNAs and bind to RNA targets allowing the conversion of uridine to ψ in a site-specific manner. In order to convert uridine to ψ in RNA targets, chemically modified oligonucleotides resembling H/ACA snoRNAs can—as shown herein for the first time—recruit endogenous RNP enzymes. To design such psEONs, it is described here how a combined approach based on experimental data, structural analysis and energy minimization of atomic scale models was adopted. The ACA19 RNA sequence length was minimized and functionality was checked with in vitro enzymatic assays (as described below). The structural analysis was based on information published by Li and Ye (2006, Nature 443:302-307). In the H/ACA box RNP from *Pyrococcus furiosus* (*P. furiosus*; an archaea species) only 3 proteins directly interact with the guide RNA, which adopts a stem-loop structure. These proteins are likely tRNA pseudouridine synthase B, the ribosome biogenesis protein Nop10 and the 50S ribosomal protein L7ae. The structure-based oligonucleotide design, as used in the present invention is divided in different parts: an overview of the hydrogen-bond network, a stepwise analysis of protein structures conservation in different archaea-eukaryotic organisms, the insertion of chemical modifications within the H/ACA box snoRNA (thereby monitoring potential steric clashes) and an energy minimization of atomic scale models including 2'-OMe and PS linkages.

Two categories of hydrogen-bonds are distinguished. The first group connects the oxygen-phosphate backbone of the RNA with the protein. The second group links the residues to the oligonucleotide bases. In general, these two sets of interactions are considered in the art as non-specific and specific, respectively. The crystal structure of an H/ACA box RNP from *P. furiosus* is the only structure of the RNA-bound pseudouridylation proteins assembly currently available in the art. A free structure of the Cbf5-Nop10-Gar1 complex from *Saccharomyces cerevisiae* (Li et al. 2011, Genes Dev 25:2409-2421) highlights important structural similarities regarding proteins arrangement for both systems. Superimpositions of the different H/ACA box RNP proteins structures were performed using TINKER's superpose routine (Pappu et al. 1998, J Phys Chem B 102:9725-9742). This conserved structural arrangement suggests that RNA binding may be supported by similar interactions. Although the transposition of structural requirements (for guide RNA attachment) from archaea to eukaryotic organisms is not trivial, the extrapolation of this analysis remains valuable with the support of primary sequence alignments, secondary and tertiary structures comparisons. In the crystal structure of an H/ACA box RNP, the guide RNA is mainly contacted by three proteins Cbf5, Nop10 and L7ae. Primary sequence alignment of these three proteins with their corresponding homologues from human, yeast and archaea indicated a high level of similarity (data not shown). Additionally, the secondary structures of all three proteins from yeast and archaea appeared comparable as found in the primary sequence alignment. Since the structural information of human Cbf5, Nop10 and Nhp2 (homolog to Archaeal L7ae) proteins were not available, their secondary structures were predicted using a protein secondary structure prediction server (JPred) and compared to the predicted secondary structures of yeast and archaeal corresponding proteins. The comparison revealed that all three proteins have very similar secondary structures. Additionally, the identified amino acid residues of all three proteins contacting the guide RNA in the H/ACA box RNP appeared very well conserved throughout their human and yeast homologs suggesting that all three proteins may recognize their guide RNA in a very similar manner.

In order to define the important anchoring points between the guide RNA and the proteins, the three-dimensional features of the bound RNA was investigated. Thus, independently from the primary sequence selected for the therapeutic RNA design, adopting a three-dimensional structure identical to the one shown for the archaea system is required. This statement is mainly valid for the common RNA parts covered by homologous proteins observed in both systems i.e. Cbf5 and Nop10. To extend the validity of the analysis, polypeptide chains equivalent to the L7ae protein of *P. furiosus* were identified in different eukaryotes (homologous proteins in yeast and human) Clearly, the direct transposition of the structural information from the archaeon to the yeast organism is somewhat speculative and local variations might occur. The density of specific contacts is higher in the vicinity of the ACA motif and at the junction between the upper stem and the smallest loop. This last element corresponds to the tetra-loop in yeast. Interestingly, the proposed secondary structure arrangement for the shortened ACA19 guide RNA does not fit with the three-dimensional features and constraints detected in the archaea H/ACA box RNP. However, the flexibility of the oligonucleotide appears as a crucial parameter for anchoring and the ACA19 guide RNA probably undergoes conformational adjustments to accommodate to the protein complex.

Figure 1:
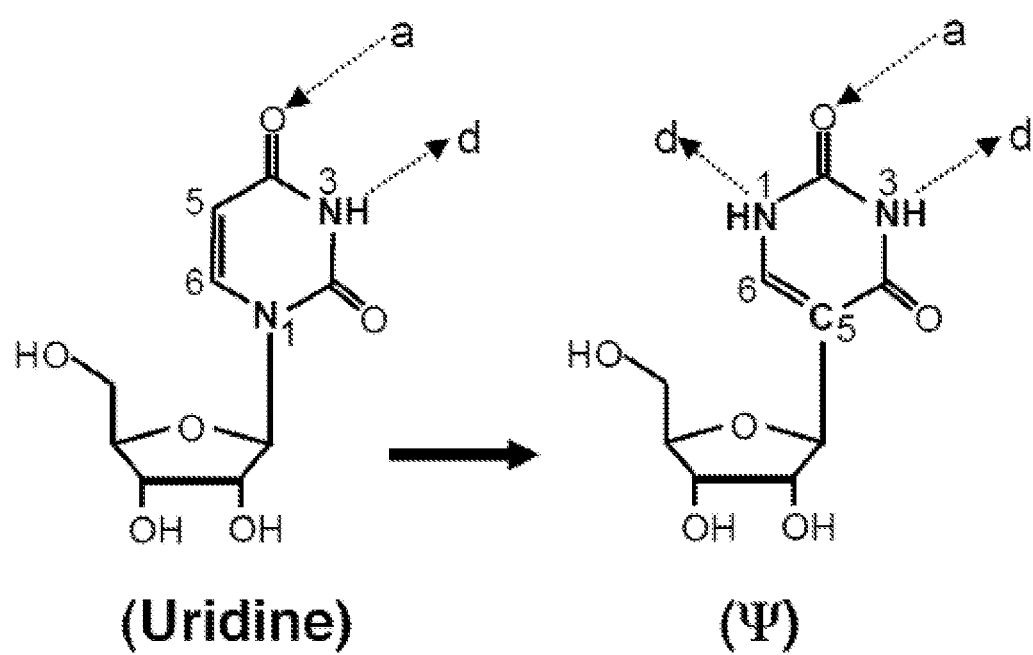
FIG. 1 shows the uridine and the pseudouridine (w) structure. The hydrogen bond acceptor (a) and hydrogen bond donor (d) sites are shown.
Figure 2:
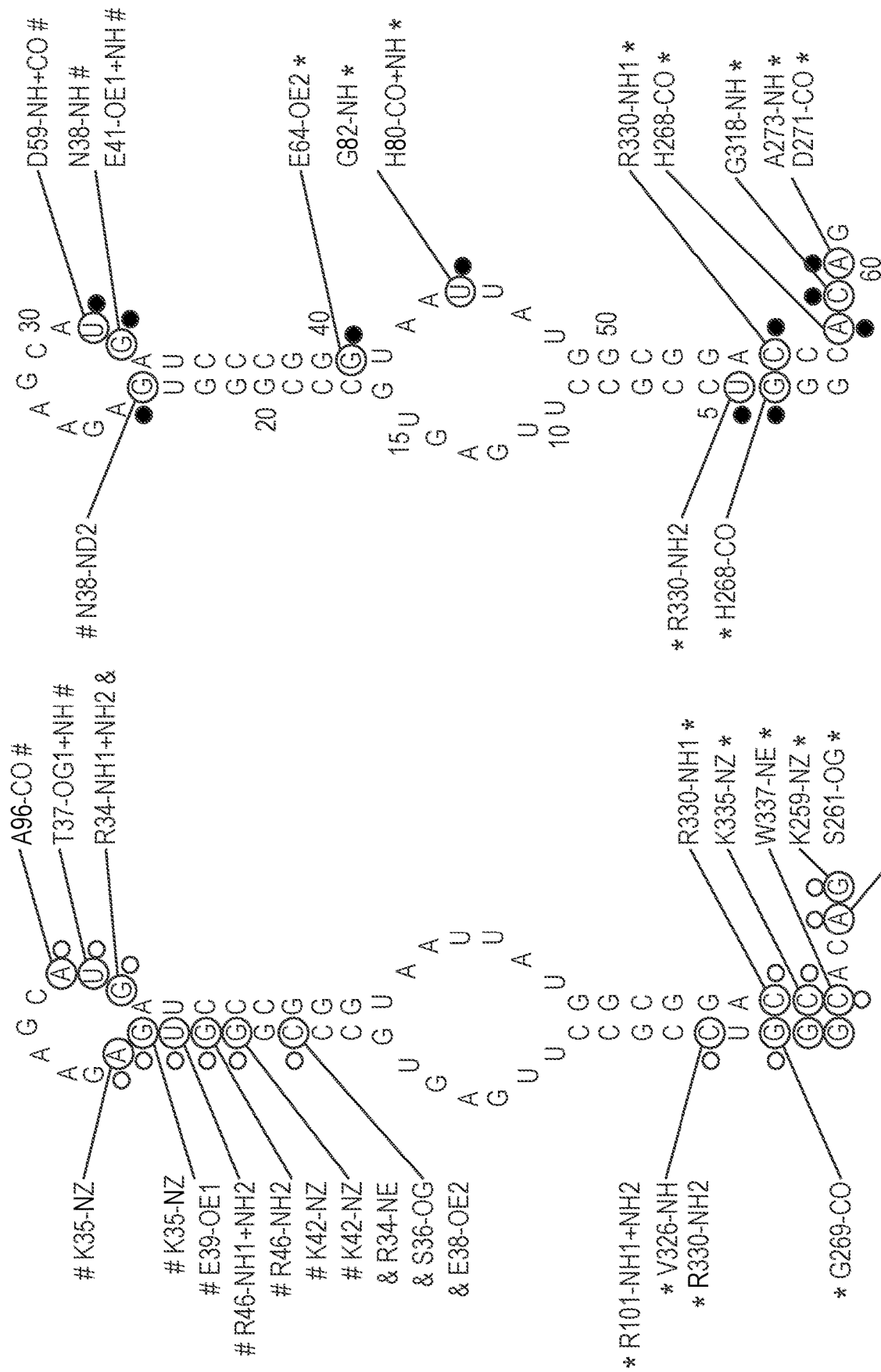
FIG. 2 shows the list of residues participating in the guide RNA attachment. Single-letter amino acid code is followed by the residue number reported in the H/ACA box RNP particle structure (PDB ID 2HVY). Atoms potentially involved in hydrogen bonds formation are indicated after the residue number. The amino-acids of the archaea species *Pyrococcus furiosus* (*P. furiosus*) H/ACA box RNP possessing the ability to generate hydrogen bond contacts with the RNA oxygen-phosphate backbone and bases are reported on the left and the right panel, respectively. Empty circles represent potential hydrogen bonds to the RNA sugar-phosphate backbone whereas filled circles indicate potential hydrogen bonds to the RNA bases. Residues belonging to the Cbf5 homologue protein, Nop10 and L7ae are indicated with asterisks, ampersands and hashes, respectively. The sequence of the human-derived guide region, as shown here in both left and right panel is: 5'-GGGUCCGCC-UUGAGUGCCCGGGUGAGAAGCAUGAUCCCGGGU AAUUAUGGCGGACCCACAG-3' (SEQ ID NO:4).

To support the structure-based oligonucleotide design and to facilitate the transfer of intermolecular hydrogen-bonds map to eukaryotes, the list of residues participating in the guide RNA attachment is shown in FIG. 2. The amino-acids of the archaea H/ACA box RNP interacting with the RNA oxygen-phosphate backbone and bases are reported on the left and the right panel, respectively. 70% of the contacts between bases and the protein involve the amide and carboxyl groups of the residues suggesting that a limited set of conserved residues may drive base recognition. However, the RNA backbone binding is mediated at 85% by the amino acid side chains. Remarkably, the Nop10 unit only interacts non-specifically with the guide oligonucleotide (hence, not with the bases). The analysis must take into account further primary sequence alignments between homologous proteins in different organisms. Some conserved residues may support nucleotide-protein contacts that are crucial for the therapeutic oligonucleotide function. In addition, predicted secondary structure elements may help to consider some potential variations in the local RNA conformation.

Figure 3:
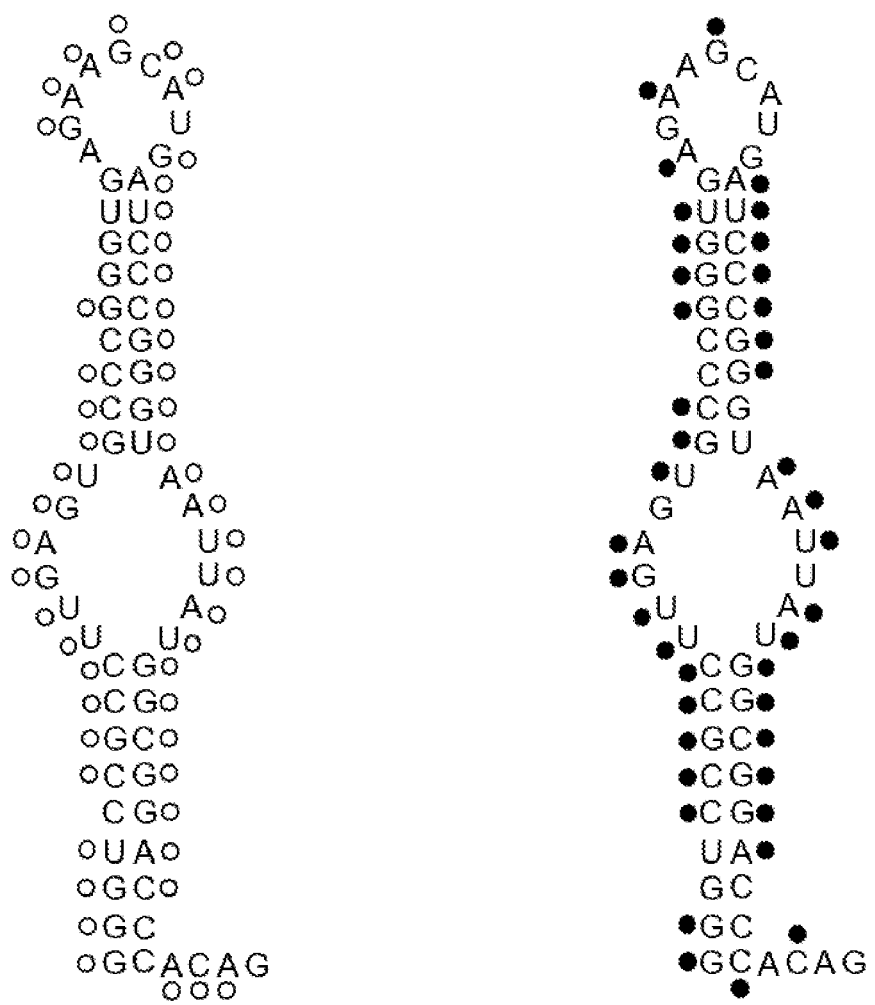
FIG. 3 shows the positions within the H/ACA *P. furiosus* snoRNA that were examined relative to the preservation of the hydrogen-bonds interaction network. The sequence is the same as in FIG. 2. Empty circles (left panel) and filled circles (right panel) specify the RNA backbone positions where PS linkages and 2'-OMe modifications are tolerated, respectively (without disrupting potential intermolecular connections). The open circles refer to the tolerated PS linkage on the 3' side of the nucleotide that is next to the circle.

The initial structural study paved the way for the implementation of relevant chemical modifications supporting oligonucleotide function in vivo. Classically, during the first stage of therapeutic oligonucleotide design, and this has been shown in the art, 2'-OMe modified sugar moieties and PS linkages contribute to improve resistance against RNAse activity, favour protein binding and facilitate uptake. However, it has never been suggested nor shown that such modifications could be used and would be compatible with protein engagement and catalytic activity in the context of pseudouridylating enzyme complexes. Following FIG. 3, the positions within the H/ACA *P. furiosus* RNA were examined relative to the preservation of the hydrogen-bonds interaction network. Chemical modifications for the H/ACA RNA model were introduced that were thought to participate in functionalizing the therapeutic oligonucleotides. The generation of atomic scale models by the insertion of chemical modifications within the archaeal stem-loop RNA was realized using the Avogadro software. The resulting H/ACA box RNP model was energy minimized with the Amber99 plus GBSA force-field as implemented in the TINKER package (Pappu et al. 1998). On the left panel of FIG. 3, the empty circles indicate where PS linkages are tolerated without disrupting the protein-RNA hydrogen-bonds network. On the right panel, the filled circles show positions where the insertion of 2'-OMe group should not interfere with RNA recognition (no steric hindrances). It should be noticed that intra-RNA hydrogen-bonds network may support the oligonucleotide stabilisation but was not considered for this evaluation.

The invention relates to a nucleic acid molecule for pseudouridylation of a target uridine in a target RNA in a mammalian cell, wherein the nucleic acid molecule comprises a guide region capable of forming a partially double stranded nucleic acid complex with the target RNA comprising the target uridine, wherein the partially double stranded nucleic acid complex is capable of engaging a mammalian pseudouridylation enzyme, wherein the guide region assists in positioning the target uridine in the partially double stranded nucleic acid complex for it to be converted to a pseudouridine by the mammalian pseudouridylation enzyme. The partially double stranded nucleic acid complex is preferably RNA/RNA. The RNA/RNA complex is able to recruit, or to get involved, a pseudouridylation enzyme that is preferably naturally present in the mammalian cell, but may be, in another embodiment, co-introduced with the nucleic acid molecule into the mammalian cell. Preferably the mammalian cell in which the pseudoruridylation takes place is a human cell. In a preferred aspect, the pseudouridylation enzyme is part of a ribonucleoprotein (RNP) complex capable of acting on an H/ACA-snoRNA. In a particularly preferred aspect, the nucleic acid molecule is shorter than a wild type H/ACA snoRNA and comprises one or more nucleosides and/or inter-nucleosidic linkages that are non-naturally modified compared to the wild type H/ACA snoRNA. Non-naturally means that the modification is in nature not present in a wild type snoRNA. The modification is preferably introduced to render the nucleic acid molecule more stable towards breakdown by RNAse enzymes. In a further preferred aspect, the nucleic acid molecule of the present invention comprises a single guide region corresponding to one of the two hairpin structures of the wild type H/ACA snoRNA, preferably the hairpin structure at the 3' terminal part of the wild type H/ACA snoRNA, more preferably wherein the 5' terminal nucleotide corresponds to a nucleotide from a region between the two hairpin structures of the wild type H/ACA snoRNA. The nucleic acid molecule according to the invention, and more preferably the nucleic acid that comprises a single guide region consists preferably of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. When the nucleic acid molecule according to the present invention comprises a non-natural modification, the non-natural modification comprises, in one embodiment, a modification in the ribose moiety, preferably wherein the 2'-OH of the sugar moiety is substituted. Particularly preferred modifications of the ribose moiety are 2'-OMe and/or 2'-MOE substitutions. The skilled person may apply a variety of modifications, depending of the efficiency in which the nucleic acid molecule of the present invention is able to give pseudouridylation in a particular cell and/or in the context of a particular pseudouridylation enzyme. In another aspect, the nucleic acid molecule comprises one or more non-natural inter-nucleosidic linkages, such as a phosphorothioate (PS) linkage.

The invention also relates to a nucleic acid molecule according to the invention, wherein the nucleic acid molecule is positioned in an intron sequence from which it is expressed, and wherein the intron sequence is located between an upstream exon A sequence and a downstream exon B sequence. The intron may comprise (besides the nucleic acid molecule of the present invention, comprising the guide region) additional nucleotides. Since the guide region is expressed from the intron sequence, such additional nucleotides may be selected to render the most efficient expression from the intron. Preferably, the exon A/intron/exon B sequence is present in a vector, preferably a plasmid or a viral vector. Such a vector can be used to deliver the exon-intron-exon sequence to the cell. Additional introns and exons may be present in such a vector. In a particularly preferred embodiment, the exon A sequence (upstream of the intron that carries the nucleic acid encoding the nucleic acid molecule (which is expressed after transcription)) comprises or consists of exon 1 of the human β-globin gene, and the exon B sequence (downstream of the intron that carries the nucleic acid encoding the nucleic acid molecule (which is expressed after transcription)) comprises or consists of exon 2 of the human β-globin gene. The skilled person knows that vectors may carry DNA or RNA, and are generally used to express the nucleic acid molecule of the present invention after the vector is processed in the cell in which it is introduced. Such is generally through transcription of the DNA or RNA present in the vector. Preferred vectors are viral vectors (that may be used to infect target cells to be treated), or plasmids, that may be introduced into the cell in a variety of ways, known to the person skilled in the art. In a preferred embodiment, the nucleic acid molecule that is positioned in the intron is a substantially full length pugU2-34/44 snoRNA. Substantially means that the snoRNA is active, even though one or more nucleotides may differ from the exact wild type pugU2-34/44 sequence. Using the teaching of the present disclosure, the skilled person can determine whether the substantially full length snoRNA is active in pseudouridylation. When the snoRNA is positioned in an intron, as disclosed herein, the nucleic acid molecule is preferably present in a vector, such as a plasmid, and wherein the nucleic acid molecule is transcribed from a CMV or a pol-III promoter, preferably a U6 or an H1 promoter. When the nucleic acid comprises a single guide region it may also be administered in a free form (or 'naked', without the context of a vector), or being delivered to a cell by other means, such as liposomes, or nanoparticles, or by using iontophoresis.

In a particularly preferred embodiment, the guide region present in the nucleic acid molecule of the present invention is capable of forming a partially double stranded (RNA/RNA) complex with the target RNA, which comprises a mutation that is associated with a genetic disorder. A non-limiting, but preferred example of such a mutation results in a Premature Termination Codon (PTC), wherein the PTC is the cause of the genetic disorder, and wherein the target uridine is in the PTC. Converting the target uridine in such a PTC to a pseudouridine, by using the means and methods of the present invention, then results in proper read-through of the reading frame during translation, thereby providing a (partly or fully) functional full length protein.

The nucleic acid molecule according to the invention is in one embodiment of the invention, for use in the treatment, prevention, delay or amelioration of Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, a Dystrophic Epidermolysis bullosa, an Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, a Leber congenital amaurosis, Lesch-Nyhan syndrome, Lynch syndrome, Marfan syndrome, Mucopolysaccharidosis, a Muscular Dystrophy, Myotonic dystrophy types I and II, neurofibromatosis, Niemann-Pick disease type A, B and C, NY-esol related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, a (autosomal dominant) Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, an Usher syndrome, X-linked immunodeficiency, Sturge-Weber Syndrome, or a cancer.

In yet another embodiment, the invention relates to a method for converting a uridine in a target RNA molecule into a pseudouridine, comprising the steps of contacting a target RNA comprising a target uridine with a nucleic acid molecule according to the invention in the presence of a pseudouridylation enzyme or RNP complex and allowing the uridine to be converted thereby, preferably wherein the pseudouridylation enzyme or RNP complex is present in a mammalian cell, preferably a human cell. In a preferred method according to the invention, the pseudouridylation enzyme or RNP complex is naturally present in the mammalian cell.

In yet another embodiment, the invention relates to a vector comprising an intron sequence that is located between an upstream exon A sequence and a downstream exon B sequence, wherein the exon A sequence and the exon B sequence are of a gene that is not the natural gene for the intron sequence, and wherein the intron sequence comprises a snoRNA sequence encoding a nucleic acid molecule comprising a guide region capable of forming a partially double stranded nucleic acid complex (RNA/RNA) with a target RNA comprising a target uridine, wherein the partially double stranded nucleic acid complex is capable of engaging a mammalian pseudouridylation enzyme to form a functional RNP complex, in a cell, wherein the guide region correctly positions the target uridine for it to be converted by the RNP complex, and wherein the target uridine is converted by the RNP complex to a pseudouridine. In a preferred vector, the snoRNA is a substantially a full length pugU2-34/44 snoRNA. Also preferred is a vector in which the exon A sequence comprises or consists of exon 1 of the human β-globin gene, and the exon B sequence comprises or consists of exon 2 of the human β-globin gene. Preferred vectors are plasmids and viral vectors. The vector according to the invention is preferably used for the treatment, prevention or amelioration of any one or more of the diseases listed herein.

The invention also relates to a pharmaceutical composition comprising a nucleic acid molecule according to the invention, or a vector according to the invention, and one or more of a pharmaceutically acceptable carrier, stabilizer or solvent. Suitable pharmaceutically acceptable carriers are well known to the person skilled in the art.

In yet another embodiment, the invention relates to a method for converting a uridine in a target RNA molecule into a pseudouridine in a cell, preferably a human cell, comprising the steps of: administering to the cell a vector according to the invention; allowing the transcription of the exon A/intron/exon B sequence; allowing splicing and the formation of the snoRNA positioned in the intron; and allowing the snoRNA to form a partially double stranded nucleic acid complex with the target RNA molecule, wherein the partially double stranded nucleic acid complex is capable of engaging a mammalian pseudouridylation enzyme to form a functional RNP complex, wherein the snoRNA correctly positions the target uridine for it to be converted by the RNP complex, and wherein the target uridine is converted by the RNP complex to a pseudouridine. The invention also relates to a mammalian cell comprising a nucleic acid molecule according to the invention or a vector according to the invention. In yet another embodiment, the invention relates to the use of a nucleic acid molecule of the invention in the manufacture of a medicament for the treatment of one or more of the diseases listed herein.

In one particular preferred, but non-limiting embodiment, the present invention relates to nucleic acid molecules according to the present invention for use in the treatment of cystic fibrosis (CF), and in an even further preferred embodiment, the present invention relates to nucleic acid molecules according to the invention for use in the treatment of CF wherein PTCs such as those listed in Table 1, and more preferably the G542X (UGA), W1282X (UGA), R553X (UGA), R1162X (UGA), Y122X (UAA), W1089X, W846X, and W401X mutations are modified through pseudouridylation to amino acid encoding codons, and thereby allowing the translation to full length proteins. It has for instance been well established in the art that ψAA and ψAG codons are both translated to serine or threonine, whereas a ψGA is translated to tyrosine or phenylalanine, instead of being seen as a stop codon (Karijolich and Yu, 2011). Hence, the pseudouridylation of PTCs to any of these ψ-containing codons will generate read-through during translation or in other words, suppress termination of the protein translation and/or the potential degradation of the mRNA by nonsense-mediated decay. Hence, in one preferred aspect, the present invention relates to a nucleic acid molecule according to the invention, such as a psEON as outlined herein, for use in the treatment of CF, wherein the nucleic acid molecule enables the conversion of a uridine present in a PTC present in the CFTR (pre-) mRNA to a ψ, and wherein the PTC results in early translation termination that eventually causes the disease. Hence, in another aspect the invention relates to a use of a nucleic acid molecule according to the invention in the manufacture of a medicament for the treatment or prevention of a disease, preferably CF. In yet another embodiment of the invention, it relates to a method for the pseudouridylation of at least one target uridine present in a PTC in a target RNA in a cell, the method comprising the steps of providing the cell with a nucleic acid molecule according to the invention; allowing uptake by the cell of the nucleic acid molecule (for instance while being carried by a delivery vector); allowing annealing of the nucleic acid molecule according to the invention to the target RNA; allowing a guide RNA-guided RNP to pseudouridylate the target uridine in the target RNA to a ψ; and optionally identifying the presence of the ψ in the targeted RNA, preferably wherein the last step comprises assessing the presence of a functional, elongated, full length and/or wild type protein when the target uridine is located in a PTC; assessing whether splicing of the pre-mRNA was altered by the pseudouridylation; or using a functional read-out, wherein the target RNA after the pseudouridylated target molecule encodes a functional, full length, elongated and/or wild type protein. Preferably, the cell in which pseudouridylation takes place, using methods and means of the present invention, is a human cell. In one preferred embodiment, the psEON according to the invention (especially when applied in a 'naked' form) comprises at least 50 nucleotides and is shorter than 100 nucleotides, more preferably shorter than 60 nucleotides.

As will be readily apparent to the skilled reader, the invention allows for different nucleic acid molecules according to the invention, designed for different target uridines in one and the same or different target RNAs targets, to be combined. Different nucleic acid molecules according to the invention may be used simultaneously in a single composition or in separate compositions, or consecutively. Nucleic acid molecules, such as psEONs according to the invention, may be combined with other forms of treatment, including other forms of oligonucleotide treatment. The examples provided herein serve to illustrate the invention and are by no means to be interpreted as limiting the invention in any way.

TABLE 1

List of PTC mutations in human CFTR that can be targeted for pseudouridylation using a nucleic acid molecule according to the present invention.

| Name of mutation | Mutation |
|---|---|
| G542X | G > T |
| W1282X | G > A |
| R553X | C > T |
| R1162X | C > T |
| Q493X | C > T |
| E60X | G > T |
| Y1092X | C > A |
| R1158X | C > T |
| Y122X | T > A |
| W1089X | G > A |
| R75X | C > T |
| W846X | G > A |
| E585X | G > T |
| Q220X | C > T |
| K710X | A > T |
| E822X | G > T |
| Q552X | C > T |
| E92X | G > T |
| Q39X | C > T |
| E831X | G > T |
| Q1313X | C > T |
| R709X | C > T |
| S466X | C > A |
| S489X | C > A |
| Q890X | C > T |
| R764X | C > T |
| S1196X | C > G |
| W401X | G > A |
| L732X | T > G |
| Q98X | C > T |
| R851X | C > T |

TABLE 1-continued

List of PTC mutations in human CFTR that can be targeted for pseudouridylation using a nucleic acid molecule according to the present invention.

| Name of mutation | Mutation |
|---|---|
| W1204X | G > A |
| G330X | G > T |
| E1104X | G > T |
| Q525X | C > T |
| R785X | C > T |
| R792X | C > T |
| S912X | C > A |
| C276X | C > A |
| Q414X | C > T |
| S1255X | C > A |
| Y849X | C > A |
| E1371X | G > T |
| Y913X | T > A |
| Q1412X | C > T |
| L1254X | T > G |
| E193X | G > T |
| S4X | C > A |
| G673X | G > T |
| G27X | G > T |
| W1098X | G > A |
| C524X | C > A |
| G550X | G > T |
| W57X | G > A |
| Q1411X | C > T |
| Q1382X | C > T |
| R1102X | A > T |
| Q685X | C > T |
| W496X | G > A |
| Q715X | C > T |
| L88X | T > A |
| W882X | G > A |
| Q1330X | C > T |
| Q2X | C > T |
| W19X | G > A |
| W216X | G > A |
| Y275X | C > G |
| Q720X | C > T |
| Q30X | C > T |

It is an important aspect of the invention that the psEON, while not being embedded in an intron sequence, comprises one or more nucleotides with one or more modifications of the sugar or nucleobase moieties, or one or more internucleotide linkages with modifications. Thereby, a single nucleotide of the psEON can have one, or more than one sugar or base modification.

Within the psEON, one or more nucleotide(s) can have such sugar or base modification(s), and one or more internucleotide linkage(s) can have modifications. As an example, the sugar modification may comprise a 2'-O-alkyl modification (such as a 2'-OMe modification), the base modification may involve replacing a cytidine base with a 5-methylcytidine, and the internucleotide linkage modification may involve replacing phosphodiester linkage with a (non-naturally occurring) PS linkage.

The psEONs of the present invention preferably comprise a single guide region, more preferably the guide region that is located at the 3' terminal part of a wt H/ACA snoRNA. It is therefore a preferred aspect of the invention that the psEON comprises a single hairpin structure (in contrast to the wild type situation wherein the snoRNA contains two hairpin structures), in which the hairpin structure in the psEON represents the hairpin at the 3' part of the wt H/ACA snoRNA, and wherein the 5'-end of the psEON starts at any position between the two stems found in the wt H/ACA snoRNA, and preferably comprises a few additional nucleotides not present in the stem structure. Preferably, in one aspect, the psEON of the present invention does not comprise a full H box at its 5'-end, but does comprise a wild type ACA box at its 3'-end. In another preferred aspect, it does comprise a full H box at the 5'-end, but lacks a full length ACA box at the 3'-end. This is in accordance with known interactions of the pseudouridine synthase, dyskerin, two of which bind to the natural H/ACA snoRNAs such that one binds the 5' hairpin and the H box, while the other binds the 3' hairpin and the ACA box.

An improved feature of the psEONs of the present invention is the use of specific nucleotide modifications at pre-defined spots to ensure stability as well as proper protein binding and pseudouridylation activity. These changes may vary and may include modifications in the backbone of the psEON, in the sugar moiety of the nucleotides as well as in the nucleobases. They may also be variably distributed throughout the sequence of the psEON, depending on the target and on secondary structures. Specific chemical modifications may be needed to support interactions of different amino acid residues within the RNA-binding domains. For example, PS linkages between nucleotides, and/or 2'-OMe modifications may be tolerated in some parts of the psEON, while in other parts they should be avoided so as not to disrupt crucial interactions of the enzyme with the phosphate and/or 2'-OH groups. The person skilled in the art will be—with the available knowledge from the art and based on the teaching of the present disclosure—capable of determining whether a certain position within the psEON is suitable for 2'-OMe modification and or whether a certain internucleoside linkage should or should not have a PS modification. The modifications should also be selected such that they prevent degradation of the psEONs. Specific nucleotide modifications may also be necessary to enhance the pseudouridylation activity on substrate RNAs where the target sequence is not optimal for editing.

The present invention, in one aspect, relates to pseudouridylating editing guide RNAs that can be delivered while being embedded in artificial introns that are flanked by exons of a specified and/or particularly selected gene. Through this, the guide RNA can be expressed in mammalian cells from a vector like a plasmid or a viral vector harbouring this exon-intron-exon sequence. As shown for the first time by the inventors of the present invention, it was possible to obtain targeted pseudouridylation in a sequence-specific manner using an intron-embedded guide RNA. This approach can now potentially be applied to promote, for instance, PTC suppression as a novel therapy in genetic diseases caused by PTC mutations.

The present invention is exemplified by, but not limited to, reversing the effect of nonsense stop mutations that usually lead to translation termination and mRNA degradation (via. Nonsense Mediated Decay, see below). In another aspect, targeted pseudouridylation can act as a means to recode uridine-containing codons as a mean to modulate protein function via amino acid substitution, for instance in crucial protein regions such as protein kinase active centres.

It is known from the art that naturally expressed pseudouridylation guide RNA sequences (box H/ACA snoRN As) in mammalian cells are often processed from pre-mRNA introns. The assembly process occurs by binding of several proteins with a function in the pseudouridylation into box H/ACA guide RNAs to form snRNPs. This process occurs during transcription and before splicing. After the guide RNA-containing intron is spliced out and de-branched, processing exonucleases degrade the intron at their 5' and 3' termini. However, the associated snRNP proteins protect the box H/ACA guide RNA sequences from degradation, allowing the formation of the mature snRNP complex. snoRNA sequences can be inserted in introns of a gene that is not (or may be) its natural environment, such as the human β-globin (Kiss and Filipowicz. 1995) while still leading to fully mature snRNPs. According to the present invention, pseudouridylating editing guide RNAs can be imbedded in non-host introns flanked by exons of genes. A non-limiting example of a human gene that serves this purpose is the β-globin gene. Such constructs can be administered to and expressed in a mammalian cell, for instance by using a plasmid or viral vector to express fully functional box H/ACA snoRNAs carrying in their pseudouridylation pocket a nucleotide sequence complementary to the target RNA region in a sequence specific way, in a therapeutic setting.

One of the consequences of mutations leading to PTCs in the coding sequence of a gene is the decrease of the mRNA levels. This is due to a mechanism known as the Nonsense-Mediated Decay (NMD), which is a cellular surveillance mechanism in mammals preventing transcripts that were not correctly processed to be translated. It is estimated that one-third of genetic disorders are a result of a mutation leading to a PTC (such as for instance in CF, retinitis pigmentosa (RP), and beta-thalassemia). In a normal scenario, exon-junction complexes (EJCs) are formed during splicing. Then, during the first translation round, ribosomes displace these EJCs. On the other hand, when a PTC is located more than 50-54 nucleotides upstream of the last EJC, the NMD pathway is triggered by formation of a termination complex consisting of EJC-associated NMD factors. When this happens during the first pioneer round of translation and the ribosomes co-exist with at least one EJC downstream their location, this triggers the de-capping and 5'-to-3' exonuclease activity and also de-adenylation of the tail and 3'-to-5' exonuclease-mediated transcript decay. In order to tackle the aforementioned genetic disorders, or any disorder that is due to a similar mutation, the inhibition of this pathway in a gene-specific and sequence-specific manner is therefore crucial. The present invention is exemplified by recoding a PTC, which results in an increase of snRNA levels, and in translational read-though of the recoded mRNA into a full-length protein. To assess NMD suppression, a known NMD-inhibition reporter assay (Zhang et al. 1998, RNA 4 (7):801-815) can be used, and translational read-through of a gene carrying a PTC can also be assessed. As exemplified herein, the human β-globin gene carrying a nonsense mutation at the $39^{th}$ codon in the exon 2 was used as the target sequence. Without correction, this nonsense mutation leads to a lower abundance of mRNA (as a result of NMD) as well as to a truncated protein. As shown herein, correction of the mutation via targeted pseudouridylation allows the full length protein to be translated from the mRNA and inhibits the NMD pathway, since mRNA levels are increased. The inventors of the present invention introduced a 131 nt pseudouridylating editing oligonucleotide sequence in the position of the original 130 nt intron 1-2 of the human β-globin gene, which is between exon 1 and exon 2. The intron-embedded guide RNA sequence has the splice donor site located upstream (directly downstream of exon 1), a branch site, a polypyrimidine tract (Py-rich region) and a splice acceptor located directly upstream of exon 2 (FIG. 12). The skilled person understands that the PTC region of the human β-globin construct can be exchanged by any other model or therapeutically-relevant target RNA of interest. As shown herein, serving purely as an example, the mmIDUA-W392X termination mutation was introduced in the $39^{th}$ codon of the human β-globin gene, serving as a target. It is shown that this PTC could be successfully pseudouridylated with an editing guide RNA embedded in an intron of a non-natural host gene, in a sequence-specific fashion. The targeted pseudouridylation resulted in an increase in mRNA levels (i.e. NMD inhibition) and synthesis of the full-length protein.

SnoRNAs, when embedded in an intronic sequence, can be applied for pseudouridylation in a cell after the exon-intron-exon sequence is administered to the cell. Such may be in the form of a naked nucleic acid. One other way by which such constructs (exon-intron-exon sequences) can be delivered to the cell (either in vitro, ex vivo or in vivo) is by using a delivery vehicle such as a viral vector. One preferred viral vector is based on Adeno-Associated Virus (AAV). Another preferred viral vector is for instance a retroviral vector such as a lentivirus vector and the like. Also, plasmids, artificial chromosomes, and plasmids usable for targeted homologous recombination and integration in the human genome of cells may be suitably applied for delivery of a snoRNA as defined herein.

Typically, when the snoRNA is delivered by a viral vector, it is in the form of an RNA transcript that comprises the sequence of an oligonucleotide according to the invention in a part of the transcript. An AAV vector according to the invention is a recombinant AAV vector and refers to an AAV vector comprising part of an AAV genome comprising an exon-intron-exon sequence according to the invention encapsidated in a protein shell of capsid protein derived from an AAV serotype. Part of an AAV genome may contain the inverted terminal repeats (ITR) derived from an adeno-associated virus serotype, such as AAV1, AAV2, AAV3, AAV4, AAV5, AAV6, AAV7, AAV8, AAV9 and others. Protein shell comprised of capsid protein may be derived from an AAV serotype such as AAV1, 2, 3, 4, 5, 6, 7, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV2 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention. Preferably, a recombinant AAV vector according to the invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector.

More preferably, a recombinant AAV vector according to the invention comprises a capsid protein shell of AAV serotype 2 and the AAV genome or ITRs present in said vector are derived from AAV serotype 5; such vector is referred to as an AAV 2/5 vector. More preferably, a recombinant AAV vector according to the invention comprises a capsid protein shell of AAV serotype 2 and the AAV genome or ITRs present in said vector are derived from AAV serotype 8; such vector is referred to as an AAV 2/8 vector. More preferably, a recombinant AAV vector according to the invention comprises a capsid protein shell of AAV serotype 2 and the AAV genome or ITRs present in said vector are derived from AAV serotype 9; such vector is referred to as an AAV 2/9 vector. More preferably, a recombinant AAV vector according to the invention comprises a capsid protein shell of AAV serotype 2 and the AAV genome or ITRs present in said vector are derived from AAV serotype 2; such vector is referred to as an AAV 2/2 vector. A nucleic acid molecule harboring an exon-intron-guide RNA-intron-exon sequence according to the invention represented by a nucleic acid sequence of choice is preferably inserted between the AAV genome or ITR sequences as identified above, for example an expression construct comprising an expression regulatory element operably linked to a coding sequence and a 3' termination sequence. "AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art. The AAV helper functions can be supplied on an AAV helper construct, which may be a plasmid.

Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand. "AAV helper virus" provides additional functions required for AAV replication and packaging.

Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456. Preferably, an AAV genome as present in a recombinant AAV vector according to the invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art. A preferred AAV vector according to the invention is an AAV vector, preferably an AAV2/5, AAV2/8, AAV2/9 or AAV2/2 vector.

Definitions of Terms as Used Herein

The terms 'adenine', 'guanine', 'cytosine', 'thymine', 'uracil' and 'hypoxanthine' (the nucleobase in inosine) as used herein refer to the nucleobases as such.

The terms 'adenosine', 'guanosine', 'cytidine', 'thymidine', 'uridine', 'pseudouridine' and 'inosine', refer to the nucleobases linked to the (deoxy)ribosyl sugar.

The term 'nucleoside' refers to the nucleobase linked to the (deoxy)ribosyl sugar.

The term 'nucleotide' refers to the respective nucleobase-(deoxy)ribosyl-phospholinker, as well as any chemical modifications of the ribose moiety or the phospho group. Thus the term would include a nucleotide including a locked ribosyl moiety (comprising a 2'-4' bridge, comprising a methylene group or any other group, well known in the art), a nucleotide including a linker comprising a phosphodiester, phosphotriester, phosphoro(di)thioate, methylphosphonates, phosphoramidate linkers, and the like.

Sometimes the terms adenosine and adenine, guanosine and guanine, cytosine and cytidine, uracil and uridine, thymine and thymidine, inosine and hypo-xanthine, are used interchangeably to refer to the corresponding nucleobase, nucleoside or nucleotide. Pseudouridine is often referred to as ψ, or as 5-ribosyluracil.

Sometimes the terms nucleobase, nucleoside and nucleotide are used interchangeably, unless the context clearly requires differently. The terms 'ribonucleoside' and 'deoxyribonucleoside', or 'ribose' and 'deoxyribose' are as used in the art.

Whenever reference is made to an 'oligonucleotide', both oligoribonucleotides and deoxyoligoribonucleotides are meant unless the context dictates otherwise. Whenever reference is made to an 'oligoribonucleotide' it may comprise the bases A, G, C, U or I. Whenever reference is made to a 'deoxyoligoribonucleotide' it may comprise the bases A, G, C, T or I. In a preferred aspect, the EON of the present invention is an oligoribonucleotide that may comprise chemical modifications, and may include deoxynucleotides (DNA) at certain specified positions.

Whenever reference is made to nucleotides in the oligonucleotide, such as cytosine, 5-methylcytosine, 5-hydroxymethylcytosine, Pyrrolocytidine, and β-D-Glucosyl-5-hydroxymethylcytosine are included; when reference is made to adenine, 2-aminopurine, 2,6-diaminopurine, 3-deazaadenosine, 7-deazaadenosine, 8-azidoadenosine, 8-methyladenosine, 7-aminomethyl-7-deazaguanosine, 7-deazaguanosine, N6-Methyladenine and 7-methyladenine are included; when reference is made to uracil, 5-methoxyuracil, 5-methyluracil, dihydrouracil, pseudouracil, and thienouracil, dihydrouracil, 4-thiouracil and 5-hydroxymethyluracil are included; when reference is made to guanosine, 7-methylguanosine, 8-aza-7-deazaguanosine, thienoguanosine and 1-methylguanosine are included.

Whenever reference is made to nucleosides or nucleotides, ribofuranose derivatives, such as 2'-desoxy, 2'-hydroxy, and 2'-O-substituted variants, such as 2'-O-methyl (2'-OMe), are included, as well as other modifications, including 2'-4' bridged variants. Whenever reference is made to oligonucleotides, linkages between two mono-nucleotides may be phosphodiester linkages as well as modifications thereof, including, phosphodiester, phosphotriester, phosphoro(di)thioate, methylphosphonate, phosphor-amidate linkers, and the like.

The term 'comprising' encompasses 'including' as well as 'consisting', e.g. a composition 'comprising X' may consist exclusively of X or may include something additional, e.g. X+Y.

The term 'about' in relation to a numerical value x is optional and means, e.g. x±10%.

The word 'substantially' does not exclude 'completely', e.g. a composition which is 'substantially free from Y' may be completely free from Y. Where relevant, the word 'substantially' may be omitted from the definition of the invention.

The term "complementary" as used herein refers to the fact that the nucleic acid molecule according to the invention hybridizes under physiological conditions to the target RNA sequence and/or to its own internal sequences, especially within the hairpin structure. The term does not mean that each and every nucleotide in the nucleic acid molecule has a perfect pairing with its opposite nucleotide in the target sequence or within the hairpin structure. In other words, while a nucleic acid molecule according to the invention may be complementary to a target sequence, there may be mismatches, wobbles and/or bulges between the nucleic acid molecule of the present invention and the target sequence, while under physiological conditions that nucleic acid molecule still hybridizes to the target sequence such that the cellular enzymes can convert the target uridine to a ψ. The term "substantially complementary" therefore also means that in spite of the presence of the mismatches, wobbles, and/or bulges, the nucleic acid molecule according to the present invention has enough matching nucleotides with the target sequence that under physiological conditions the nucleic acid molecule hybridizes to the target RNA. As shown herein, a nucleic acid molecule may be complementary, but may also comprise one or more mismatches, wobbles and/or bulges with the target sequence, as long as under physiological conditions the nucleic acid molecule of the present invention is able to hybridize to its target.

The term 'downstream' in relation to a nucleic acid sequence means further along the sequence in the 3' direction; the term 'upstream' means the converse. Thus in any sequence encoding a polypeptide, the start codon is upstream of the stop codon in the sense strand, but is downstream of the stop codon in the antisense strand.

References to 'hybridization' typically refer to specific hybridization, and exclude non-specific hybridization. Specific hybridization can occur under experimental conditions chosen, using techniques well known in the art, to ensure that the majority of stable interactions between probe and target are where the probe and target have at least 70%, preferably at least 80%, more preferably at least 90% sequence identity.

The term 'mismatch' is used herein to refer to opposing nucleotides in a double stranded RNA complex which do not form perfect base pairs according to the Watson-Crick base pairing rules. Mismatching nucleotides are G-A, C-A, U-C, A-A, G-G, C-C, U-U pairs. In some embodiments nucleic acid molecules according to the present invention comprise fewer than four mismatches, for example 0, 1 or 2 mismatches. Wobble base pairs are: G-U, I-U, I-A, and I-C base pairs.

The term 'splice mutation' relates to a mutation in a gene that encodes for a pre-mRNA, wherein the splicing machinery is dysfunctional in the sense that removal of introns from the pre-mRNA is disturbed and due to the aberrant splicing, for instance the translation of a fully functional protein is prevented, either by formation of a dysfunctional protein or by absence of the protein. Often such dysfunctional proteins are degraded rapidly and do not have any functional activity, as discussed herein, and the aberrantly spliced mRNAs may also be rapidly degraded. In a preferred aspect, the splice mutations that are targeted by the nucleic acid molecules of the present invention and through the methods of the present invention are present in the human CFTR gene. The skilled person is aware of methods to determine whether or not normal splicing is restored.

A free (or naked) psEON according to the present invention may be chemically modified almost in its entirety, for example by providing nucleotides with a 2'-O-methylated sugar moiety (2'-OMe) and/or with a 2'-O-methoxyethyl sugar moiety (2'-MOE).

Various chemistries and modification are known in the field of oligonucleotides that can be readily used in accordance with the invention. The regular internucleosidic linkages between the nucleotides may be altered by mono- or di-thioation of the phosphodiester bonds to yield phosphorothioate esters or phosphorodithioate esters, respectively. Other modifications of the internucleosidic linkages are possible, including amidation and peptide linkers. In a preferred aspect the psEONs of the present invention have one, two, three, four, five, six or more phosphorothioate linkages between the most terminal nucleotides of the psEON (hence, preferably at both the 5' and 3' end), which means that in the case of three phosphorothioate linkages, the ultimate four nucleotides are linked accordingly. It will be understood by the skilled person that the number of such linkages may vary on each end, depending on the target sequence, or based on other aspects, such as toxicity. However, it is an aspect of the invention that the psEON does comprise one or more PS linkages between any position at its terminal seven nucleotides.

The ribose sugar may be modified by substitution of the 2'-O moiety with a lower alkyl (C1-4, such as 2'-OMe), alkenyl (C2-4), alkynyl (C2-4), methoxyethyl (2'-methoxyethoxy; or 2'-O-methoxyethyl; or 2'-MOE), or other substituent. Preferred substituents of the 2' OH group are a methyl, methoxyethyl or 3,3'-dimethylallyl group. The latter is known for its property to inhibit nuclease sensitivity due to its bulkiness, while improving efficiency of hybridization. Alternatively, locked nucleic acid sequences (LNAs), comprising a 2'-4' intramolecular bridge (usually a methylene bridge between the 2' oxygen and 4' carbon) linkage inside the ribose ring, may be applied. Purine nucleobases and/or pyrimidine nucleobases may be modified to alter their properties, for example by amination or deamination of the heterocyclic rings. Other modifications that may be present in the psEONs of the present invention are 2'-F modified sugars, BNA and cEt. The exact chemistries and formats may depend from oligonucleotide construct to oligonucleotide construct and from application to application, and may be worked out in accordance with the wishes and preferences of those of skill in the art.

In a preferred aspect, the psEON of the present invention comprises 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleotides.

Examples of chemical modifications in the psEONs of the present invention are modifications of the sugar moiety, including by cross-linking substituents within the sugar (ribose) moiety (e.g. as in LNA or locked nucleic acids, BNA, cEt and the like), by substitution of the 2'-O atom with alkyl (e.g. 2'-O-methyl), alkynyl (2'-O-alkynyl), alkenyl (2'-O-alkenyl), alkoxyalkyl (e.g. 2'-O-methoxyethyl, 2'-MOE) groups, having a length as specified above, and the like. In the context of the present invention, a sugar 'modification' also comprises 2' deoxyribose (as in DNA). In addition, the phosphodiester group of the backbone may be modified by thioation, dithioation, amidation and the like to yield phosphorothioate, phosphorodithioate, phosphoramidate, etc., internucleosidic linkages. The internucleosidic linkages may be replaced in full or in part by peptidic linkages to yield in peptidonucleic acid sequences and the like. Alternatively, or in addition, the nucleobases may be modified by (de)amination, to yield inosine or 2' 6'-diaminopurines and the like. A further modification may be methylation of the C5 in the cytidine moiety of the nucleotide, to reduce potential immunogenic properties known to be associated with CpG sequences.

The degree of recruiting and redirecting the pseudouridylation entities resident in the cell may be regulated by the dosing and the dosing regimen of the snoRNA. This is something to be determined by the experimenter (in vitro) or the clinician, usually in phase I and/or II clinical trials.

The invention concerns the modification of target RNA sequences in eukaryotic, preferably metazoan, more preferably mammalian cells. In principle the invention can be used with cells from any mammalian species, but it is preferably used with a human cell. The invention can be used with cells from any organ e.g. skin, lung, heart, kidney, liver, pancreas, gut, muscle, gland, eye, brain, blood and the like. The invention is particularly suitable for modifying sequences in cells, tissues or organs implicated in a diseased state of a (human) subject, for instance when the human subject suffers from CF. Such cells include but are not limited to epithelial cells of the lung. The cell can be located in vitro or in vivo. One advantage of the invention is that it can be used with cells in situ in a living organism, but it can also be used with cells in culture. In some embodiments cells are treated ex vivo and are then introduced into a living organism (e.g. re-introduced into an organism from whom they were originally derived). The invention can also be used to edit target RNA sequences in cells within a so-called organoid. Organoids can be thought of as three-dimensional in vitro-derived tissues but are driven using specific conditions to generate individual, isolated tissues (e.g. see Lancaster and Knoblich. 2014, Science 345 (6194):1247125). In a therapeutic setting they are useful because they can be derived in vitro from a patient's cells, and the organoids can then be re-introduced to the patient as autologous material which is less likely to be rejected than a normal transplant. The cell to be treated will generally have a genetic mutation. The mutation may be heterozygous or homozygous. The invention will typically be used to modify point mutations.

The invention is used to make a change in a target RNA sequence in a eukaryotic cell through the use of an oligonucleotide that is capable of targeting a site to be edited and recruiting RNA editing entities resident in the cell to bring about the editing reaction(s). The target RNA sequence may comprise a mutation that one may wish to correct or alter, such as a point mutation (a transition or a transversion). The target RNA may be any cellular or viral RNA sequence, but is more usually a pre-mRNA or an mRNA with a protein coding function. The target sequence is endogenous to the eukaryotic, preferably mammalian, more preferably human cell.

The amount of nucleic acid to be administered, the dosage and the dosing regimen can vary from cell type to cell type, the disease to be treated, the target population, the mode of administration (e.g. systemic versus local), the severity of disease and the acceptable level of side activity, but these can and should be assessed by trial and error during in vitro research, in pre-clinical and clinical trials. The trials are particularly straightforward when the modified sequence leads to an easily-detected phenotypic change. It is possible that higher doses of nucleic acid could compete for binding to a nucleic acid editing entity within a cell, thereby depleting the amount of the entity which is free to take part in pseudouridylation, but routine dosing trials will reveal any such effects for a given nucleic acid molecule and a given target.

One suitable trial technique involves delivering the nucleic acid molecule according to the invention to cell extracts, cell lines, or a test organism and then taking biopsy samples at various time points thereafter. The sequence of the target RNA can be assessed in the biopsy sample and the proportion of cells having the modification can easily be followed. After this trial has been performed once then the knowledge can be retained and future delivery can be performed without needing to take biopsy samples. A method of the invention can thus include a step of identifying the presence of the desired change in the cell's target RNA sequence, thereby verifying that the target RNA sequence has been modified. The change may be assessed on the level of the protein (length, glycosylation, function or the like), or by some functional read-out, such as a(n) (inducible) current, when the protein encoded by the target RNA sequence is an ion channel, for example. In the case of CFTR function, an Ussing chamber assay or an NPD test in a mammal, including humans, are well known to a person skilled in the art to assess restoration or gain of function.

After pseudouridylation has occurred in a cell, the modified RNA can become diluted over time, for example due to cell division, limited half-life of the edited RNAs, etc. Thus, in practical therapeutic terms a method of the invention may involve repeated delivery of an oligonucleotide until enough target RNAs have been modified to provide a tangible benefit to the patient and/or to maintain the benefits over time.

Nucleic acid sequences (oligonucleotides, modified snoR-NAs; psEONs; vectors such as the ones described herein with exon-intron-exon sequences, pol-II, or pol-III driven expression constructs) of the invention are particularly suitable for therapeutic use, and so the invention provides a pharmaceutical composition comprising an oligonucleotide or carrier vector of the invention and a pharmaceutically acceptable carrier or solvent. In some embodiments of the invention the pharmaceutically acceptable carrier or solvent can simply be a saline solution. This can usefully be isotonic or hypotonic, particularly for pulmonary delivery. The invention also provides a delivery device (e.g. syringe, inhaler, nebuliser) which includes a pharmaceutical composition of the invention.

The invention also provides an oligonucleotide of the invention for use in a method for making a change in a target RNA sequence in a mammalian, preferably a human cell, as described herein. Similarly, the invention provides the use of a nucleic acid molecule, such as an oligonucleotide or expression construct or vector of the invention in the manufacture of a medicament for making a change in a target RNA sequence in a mammalian, preferably a human cell, as described herein.

The invention also relates to a method for the pseudouridylation of at least one specific target uridine present in a target RNA sequence in a cell, the method comprising the steps of: providing the cell with a nucleic acid molecule according to the invention; allowing uptake by the cell of the nucleic acid molecule (or the vector carrying a sequence encoding the nucleic acid molecule); allowing annealing of the nucleic acid molecule to the target RNA sequence; allowing the formation of a pseudouridylation-competent RNP with the introduced guide RNA incorporated, to pseudouridylate the target uridine in the target RNA sequence to ψ; and optionally identifying the presence of the ψ in the RNA sequence. The nucleic acid molecule (e.g. a psEON) may be manufactured and delivered as such, but it may also be, as disclosed herein, embedded in an intronic sequence, from which it is spliced out in the cell to become functional in pseudouridylation.

Introduction of the nucleic acid molecule according to the present invention into the cell is performed by general methods known to the person skilled in the art. After pseudouridylation, the read-out of the effect (alteration of the target RNA sequence) can be monitored through different ways. Hence, the identification step of whether the desired pseudouridylation of the target uridine has indeed taken place depends generally on the position of the target uridine in the target RNA sequence, and the effect that is incurred by the presence of the uridine (point mutation, PTC). Hence, in a preferred aspect, depending on the ultimate effect of U to ψ conversion, the identification step comprises: assessing the presence of a functional, elongated, full length and/or wild type protein; assessing whether splicing of the pre-mRNA was altered by the pseudouridylation; or using a functional read-out, wherein the target RNA after the pseudouridylation encodes a functional, full length, elongated and/or wild type protein. The functional assessment for each of the diseases mentioned herein will generally be according to methods known to the skilled person.

The nucleic acid molecule, such as an pseudouridylating editing oligonucleotide (psEON) expression construct or vector according to the invention is suitably administrated in aqueous solution, e.g. saline, or in suspension, optionally comprising additives, excipients and other ingredients, compatible with pharmaceutical use, at concentrations ranging from 1 ng/ml to 1 g/ml, preferably from 10 ng/ml to 500 mg/ml, more preferably from 100 ng/ml to 100 mg/ml. Dosage may suitably range from between about 1 μg/kg to about 100 mg/kg, preferably from about 10 μg/kg to about 10 mg/kg, more preferably from about 100 μg/kg to about 1 mg/kg. Administration may be by inhalation (e.g. through nebulization), intranasally, orally, by injection or infusion, intravenously, subcutaneously, intra-dermally, intra-cranially, intravitreally, intramuscularly, intra-tracheally, intra-peritoneally, intra-rectally, and the like. Administration may be in solid form, in the form of a powder, a pill, or in any other form compatible with pharmaceutical use in humans. The invention is particularly suitable for treating genetic diseases, such as CF.

In some embodiments the nucleic acid molecule, such as a psEON, expression construct or vector can be delivered systemically, but it is more typical to deliver an oligonucleotide to cells in which the target sequence's phenotype is seen. For instance, mutations in CFTR cause CF which is primarily seen in lung epithelial tissue, so with a CFTR target sequence it is preferred to deliver the oligonucleotide construct specifically and directly to the lungs. This can be conveniently achieved by inhalation e.g. of a powder or aerosol, typically via the use of a nebuliser. Especially preferred are nebulizers that use a so-called vibrating mesh, including the PARI eFlow (Rapid) or the i-neb from Respironics. It is to be expected that inhaled delivery of oligonucleotide constructs according to the invention can also target these cells efficiently, which in the case of CFTR gene targeting could lead to amelioration of gastrointestinal symptoms also associated with CF. In some diseases the mucus layer shows an increased thickness, leading to a decreased absorption of medicines via the lung. One such disease is chronical bronchitis, another example is CF. A variety of mucus normalizers are available, such as DNases, hypertonic saline or mannitol, which is commercially available under the name of Bronchitol. When mucus normalizers are used in combination with pseudouridylating oligonucleotide constructs, such as the psEON constructs according to the invention, they might increase the effectiveness of those medicines. Accordingly, administration of an oligonucleotide construct according to the invention to a subject, preferably a human subject is preferably combined with mucus normalizers, preferably those mucus normalizers described herein. In addition, administration of the oligonucleotide constructs according to the invention can be combined with administration of small molecule for treatment of CF, such as potentiator compounds for example Kalydeco (ivacaftor; VX-770), or corrector compounds, for example VX-809 (lumacaftor) and/or VX-661. Alternatively, or in combination with the mucus normalizers, delivery in mucus penetrating particles or nanoparticles can be applied for efficient delivery of pseudouridylating molecules to epithelial cells of for example lung and intestine. Accordingly, administration of an oligonucleotide construct according to the invention to a subject, preferably a human subject, preferably uses delivery in mucus penetrating particles or nanoparticles. Chronic and acute lung infections are often present in patients with diseases such as cystic fibrosis. Antibiotic treatments reduce bacterial infections and the symptoms of those such as mucus thickening and/or biofilm formation. The use of antibiotics in combination with oligonucleotide constructs according to the invention could increase effectiveness of the pseudouridylation due to easier access of the target cells for the oligonucleotide construct. Accordingly, administration of an oligonucleotide construct according to the invention to a subject, preferably a human subject, is preferably combined with antibiotic treatment to reduce bacterial infections and the symptoms of those such as mucus thickening and/or biofilm formation. The antibiotics can be administered systemically or locally or both. For application in CF patients the oligonucleotide constructs according to the invention, or packaged or complexed oligonucleotide constructs according to the invention may be combined with any mucus normalizer such as a DNase, mannitol, hypertonic saline and/or antibiotics and/or a small molecule for treatment of CF, such as potentiator compounds for example ivacaftor, or corrector compounds, for example lumacaftor and/or VX-661. To increase access to the target cells, Broncheo-Alveolar Lavage (BAL) could be applied to clean the lungs before administration of the oligonucleotide according to the invention.

EXAMPLES

Example 1: Design of Pseudouridylating Guide Oligonucleotides Derived From the Structure of Small Nucleolar RNA (snoRNA) for the Conversion of a Specific Uridine in ACA19 Target RNA to ψ

Figure 4:
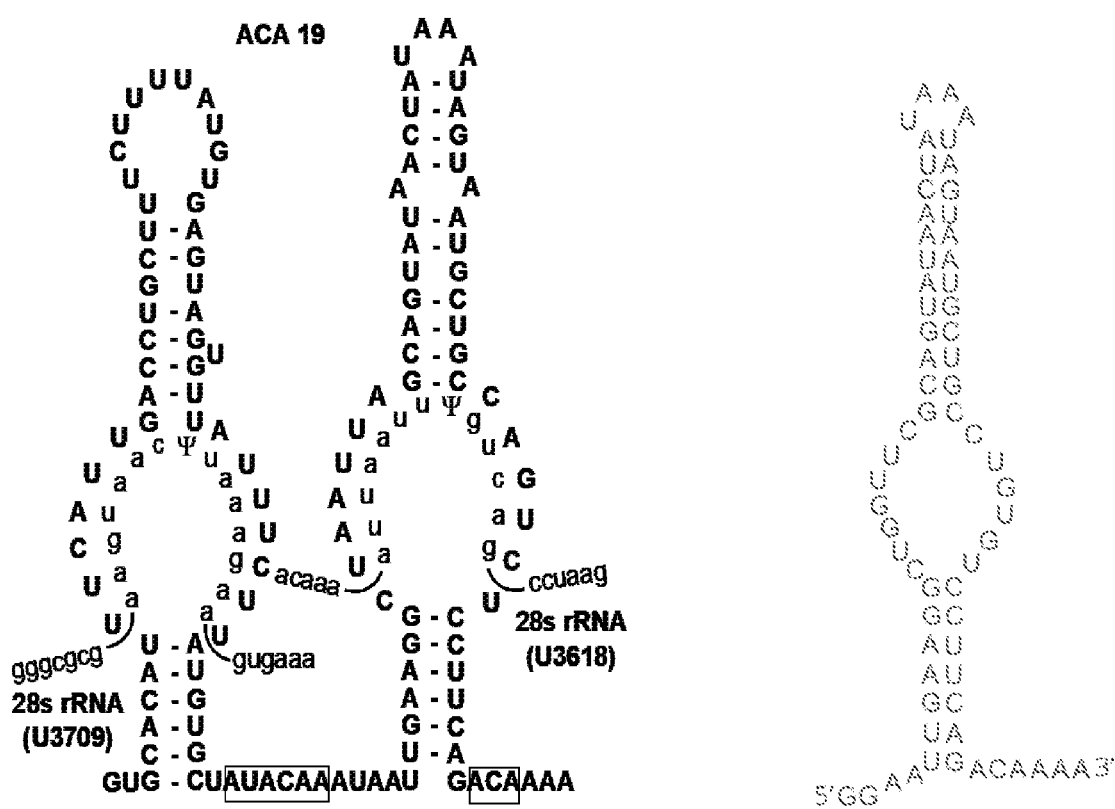
FIG. 4 shows the basic structure of human H/ACA ACA19 snoRNA (A) bound to its natural target sequences in the 28S rRNA, with the target nucleotide shown in its pseudouridylated form (Ψ). The snoRNA comprises two hairpin structures within which the internal target-binding loops are located, as well as the H box between the hairpins and the ACA box at the 3'-end. The sequence of this full length wild type ACA19 snoRNA with the H-box underlined (boxed in the figure) and the ACA box in bold (also boxed in the figure) is: 5'-GUGCACAUUUCAUUGACCUGC-UUUCUUUUAUGUGAGUAGUGUUAUUUCUUAUGU GCU<u>AUACAAA</u>UAAUUGAAGGCUAAUUAGC-

The inventors of the present invention questioned whether it would be possible to induce pseudouridylation using a shortened box H/ACA snoRNA. For this, a pseudouridylation guide RNA was designed in which the 5' hairpin of the full-length ACA19 snoRNA, and most of the H box were removed (FIG. 4). The shortened guide RNA and the full-length snoRNA were produced by in vitro transcription using T7 RNA polymerase. For testing in cell lysates, a short substrate RNA for these guides was produced either by in vitro transcription using T7 RNA polymerase (in the presence of [α-$^{32}$P]UTP) or by two-piece ligation. For the latter, first, a synthetic RNA oligonucleotide, terminating at its 5' end in the uridine to be pseudouridylated, was radioactively labelled at the 5' hydroxyl group with a [γ-$^{32}$P] phosphate using T4 polynucleotide kinase. The radioactively labelled RNA oligonucleotide was then ligated at its 5' end to the 3' hydroxyl group of another RNA oligonucleotide to form the substrate RNA. This was done by annealing the RNA oligonucleotides with a 30-nt bridging DNA oligonucleotide, such that the 5' half (15 nt) of the bridging DNA oligo base-paired with the 3' RNA fragment and the 3' half (15-nt) of the bridging DNA oligo base-paired with the 5' RNA fragment, and then providing them with T4 DNA ligase to covalently link the RNA oligonucleotides. The ligated, radioactively labelled RNA substrate then has the sequence of 5'-AGGGGAACCCCACAGUCGAACCAAAACAAA-3' (SEQ ID NO:1), in which the target uridine (containing the radioactive phosphate on its 5' side) is underlined. This substrate RNA was then purified from the other nucleic acids by separating it, cutting it from a denaturing polyacrylamide gel, eluting it from the gel and finally concentrating it by ethanol precipitation. For preparing the cell lysate for testing the pseudouridylation, HeLa cells were grown on standard 10-cm cell culture dishes in DMEM with 10% FBS to a confluency of 80-100%, after which they were collected by scraping, and washed with phosphate buffered saline. Thereafter, 200 μl extraction buffer (25% glycerol, 0.42 M NaCl, 1.5 mM MgCl$_2$, 0.2 mM EDTA, 20 mM HEPES (pH 7.9), 0.5 mM DTT and 0.5 mM Phenylmethane-sulfonyl Fluoride) was added on the cells, which were then vortexed in the presence of sterile glass beads for 30 sec three times, each time followed by a 30 sec incubation on ice. The cell debris was removed by centrifugation, and the supernatant was collected for use in the pseudouridylation assay.

For pseudouridylation assays, incubation buffer containing 200 mM Tris-HCl, pH 8.0, 200 mM ammonium acetate, 10 mM MgCl$_2$, 4 mM DTT, and 0.2 mM EDTA, as supplemented with 200 ng of the full-length H/ACA snoRNA or the shortened guide RNA, substrate RNA according to its relative radioactivity (5000 counts per minute), 250 ng yeast tRNA, and HeLa cell extract (final concentration 20%) were mixed and incubated at 37° C. for 40 min. RNA was then isolated from the reactions by phenol-chloroform extraction and ethanol precipitation. The RNA was then incubated with P1 nuclease (~300 ng) in 20 mM sodium acetate buffer, pH 5.2 for 1 h at 37° C. to degrade the RNA and release the individual nucleotides. These were then separated by thin-layer chromatography (with the solvent volume ratios 70:15:15 for isopropyl alcohol:HCl:water respectively), and the radioactive nucleotides were then imaged by autoradiography. Due to the different migration of the labelled uridines and pseudouridines derived, the conversion of the labelled substrate uridine into pseudouridine can be clearly observed with both the full-length H/ACA snoRNA and the shortened guide RNA. FIG. 5 shows that when a shortened pseudouridylating guide oligonucleotide is used, the efficiency of pseudouridylation is at least comparable to what is seen with the full length versions of the guide RNAs.

Then, it was investigated whether chemical modifications made in the shortened ACA19 guide RNA would be compatible with the target RNA engagement, and the formation of a catalytically active pseudouridylation complex. The positions of the chemical modifications were selected as described herein. The substrate RNA and the experimental assays used were the same as for the above comparison of the full-length H/ACA snoRNA or the shortened guide RNA. FIG. 6 shows the four ACA19 pseudouridylating editing oligonucleotides (psEONs) and the positions of the chemical modifications that were introduced: black dots indicate 2'-OMe modifications on the ribose moiety of that nucleotide, and open dots indicate PS modification of the linkage between the two riboses. FIG. 7 shows the result of pseudouridylation using the four ACA19 psEONs in parallel with the corresponding guide RNA (lacking chemical modifications) as a positive control and no guide RNA as a negative control. U and Ψ indicate the migration of uridine and pseudouridine in the thin layer chromatography, respectively. Clearly, the chemically modified psEONs were able to support conversion of uridine to pseudouridine, and the first psEON even gives a much stronger pseudouridylation signal in comparison to the positive control. The enhanced effect could be due to specific interactions of the chemical modifications of the psEON within the enzymatically active complex, or due to other effects, such as increased resistance to nucleases in the cell lysates, each of which can contribute to the pseudouridylation efficiency and/or rate.

Example 2: Design of psEONs for the Conversion of a Specific Uridine in a Premature Termination Codon in Human CFTR It was investigated whether a uridine in a premature termination codon (PTC) in the human CFTR gene could be converted to ψ. As an example the CFTR-G542X mutation was selected. Procedures to test this were as described in example 1.

The substrate RNA was constructed similarly as in example 1 (two-piece ligation), with the final target sequence being 5'-GACAAUAUAGUUCUUUGAGAAG-GUGGAAUC-3' (labelled target uridine underlined; SEQ ID NO:2).

FIG. 8 shows the four CFTR-G542X psEONs and the positions of the chemical modifications that were introduced: black dots indicate 2'-OMe modifications on the ribose moiety of that nucleotide, and open dots indicate PS modification of the linkage between the two riboses. FIG. 9 shows the result of pseudouridylation using the four CFTR-G542X psEONs in parallel with the corresponding guide RNA (lacking chemical modifications) as a positive control and no guide RNA as a negative control. U and Ψ indicate the migration of uridine and pseudouridine in the thin layer chromatography, respectively. The results clearly indicate that three out of four psEONs outperform the positive control, once again showing that chemical modifications at the indicated positions increase the rate and/or efficiency of pseudouridylation in mammalian cell lysates.

Example 3: Design of snoRNAs for the Conversion of a Specific Uridine in a Premature Termination Codon in Mouse Idua RNA It was investigated whether a uridine in a PTC in the mouse Idua RNA could be converted to ψ. As an example the Idua-W392X mutation in the mouse RNA was selected, which corresponds to the human IDUA W402X mutation known to cause Hurler syndrome. For this, the substrate RNA was constructed similarly as in Example 1 (two-piece ligation), with the final sequence of 5'-GAUG-GAGAACAACUCUAGGCAGAGGUCUCA-3' (labelled target uridine underlined; SEQ ID NO:3).

FIG. 10 shows the four Idua-W392X psEONs and the positions of the chemical modifications that were introduced: black dots indicate 2'-OMe modifications on the ribose moiety of that nucleotide, and open dots indicate PS modification of the linkage between the two riboses. FIG. 11 shows the result of pseudouridylation using the four Idua-W392X psEONs in parallel with the corresponding guide RNA (lacking chemical modifications) as a positive control and no guide RNA as a negative control. U and Ψ indicate the migration of uridine and pseudouridine in the thin layer chromatography, respectively. Here, the intensity of the negative control is very low due to loss of the sample during the precipitation step after the pseudouridylation reaction. Nonetheless, the results clearly indicate that all of the psEONs are capable of supporting the conversion of a uridine to pseudouridine, and even outperform the positive control, once again showing that chemical modifications at the indicated positions increase the rate and/or efficiency of pseudouridylation in mammalian cell lysates.

Example 4: Targeted Pseudouridylation of a Premature Termination Codon-Containing Vector Using Intronic-Embedded Guide RNAs Cloning of the Exon1/Intron-Guide RNA Intron/Exon2 Constructs "pugIntron-IDUA" and "pugIntronOpt-IDUA"

The pugIntron-IDUA plasmid construct was based on the original backbone pdR.Luc-G1 (Woeller et al. 2008. EMBO Reports 9 (5):446-451) and was generated by PCR amplification and site-directed mutagenesis, using Agilent's PfuUltra II fusion HS DNA polymerase. The pugIntron plasmid was generated by first inserting restriction sites SalI and PstI into the first intron of human β-globin in the parental pdRLuc-G1 vector. The following primers were used: SDM1-GLintron1-Sal-Pst: 5'-GTAAGTCGACGAAT-TCTGCAGGCTGCTGGTGG-3' (SEQ ID NO:13) and SDM2-GLintron1-Sal-Pst: 5'-GCCTGCAGAAT-TCGTCGACTTACCTGCCCAGG-3' (SEQ ID NO:14). Then, the guide RNA was generated by PCR using the following SalI/PstI containing primers (an extra Py-rich sequence for splicing was also included): pug-intron-Fwd-SalI: 5'-GTTGTCGAC GTGGGAGATTCT-3' (SEQ ID NO:15) and pug-intron-RevExPstI: 5'-AATCTGCAGG GGAAAAGAGAGAGTCAACCTGTCTGCCTCGT-3' (SEQ ID NO:16). First, using a HindIII site located downstream the PstI restriction site, but still in the intronic region, the SalI-HindIII fragment of the parental vector was pasted into an intermediate vector (pEGFP-C3). The guide RNA PCR product digested with SalI-PstI was then inserted into this intermediate vector. Finally, the SalI-HindIII fragment was cloned back into the pugIntron expression parental vector. FIG. 12A shows the construct with the upstream CMV promoter, exon 1 (E1) and exon 2 (E2) and the pugIntron-IDUA insert in the intronic part, with the SalI and PstI sites indicated. FIG. 13 shows the sequence of the entire pugIntron-IDUA plasmid (SEQ ID NO:11). A further optimized version of this construct (creating a more suitable 3' splice site sequence) was made by running a PCR using the pug-intron-FwdSalI as the forward primer (see above) and the following primer as the reverse primer (the additional two nucleotides in comparison to the pug-intron-RevExPstI reverse primer, see above, creating an additional 5"-AC-3' sequence at the 3' splice site, are underlined): pug-intronOPT-RevExPstI: 5'-AATCTGCAGGG-GAAAAGAGAGAGTCAGTACCTGTCTGCCTC-3' (SEQ ID NO:21). The cloning steps as indicated above were repeated to generate the optimized plasmid pugIntronOpt-IDUA, for which the full sequence is given in SEQ ID NO:22 (comprising the additional 5'-AC-3' directly downstream of the intron, in comparison to SEQ ID NO:11). The negative control pugCFTR was the original version of the guide RNA which was used for the PCR template of the pugIntron. This construct was made from three overlapping DNA oligos, of which backbone is originated from pugU2-34/44, for CFTR: pug-NBD1-F1HindIII 5'-AT-TAAGCTTGT GTGGGAGAT-TCTTCTTCGGACAGAGAGAAACTCTGCTGTG-3' (SEQ ID NO:27), pug-NBD1-R1 5'-CTGCTGTGTCT-GAAAGAAGATCTCCCTATAGTGACCCTGCCT-TACCTTCTCCGGGAC GAA-3' (SEQ ID NO:28) and pug-NBD1-R2BamHI 5'-ATGGATCCACCTGTCTGCC TCGTATTCTTCCGTTACGATTTCTCTCAT-TTCGTCCCGG-3' (SEQ ID NO:29), and for IDUA: pug-mmidua-F1HindIII 5'-ATTAAGCTTGTGTGGGAGAT-TCTGCCTCGGACAGAGAGAAACTCT GCTGTG-3' (SEQ ID NO:30), pug-mmidua-R1 5'-TTCGTCCCGGGGCAGAGAAGGCAGG GTCAC-TATAGGGAGATCAACTCTCAGACACAGCAG-3' (SEQ ID NO:31) and pug-mmidua-R2B amHI 5'-ATGGATC-CACCTGTCTGCCTCgtaAACTCCCGTTACGAT-TTCTCTCATTTC GTCCCGG-3' (SEQ ID NO:32). Then, the 3 piece-PCR products were digested with HindIII and BamHI and cloned into pcDNA3.1/Zeo(+).

Cloning of the Target Plasmid "GL-IDUA Swap" Comprising the Human β-Globin Gene Harbouring a mmIDUA-W392X PTC Mutation As target sequence for pseudouridylation the construct expressing the human β-globin gene was used (WT and TER; Woeller et al. 2008). In the TER version of the plasmid, which contains a PTC in globin codon 39, the target sequence (being the substrate for the guide RNA) was swapped by the CFTR-G542X mutation (serving as a negative control target plasmid) and the mmIDUA-W392X mutation (target for the pugIntron-IDUA plasmid) by site-directed mutagenesis using the PfuUltra II fusion HS DNA polymerase according to the manufacturer's protocols (Agilent technologies). In order to swap the 33 nt nonsense region (position −15 to PTC (3 nt) to position +15) in the original pFLAG2CMV2-HBB construct with the 33 nt mmIDUA-W392X target sequence (marked in hold in FIG. 14), the following primers were used for amplification: SDM-GL39-SWAPto-mmidua-1: 5'-TGGTGGATG-GAGAACAACTCTAGGCAGAGGTCTCAAAGTT TGGGGATCTGTCCACTCC-3' (SEQ ID NO:17) and SDM-GL39-SWAPto-mmidua-2: 5'-CCAAACTTTGA-GACCTCTGCCTAGAGTTGTT CTCCATC-CACCAGCAGCCTAAGGGTGG-3' (SEQ ID NO:18). For the generation of the CFTR-G542X mutation containing swapped plasmid (GL-CFTR swap) the following primers were used: SDM-GL39-SWAPto-NBD1-1 5'-TGGTGGACAATATAGTTCTTTGAGAAGGTGGAAT-CACATTTGGGGATCTGTCCACTC C-3' (SEQ ID NO:33) and SDM-GL39-SWAPto-NBD1-2 5'-CCAAATGTGATTCCACCTTCTC AAAGAACTATAT-TGTCCACCAGCAGCCTAAGGGTGG-3' (SEQ ID NO:34).

Cell Culture and Transfection Protocol

HEK293T and HeLa cells were cultured in DMEM+10% FBS. Transient transfections were performed using polyethylenimine HCl PEI MAX 40000 (PolySciences) as a stock solution of 1 mg/mL (pH7). Cells were grown in 6-well dishes up a high confluency (90-100%). To prepare the transfection solution, 150 μL of Opti-MEM (serum-free) was mixed with 9 μL of PEI stock solution and the resulting mixture was incubated at RT for 5 min. Following this, 100 ng substrate plasmid DNA (wild-type or PTC-containing) and 2 μg guide RNA-expressing plasmid DNA was added to the aforementioned PEI/medium mix. The resulting solution was incubated at RT for 15 min after which the mixture was added directly to each well.

RT-PCR

HEK293T cells were transfected with GL39-IDUA swap substrate plasmid with or without pugIntronOpt-IDUA guide expressing plasmid as given above. Total RNA was isolated using the TRIzol™ Reagent (Invitrogen). Reverse transcription was carried out with AMV Reverse Transcriptase (Promega) and the RT product was then amplified by PCR with GoTaq® Green Master Mix (Promega), using 15 to 23 cycles. The target mRNAs for pseudouridylation were detected using RT-PCR with the following primer pair: Forward primer: RLuc-Gl ex1 S4: 5'-TCTGCCGT-TACTGCCCTGTG-3' (SEQ ID NO:19) and Reverse primer: PE-mmiduaPTC+16: 5'-CTTTGAGACCTCTGCC-3' (SEQ ID NO:20). 5S rRNA was detected for normalization purposes with the following primer pair: 5SFwd: 5'-GC-CATACCACCCTGAACG-3' (SEQ ID NO:23) and 5SRev: 5'-AGCTTCCGAGAT CAGACGAG-3' (SEQ ID NO:24). RT-PCR products were separated by gel electrophoresis and quantified by Image Studio Lite (LI-COR). Results are given in FIG. 15 and show that when the pugIntronOpt-IDUA plasmid (here pugIntOptIDUA) was transfected with the target plasmid GL39-IDUA swap (here GL39IDUA) in HEK293T cells, a RT-PCR product using the primers given above could be detected (given by arrow GL39) after 18 cycles but not yet after 15 cycles. Almost no product could be detected when the GL39-IDUA swap plasmid was transfected without intron-carried guide RNA expressing plasmid. This indicates that the amount of mRNA from the GL39-IDUA swap plasmid was higher in these cells than when no guide RNA was introduced. Indeed, guide-induced RNA pseudouridylation suppressed NMD and upregulated the intact mRNA level 37-fold (0.00437 in lane 2; 0.1617 in lane 4, normalized by 5S control). It is therefore concluded that the guide RNA (from the pugIntronOpt-IDUA plasmid) is capable of giving read-through, thereby suppressing NMD, and that pseudouridylation has occurred. Similar results were obtained after 20 to 23 PCR cycles were performed, and when using a plasmid carrying a CFTR-G542X mutation as the substrate and using pugIntCFTR as the guide RNA expressing delivery vector, see FIG. 19. Here, the following primers were used: NBDIPSU-202Fwd: 5'-CTGGAGCCTTCAGAGG-3' (SEQ ID NO:35) and NBD1PSU+40(491-509)Rev: 5'-GCTCTTGCTAAAGAAATTC-3' (SEQ ID NO:36).

Detection of Full-Length Protein by Western-Blot

The same transfected HEK293T cells that were used for RNA extraction and subsequent RT-PCR (given above) to determine NMD suppression, were used to generate whole cell lysates. These were prepared in 500 μL NET2 buffer (50 mM Tris-HCl, pH 7.5, 150 mM NaCl, 0.05% Nonidet™ P40) supplemented with 0.02% SUS. Cell lysates were applied to sonication (at level 2 for 10 sec) followed by centrifugation (17,000×g for 20 min at 4° C.) to remove cell debris. The supernatant was used as total protein and subjected to protein analysis. Ectopically expressed FLAG-tagged protein was immunoprecipitated from the total protein using Anti-DYKDDDDK Magnetic Agarose (Thermo Scientific). Pulled-down and immunoprecipitated proteins were separated on a 15% SDS-PAGE, immunoblotted, and antibodies were detected by SuperSignal West Femto Maximum Sensitivity Substrate (Thermo Scientific). The FLAG-tagged protein was detected with monoclonal ANTI-FLAG M2, Clone M2 (F1804, SIGMA) as primary antibody and Goat Anti-Mouse IgG (H&L) [HRP], pAb (A10093, Genscript) as secondary antibody. The tubulin housekeeping gene was detected for normalization purposes (primary antibody: Tubulin-beta, Rabbit Polyclonal Antibody #RB-9249-P0 (Thermo Scientific); secondary antibody: Anti-rabbit IgG, HRP-linked Antibody #7074S (Cell Signaling)).

Results are shown in FIG. 16. The position of the full length protein FLAG-GL39-IDUA swap is given by an arrow. Lane 1 represents HEK293T cells that were only transfected with the substrate FLAG-GL39-IDUA swap plasmid. Lane 2 represents HEK293T cells transfected with the substrate FLAG-GL39-IDUA swap plasmid+the pugIntronOpt-IDUA plasmid as the guide RNA providing vector. Clearly, there is a significant increase in FLAG-GL39-IDUA abundance, which indicates that pseudouridylation has taken place in the UAG stop codon present in the RNA transcribed from the substrate plasmid and read-through during translation has taken place. This shows that the inventors of the present invention were able to pseudoridylate a target sequence in cells, in vivo, using endogenous (naturally present) RNA editing (pseudouridylation) enzymes, and after providing such cells with a guide RNA that was derived from its natural environment: an intronic sequence.

Detection of Pseudouridylation

To confirm that the NMD suppression (as detected through RT-PCR, see above and FIG. 15) and the appearance of the full length FLAG-tagged protein (as detected by western blot, see above and FIG. 16) were the result of real pseudouridylation obtained by using a target plasmid containing a premature termination codon and a intronic-carried guide RNA for pseudouridylation, a CMC-modified primer extension method was used that was earlier described by Adachi et al. (2019, Methods Mol Biol 1870:219-235). This multi-step method is based on pseudouridine-specific acylation using a reagent that preferentially modifies the pseudouridine bases, CMC (or CMCT: N-Cyclohexyl-N'-(2-morpholinoethyl) carbodiimide methyl-p-toluene-sulfonate). Although bases such as uridine, inosine and guanosine residues are initially also derivatized, it is possible to detect pseudouridines since only these will remain acetylated, while the remaining derivatized bases are hydrolyzed back to their natural chemical form after a mild alkaline treatment step. The way to map the position of the pseudouridines is through a primer extension reaction, where the bulkiness of the CMC at the pseudouridine residue can block the reverse transcription, generating a stop for the primer extension one nucleotide before the CMC-pseudouridine sites. Because natural RT-stops also occur as artifacts generated by strong secondary structures, a negative control (without CMC derivatization) is run in parallel to identify these. This reagent was used to map the position of all known pseudouridine residues in the transcriptome of human cells (Carlile et al, 2014. Nature 515 (7525):143-146). For this, HEK293T cells were transfected with substrate FLAG-GL39-IDUA swap plasmid together with either pugIntron-IDUA plasmid or with pug-CFTR which served as a negative control, as the CFTR specific guide RNA should not be able to pseudouridylate the IDUA target U in the stop codon. Total RNA was extracted as described above. 20 µg total RNA was used for CMC treatment followed by primer extension with a globin specific primer: hG1193-209AS: 5'-CCGAGCACTTTCTTGCC-3' (SEQ ID NO:25). 10 µg total RNA was used for primer extension of U6 snRNA control with a U6 specific primer: hU6-86-105AS: 5'-AATATGGAACGCTTCACGAA-3' (SEQ ID NO:26). The results are given in FIG. 17. The arrow indicates the position of the product where primer extension had stopped because of the presence of a ψ-CMC residue. This only occurred in the cells that were treated with CMC and transfected with the GL39-IDUA swap substrate plasmid and the pugIntron-IDUA guide RNA expressing plasmid (zoomed in panel). No bands could be detected in the samples from cells transfected with GL-IDUA swap with the negative control guide RNA expressing pug-CFTR plasmid. The position of the residue in relation to the primer used for primer extension is exactly known (92 bases). These results clearly demonstrate that pseudouridylation has taken place in HEK293T cells that were transfected with a target plasmid carrying a premature stop codon in an IDUA context and that were co-transfected with a plasmid carrying—in an intron—a snoRNA that is, once spliced out from the intron sequence, able to target the substrate sequence and to specifically pseudouridylate the U in the UAG stop codon.

Example 5: Increase in mRNA Levels Upon Treatment With Intron-Imbedded Guide RNAs and psEONs Further to what has been shown in Example 4, it was then tested whether a psEON, as outlined in detail herein, could also yield pseudouridylation using the substrate GL-IDUA swap plasmids after transfection in cells. For this, HEK293T cells were transfected at 90-100% confluency, using PEI in a 6-well dish, with 500 ng GL-IDUA swap substrate plasmid and 2.5 µg the pugIntron-IDUA guide RNA expressing plasmid or transfected with 100 pmol Cy3-IDUA-A psEON oligonucleotide. Four days after transfection cells were washed and incubated at for 24 h. Total RNA was isolated as described and RT-PCR was performed as outlined above, except that 21 cycles were performed for all samples. RT-PCR products were separated by gel electrophoresis. Results are shown in FIG. 18. These indicate that when no DNA was transfected (meaning no plasmid or psEON, on top of the transfected substrate plasmid) that no GL39 RT-PCR product was detectable, although the 5S control was abundant. However, after co-transfection of the pugIntron-IDUA guide RNA-expressing plasmid and also after co-transfection with the Cy3-iDUA-A psEON, the product was detectable, indicating that read-through of the mRNA occurred, and that NMD was inhibited. This shows that the inventors of the present invention were able to obtain pseudouridylation not only by using intronically-embedded guide RNAs, but also with the short psEONs of the present invention.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:

1. A nucleic acid molecule comprising a guide region consisting of a single hairpin structure corresponding to one of the two hairpin structures of the wild type H/ACA snoRNA, wherein
   (i) the nucleic acid molecule is capable of forming a partially double stranded nucleic acid complex with a target RNA in a mammalian cell, wherein the target RNA comprises a target uridine;
   (ii) the partially double stranded nucleic acid complex is capable of engaging a mammalian pseudouridylation enzyme;
   (iii) the guide region assists in positioning the target uridine in the partially double stranded nucleic acid complex; and
   (iv) the target uridine can be converted to a pseudouridine by the mammalian pseudouridylation enzyme.

2. The nucleic acid molecule according to claim 1, wherein the pseudouridylation enzyme is part of a ribonucleoprotein (RNP) complex capable of acting on an H/ACA-snoRNA.

3. The nucleic acid molecule according to claim 1, wherein the nucleic acid molecule comprises one or more nucleosides and/or inter-nucleosidic linkages that are non-naturally modified compared to the wild type H/ACA snoRNA.

4. The nucleic acid molecule according to claim 3, wherein the single hairpin structure is the hairpin structure at the 3' terminal part of the wild type H/ACA snoRNA.

5. The nucleic acid molecule according to claim 3, consisting of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

6. The nucleic acid molecule according to claim 3, wherein the non-natural modification comprises a modification in the ribose moiety.

7. The nucleic acid molecule according to claim 6, wherein the modification is substitution of the 2' OH of the sugar moiety for 2'-OMe or 2'-MOE.

8. The nucleic acid molecule according to claim 3, wherein the nucleic acid molecule comprises one or more non-natural inter-nucleosidic linkages.

9. The nucleic acid molecule according to claim 1, wherein the nucleic acid molecule is positioned in an intron sequence from which it is expressed, and wherein the intron sequence is located between an upstream exon sequence and a downstream exon sequence, wherein the upstream exon sequence comprises exon 1 of the human ß-globin gene, and the downstream exon sequence comprises exon 2 of the human ß-globin gene.

10. The nucleic acid molecule according to claim 9, wherein the upstream exon sequence/intron/downstream exon sequence is present in a vector.

11. The nucleic acid molecule according to claim 9, wherein the upstream exon sequence is exon 1 of the human ß-globin gene, and the downstream exon sequence is exon 2 of the human ß-globin gene.

12. The nucleic acid molecule according to claim 1, wherein the nucleic acid molecule is present in a vector comprising a CMV or a pol III promoter.

13. The nucleic acid molecule according to claim 1, wherein the guide region is capable of forming a partially double stranded complex with the target RNA, which comprises a mutation that is associated with a genetic disorder.

14. The nucleic acid molecule according to claim 13, wherein the mutation results in a Premature Termination Codon (PTC) and wherein the target uridine is in the PTC.

15. A method for converting a uridine in a target RNA molecule into a pseudouridine, comprising the steps of contacting a target RNA comprising a target uridine with the nucleic acid molecule according to claim 1 in the presence of a pseudouridylation enzyme or RNP complex and allowing the uridine to be converted thereby.

16. The method according to claim 15, wherein the pseudouridylation enzyme or RNP complex is present in a mammalian cell.

17. A vector comprising an intron sequence that is located between an upstream exon sequence and a downstream exon sequence, wherein the upstream exon sequence and the downstream exon sequence are of a gene that is not the natural gene for the intron sequence, and wherein the intron sequence comprises a nucleic acid molecule of claim 1.

18. The vector according to claim 17, wherein the upstream exon sequence is exon 1 of the human β-globin gene, and the downstream exon sequence is exon 2 of the human β-globin gene.

19. The vector according to claim 17, wherein the vector is a plasmid or a viral vector.

20. A pharmaceutical composition comprising a nucleic acid molecule according to claim 1 and one or more of a pharmaceutically acceptable carrier, stabilizer or solvent.

21. A method for converting a uridine in a target RNA molecule into a pseudouridine in a cell comprising administering to the cell a vector according to claim 17.

22. A mammalian cell comprising the nucleic acid molecule according to claim 1.

23. The method of claim 21, wherein the cell is a human cell.

24. The vector according to claim 17, wherein the upstream exon sequence comprises exon 1 of the human β-globin gene, and the downstream exon sequence comprises exon 2 of the human β-globin gene.

* * * * *

```
                        SEQUENCE LISTING

<160> NUMBER OF SEQ ID NOS: 40

<210> SEQ ID NO 1
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="RNA target substrate"

<400> SEQUENCE: 1 agggggaaccc cacagucgaa ccaaaacaaa                               30

<210> SEQ ID NO 2
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="RNA target substrate"

<400> SEQUENCE: 2
gacaauauag uucuuugaga agguggaauc                                30

<210> SEQ ID NO 3
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="RNA target substrate"

<400> SEQUENCE: 3
gauggagaac aacucuaggc agaggucuca                                30

<210> SEQ ID NO 4
<211> LENGTH: 61
<212> TYPE: RNA
<213> ORGANISM: Homo sapiens

<400> SEQUENCE: 4
ggguccgccu ugagugcccg ggugagaagc augaucccgg guaauuaugg cggacccaca  60
g                                                                 61

<210> SEQ ID NO 5
<211> LENGTH: 128
<212> TYPE: RNA
<213> ORGANISM: Homo sapiens

<400> SEQUENCE: 5
gugcacauuu cauugaccug cuuucuuuua ugugaguagu guuauuucuu augugcuaua  60
```

```
caaauaauug aaggcuaauu agcaguauaa cuauaaauag uaaugcugcc uguguccuuc    120
agacaaaa                                                            128

<210> SEQ ID NO 6
<211> LENGTH: 28
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Substrate RNA"

<400> SEQUENCE: 6
aaagugaaga aauucaauga agcgcggg                                       28

<210> SEQ ID NO 7
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Substrate RNA"

<400> SEQUENCE: 7
gaauccgacu guuuaauuaa aaca                                           24

<210> SEQ ID NO 8
<211> LENGTH: 65
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="psEON"

<400> SEQUENCE: 8
ggaauugaag gcugguucgc aguauaacua uaaauaguaa ugcugccugu guccuucaga    60
caaaa                                                                65

<210> SEQ ID NO 9
<211> LENGTH: 65
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="psEON"

<400> SEQUENCE: 9
ggaauugaag gcccuucugc aguauaacua uaaauaguaa ugcugcaaga acccuucaga    60
caaaa                                                                65

<210> SEQ ID NO 10
```

```
<211> LENGTH: 66
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="psEON"

<400> SEQUENCE: 10
ggaauugaag gcucugccgc aguauaacua uaaauaguaa ugcugcgagu uguccuucag    60
acaaaa                                                               66

<210> SEQ ID NO 11
<211> LENGTH: 5462
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="pugIntron-mIDUA plasmid"
<220> FEATURE:
<221> NAME/KEY: CDS
<222> LOCATION: (893)..(985)
<220> FEATURE:
<221> NAME/KEY: CDS
<222> LOCATION: (1150)..(1371)

<400> SEQUENCE: 11
gcgcccaata cgcaaaccgc ctctccccgc gcgttggccg attcattaat gcagctggca    60
cgacaggttt cccgactgga aagcgggcag tgagcgcaac gcaattaatg tgagttagct   120
cactcattag gcaccccaca ctttatgctt ccggctcgta tgttgtgtgg aattgtgagc   180
ggataacaat ttcacacagg aaacagctat gaccatgatt acgccaagct cggatcctag   240
agatatactg agtcattagg gactttccaa tgggttttgc ccagtacata aggtcaatag   300
gggtgaatca acaggaaagt cccattggag ccaagtacac tgagtcaata gggactttcc   360
attgggtttt gcccagtaca aaaggtcaat agggggtgag tcaatgggtt tttcccatta   420
ttggcacgta cataaggtca ataggggtga gtcattgggt ttttccagcc aatttaatta   480
aaacgccatg tactttccca ccattgacgt caatgggcta ttgaaactaa tgcaacgtga   540
cctttaaacg gtactttccc atagctgatt aatgggaaag taccgttctc gagccaatac   600
acgtcaatgg gaagtgaaag ggcagccaaa acgtaacacc gccccggttt tccctggaa    660 attccatatt ggcacgcatt ctattggctg agctgcgttc tacgtgggta taagaggcgc   720
gaccagcgtc ggtaccgtcg cagtcttcgg tctgaccacc gtagaacgca gatcgaattg   780
atcccgcgca gacactgacc ttcagcgcct cggctccagc gccatggctt ccaaggctcg   840
agctcagtac atcaagagct tcgtggagcg cgtgctgaag aacgagcagt ac atg gtg   898
                                                          Met Val
                                                            1 cac ctg act cct gag gag aag tct gcc gtt act gcc ctg tgg ggc aag    946
His Leu Thr Pro Glu Glu Lys Ser Ala Val Thr Ala Leu Trp Gly Lys
      5                  10                  15 gtg aac gtg gat gaa gtt ggt ggt gag gcc ctg ggc agg taagtcgacg     995
Val Asn Val Asp Glu Val Gly Gly Glu Ala Leu Gly Arg
 20                  25                  30 tgggagattc tgcctcggac agagagaaac tctgctgtgt ctgagagttg atctccctat  1055
```

```
agtgaccctg ccttcttgcc ccgggacgaa atgagagaaa tcgtaacggg agtttacgag      1115
gcagacaggt tgactctctc ttttcccctg cagg ctg ctg gtg gtc tac cct tgg      1170
                                      Leu Leu Val Val Tyr Pro Trp
                                                       35 acc cag agg ttc ttt gag tcc ttt ggg gat ctg tcc act cct gat gct        1218
Thr Gln Arg Phe Phe Glu Ser Phe Gly Asp Leu Ser Thr Pro Asp Ala
         40                  45                  50 gtt atg ggc aac cct aag gtg aag gct cat ggc aag aaa gtg ctc ggt        1266
Val Met Gly Asn Pro Lys Val Lys Ala His Gly Lys Lys Val Leu Gly
 55                  60                  65                  70 gcc ttt agt gat ggc ctg gct cac ctg gac aac ctc aag ggc acc ttt        1314
Ala Phe Ser Asp Gly Leu Ala His Leu Asp Asn Leu Lys Gly Thr Phe
                 75                  80                  85 gcc aca ctg agt gag ctg cac tgt gac aag ctg cac gtg gat cct gag        1362
Ala Thr Leu Ser Glu Leu His Cys Asp Lys Leu His Val Asp Pro Glu
             90                  95                 100 aac ttc agg gtgagtctga tgggcacctc ctgggtttcc ttcccctggc                1411
Asn Phe Arg
        105 tattctgctc aaccttccta tcagaaaaaa aggggaagcg attctaggga gcagtctcca      1471 tgactgtgtg tggagtgttg acaagagttc ggatatttta ttctctactc agaattgctg      1531 ctcccccctca ctctgttctg tgttgtcatt tcctctttct ttggtaagct tttaatttcc     1591 agttgcattt tactaaatta attaagctgg ttatttactt cccatcctga tatcagcttc      1651 ccctcctcct ttcctcccag tccttctctc tcctctctct cttctctaa tcctttcctt      1711 tccctcagtt catttcttct tctttgatct acgtttgttt gtctttttaa atattgcctt     1771 gtaacttgct cagaggacaa ggaagatatg tccctgtttc ttctcatagc tctcaagaat     1831 agtagcataa ttggcttta tgccagggtg acaggggaag aatatatttt acatataaat      1891 tctgtttgac ataggattct tataataatt tgtcagtagt ttaaggttgc aaacaaatgt      1951 cttttgtaaat aagcctgcag tatctggtat ttttgctcta cagttatgtt gatggttctt    2011 ccatattccc acagctcctg ggcaatatga tcgtgattgt gctgggccac cacctgggca     2071 aggatttcac ccccgctgca caggctgcct tccagaaggt ggtggctgga gtggccactg     2131 ccctggctca caagtaccac taaaccccct ttcctgctct tgcctgtgaa caatggttaa     2191 ttgttcccaa gagagcatct gtcagttgtt ggcaaaatga tagacatttg aaaatctgtc     2251 ttctgacaaa taaaaagcat ttatgttcac tgcaatgatg ttttaaatta tttgtctgtg    2311 tcatagaagg gtttatgcta agttttcaag atacaaagaa gtgaggggttc aggtctgacc   2371 ttggggaaat aaatgaatta cacttcaaat gtgtgggaca gcaagcagta agccacagat    2431 cctattgcca tgccctaaac actcagagaa aaattcaaca aatggtttca tttacacact     2491 acattatgat tacatttat gtaaattatt tgttttttttc tactcttcca cataaatgtc    2551 ttttttttcct cttacctacc cagcacttca cagttctcaa gccaataatt tttcttttgt    2611 aaaactacca ttattctcta aactttttccc tctgtgttta ccaagcaaca ttatttatct   2671 tttcataaat cctgttgcct tagacagctt cagtagcaat agaggtagga ttaaggagag     2731 aatagaagtg ccctgtttgt cataccatgc ctgcacagtc aatagtcact atgggatttc     2791 aaatggcact ttgcctggga cctttacact tcacaccata ctctggcttg agttaggagt    2851 taagaatgag agaaatataa gtctagagag aataagaata tctagttttt aaggctcatt     2911 actggggtct tatgaaattt ccataatacc ctgtaaatgg aagcatttat tttttcaata    2971
```

```
aatctatctt gaatatccag tgtgggttag gattaaatct ctccttcata cagttggact   3031
gcttttattt atatggagtt actagagtta attcactggc cgtcgtttta caacgtcgtg   3091
actgggaaaa ccctggcgtt acccaactta atcgccttgc agcacatccc cctttcgcca   3151
gctggcgtaa tagcgaagag gcccgcaccg atcgcccttc ccaacagttg cgcagcctga   3211
atggcgaatg gcgcctgatg cggtattttc tccttacgca tctgtgcggt atttcacacc   3271
gcatatggtg cactctcagt acaatctgct ctgatgccgc atagttaagc cagccccgac   3331
acccgccaac acccgctgac gcgccctgac gggcttgtct gctcccggca tccgcttaca   3391
gacaagctgt gaccgtctcc gggagctgca tgtgtcagag gttttcaccg tcatcaccga   3451
aacgcgcgag acgaaagggc ctcgtgatac gcctattttt ataggttaat gtcatgataa   3511
taatggtttc ttagacgtca ggtggcactt ttcggggaaa tgtgcgcgga acccctattt   3571
gtttattttt ctaaatacat tcaaatatgt atccgctcat gagacaataa ccctgataaa   3631
tgcttcaata atattgaaaa aggaagagta tgagtattca acatttccgt gtcgccctta   3691
ttcccttttt tgcggcattt tgccttcctg tttttgctca cccagaaacg ctggtgaaag   3751
taaaagatgc tgaagatcag ttgggtgcac gagtgggtta catcgaactg gatctcaaca   3811
gcggtaagat ccttgagagt tttcgccccg aagaacgttt tccaatgatg agcactttta   3871
aagttctgct atgtggcgcg gtattatccc gtattgacgc cgggcaagag caactcggtc   3931
gccgcataca ctattctcag aatgacttgg ttgagtactc accagtcaca gaaaagcatc   3991
ttacggatgg catgacagta agagaattat gcagtgctgc cataaccatg agtgataaca   4051
ctgcggccaa cttacttctg acaacgatcg gaggaccgaa ggagctaacc gcttttttgc   4111
acaacatggg ggatcatgta actcgccttg atcgttggga accggagctg aatgaagcca   4171
taccaaacga cgagcgtgac accacgatgc ctgtagcaat ggcaacaacg ttgcgcaaac   4231
tattaactgg cgaactactt actctagctt cccggcaaca attaatagac tggatggagg   4291
cggataaagt tgcaggacca cttctgcgct cggcccttcc ggctggctgg tttattgctg   4351
ataaatctgg agccggtgag cgtgggtctc gcggtatcat tgcagcactg gggccagatg   4411
gtaagccctc ccgtatcgta gttatctaca cgacggggag tcaggcaact atggatgaac   4471
gaaatagaca gatcgctgag ataggtgcct cactgattaa gcattggtaa ctgtcagacc   4531
aagtttactc atatatactt tagattgatt taaaacttca ttttttaattt aaaaggatct   4591
aggtgaagat cctttttgat aatctcatga ccaaaatccc ttaacgtgag ttttcgttcc   4651
actgagcgtc agacccgta gaaaagatca aaggatcttc ttgagatcct ttttttctgc   4711
gcgtaatctg ctgcttgcaa acaaaaaaac caccgctacc agcggtggtt tgtttgccgg   4771
atcaagagct accaactctt tttccgaagg taactggctt cagcagagcg cagataccaa   4831
atactgtcct tctagtgtag ccgtagttag gccaccactt caagaactct gtagcaccgc   4891
ctacatacct cgctctgcta atcctgttac cagtggctgc tgccagtggc gataagtcgt   4951
gtcttaccgg gttggactca agacgatagt taccggataa ggcgcagcgg tcgggctgaa   5011
cggggggttc gtgcacacag cccagcttgg agcgaacgac ctacaccgaa ctgagatacc   5071
tacagcgtga gctatgagaa agcgccacgc ttcccgaagg gagaaaggcg gacaggtatc   5131
cggtaagcgg cagggtcgga acaggagagc gcacgaggga gcttccaggg ggaaacgcct   5191
ggtatcttta tagtcctgtc gggtttcgcc acctctgact tgagcgtcga ttttttgtgat  5251
gctcgtcagg gggcggagc ctatggaaaa acgccagcaa cgcggccttt ttacggttcc    5311
tggccttttg ctggcctttt gctcacatgt tctttcctgc gttatcccct gattctgtgg   5371
```

| | |
|---|---|
| ataaccgtat taccgccttt gagtgagctg ataccgctcg ccgcagccga acgaccgagc | 5431 |
| gcagcgagtc agtgagcgag gaagcggaag a | 5462 |

<210> SEQ ID NO 12
<211> LENGTH: 4974
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="pFLAG-Globin39ter plasmid"

<400> SEQUENCE: 12

| | |
|---|---|
| ccattcgcca ttcaggctgc gcaactgttg ggaagggcga tcggtgcggg cctcttcgct | 60 |
| attacgccag ctggcgaaag ggggatgtgc tgcaaggcga ttaagttggg taacgccagg | 120 |
| gttttcccag tcacgacgtt gtaaaacgac ggccagtgcc aagctgatct atacattgaa | 180 |
| tcaatattgg caattagcca tattagtcat tggttatata gcataaatca atattggcta | 240 |
| ttggccattg catacgttgt atctatatca taatatgtac atttatattg gctcatgtcc | 300 |
| aatatgaccg ccatgttgac attgattatt gactagttat taatagtaat caattacggg | 360 |
| gtcattagtt catagcccat atatggagtt ccgcgttaca taacttacgg taaatggccc | 420 |
| gcctggctga ccgcccaacg acccccgccc attgacgtca ataatgacgt atgttcccat | 480 |
| agtaacgcca atagggactt tccattgacg tcaatgggtg gagtatttac ggtaaactgc | 540 |
| ccacttggca gtacatcaag tgtatcatat gccaagtccg cccctattg acgtcaatga | 600 |
| cggtaaatgg cccgcctggc attatgccca gtacatgacc ttacgggact ttcctacttg | 660 |
| gcagtacatc tacgtattag tcatcgctat taccatggtg atgcggtttt ggcagtacac | 720 |
| caatgggcgt ggatagcggt ttgactcacg gggatttcca agtctccacc ccattgacgt | 780 |
| caatgggagt ttgttttggc accaaaatca acgggacttt ccaaaatgtc gtaataaccc | 840 |
| cgccccgttg acgcaaatgg gcggtaggcg tgtacggtgg gaggtctata taagcagagc | 900 |
| tcgtttagtg aaccgtcaga attgatctac catggactac aaagacgatg acgacaagct | 960 |
| tatggactac aaggacgacg atgacaagca tatggtgcac ctgactcctg aggagaagtc | 1020 |
| tgccgttact gccctgtggg gcaaggtgaa cgtggatgaa gttggtggtg aggccctggg | 1080 |
| caggttggta tcaaggttac aagacaggtt taaggagacc aatagaaact gggcatgtgg | 1140 |
| agacagagaa gactcttggg tttctgatag gcactgactc tctctgccta ttggtctatt | 1200 |
| ttcccaccct taggctgctg gtggatgag aacaactcta gcagaggtc tcaaaatttg | 1260 |
| gggatctgtc cactcctgat gctgttatgg gcaaccctaa ggtgaaggct catggcaaga | 1320 |
| aagtgctcgg tgcctttagt gatggcctgg ctcacctgga caacctcaag ggcacctttg | 1380 |
| ccacactgag tgagctgcac tgtgacaagc tgcacgtgga tcctgagaac ttcagggtga | 1440 |
| gtctatggga cccttgatgt tttctttccc cttcttttct atggttaagt tcatgtcata | 1500 |
| ggaaggggat aagtaacagg gtacagttta gaatgggaaa cagacgaatg attgcatcag | 1560 |
| tgtggaagtc tcaggatcgt tttagtttct tttatttgct gttcataaca attgttttct | 1620 |
| tttgtttaat tcttgctttc ttttttttc ttctccgcaa ttttactat tatacttaat | 1680 |
| gccttaacat tgtgtataac aaaaggaaat atctctgaga tacattaagt aacttaaaaa | 1740 |
| aaaactttac acagtctgcc tagtacatta ctatttggaa tatatgtgtg cttatttgca | 1800 |

```
tattcataat ctccctactt tattttcttt tattttaat tgatacataa tcattataca    1860
tatttatggg ttaaagtgta atgttttaat atgtgtacac atattgacca aatcagggta   1920
attttgcatt tgtaatttta aaaaatgctt tcttcttta atatacttt ttgtttatct    1980 tatttctaat actttcccta atctctttct ttcagggcaa taatgataca atgtatcatg  2040
cctctttgca ccattctaaa gaataacagt gataatttct gggttaaggc aatagcaata  2100
tctctgcata taaatatttc tgcatataaa ttgtaactga tgtaagaggt ttcatattgc  2160
taatagcagc tacaatccag ctaccattct gcttttattt tatggttggg ataaggctgg  2220
attattctga gtccaagcta ggccctttg ctaatcatgt tcatacctct tatcttcctc   2280
ccacagctcc tgggcaacgt gctggtctgt gtgctggccc atcactttgg caaagaattc  2340
accccaccag tgcaggctgc ctatcagaaa gtggtggctg gtgtggctaa tgccctggcc  2400
cacaagtatc actaagctcg ctttcttgct gtccaatttc tattaaaggt tcctttgttc  2460
cctaagtcca actactaaac tgggggatat tatgaagggc cttgagcatc tggattctgc  2520
ctaataaaaa acatttattt tcattgcaat gatgtattta aattatttct gaatatttta  2580
ctaaaagggg aatgtgggag gtcagtctag aggatcccgg gtggcatccc tgtgaccct   2640 ccccagtgcc tctcctggcc ctggaagttg ccactccagt gcccaccagc cttgtcctaa  2700
taaaattaag ttgcatcatt ttgtctgact aggtgtcctt ctataatatt atggggtgga  2760 gggggggtggt atggagcaag gggcaagttg ggaagacaac ctgtagggcc tgcgggtct   2820 attgggaacc aagctggagt gcagtggcac aatcttggct cactgcaatc tccgcctcct  2880
gggttcaagc gattctcctg cctcagcctc ccgagttgtt gggattccag gcatgcatga  2940
ccaggctcag ctaatttttg ttttttggt agagacgggg tttcaccata ttggccaggc   3000
tggtctccaa ctcctaatct caggtgatct acccaccttg gcctcccaaa ttgctgggat  3060
tacaggcgtg aaccactgct cccttccctg tccttctgat tttaaaataa ctataccagc  3120
aggaggacgt ccagacacag cataggctac ctggccatgc ccaaccggtg ggacatttga  3180
gttgcttgct tggcactgtc ctctcatgcg ttgggtccac tcagtagatg cctgttgaat  3240
tgggtacgcg gccagcttgg ctgtggaatg tgtgtcagtt agggtgtgga aagtccccag  3300 gctcccagc aggcagaagt atgcaaagca tgcatctcaa ttagtcagca accaggtgtg   3360
gaaagtcccc aggctcccca gcaggcagaa gtatgcaaag catgcatctc aattagtcag  3420
caaccatagt cccgcccta actccgccca tcccgcccct aactccgccc agttccgccc   3480
attctccgcc ccatggctga ctaattttt tatttatgc agaggccgag gccgcctcgg   3540
cctctgagct attccagaag tagtgaggag gcttttttgg aggcctaggc ttttgcaaaa  3600
agctcctcga ggaactgaaa aaccagaaag ttaattccct atagtgagtc gtattaaatt  3660
cgtaatcatg tcatagctgt ttcctgtgtg aaattgttat ccgctcacaa ttccacacaa  3720
catacgagcc ggaagcataa agtgtaaagc ctggggtgcc taatgagtga gctaactcac  3780
attaattgcg ttgcgctcac tgcccgcttt ccagtcggga aacctgtcgt gccagctgca  3840
ttaatgaatc ggccaacgcg cggggagagg cggtttgcgt attgggcgct cttccgcttc  3900
ctcgctcact gactcgctgc gctcggtcgt tcggctgcgg cgagcggtat cagctcactc  3960
aaaggcggta atacggttat ccacagaatc aggggataac gcaggaaaga acatgtgagc  4020
aaaaggccag caaaaggcca ggaaccgtaa aaaggccgcg ttgctggcgt ttttccatag  4080
gctccgcccc cctgacgagc atcacaaaaa tcgacgctca agtcagaggt ggcgaaaccc  4140
```

```
gacaggacta taaagatacc aggcgtttcc ccctggaagc tccctcgtgc gctctcctgt    4200
tccgaccctg ccgcttaccg gatacctgtc cgcctttctc ccttcgggaa gcgtggcgct    4260
ttctcatagc tcacgctgta ggtatctcag ttcggtgtag gtcgttcgct ccaagctggg    4320
ctgtgtgcac gaaccccccg ttcagcccga ccgctgcgcc ttatccggta actatcgtct    4380
tgagtccaac ccggtaagac acgacttatc gccactggca gcagccactg gtaacaggat    4440
tagcagagcg aggtatgtag gcggtgctac agagttcttg aagtggtggc ctaactacgg    4500
ctacactaga agaacagtat ttggtatctg cgctctgctg aagccagtta ccttcggaaa    4560
aagagttggt agctcttgat ccggcaaaca accaccgct ggtagcggtg ttttttttgt    4620
ttgcaagcag cagattacgc gcagaaaaaa aggatctcaa gaagatcctt tgatcttttc    4680
tacggggtct gacgctcagt ggaacgaaaa ctcacgttaa gggattttgg tcatgagatt    4740
atcaaaaagg atcttcacct agatcctttt aaattaaaaa tgaagtttta aatcaatcta    4800
aagtatatat gagtaaactt ggtctgacag ttaccaatgc ttaatcagtg aggcaccctat   4860 ctcagcgatc tgtctatttc gttcatccat agttgcctga ctccccgtcg tgtagataac    4920
tacgatacgg gagggcttac catctggccc cagtgctgca atgataccgc gaga          4974

<210> SEQ ID NO 13
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="SDM1-GLintron1-Sal-Pst"

<400> SEQUENCE: 13
gtaagtcgac gaattctgca ggctgctggt gg                                    32

<210> SEQ ID NO 14
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="SDM2-GLintron-Sal-Pst"

<400> SEQUENCE: 14
gcctgcagaa ttcgtcgact tacctgccca gg                                    32

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-intron-FwdSalI"

<400> SEQUENCE: 15
gttgtcgacg tgggagattc t                                                21
```

```
<210> SEQ ID NO 16
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-intron-RevExPstI"

<400> SEQUENCE: 16
aatctgcagg ggaaaagaga gagtcaacct gtctgcctcg t                    41

<210> SEQ ID NO 17
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="SDM-GL39-SWAPto-mmidua-1"

<400> SEQUENCE: 17
tggtggatgg agaacaactc taggcagagg tctcaaagtt tggggatctg tccactcc   58

<210> SEQ ID NO 18
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="SDM-GL39-SWAPto-mmidua-2"

<400> SEQUENCE: 18
ccaaactttg agacctctgc ctagagttgt tctccatcca ccagcagcct aagggtgg   58

<210> SEQ ID NO 19
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="RLuc-Gl ex1 S4"

<400> SEQUENCE: 19
tctgccgtta ctgccctgtg                                            20

<210> SEQ ID NO 20
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

<223> OTHER INFORMATION: /note="PE-mmiduaPTC+16"

<400> SEQUENCE: 20
ctttgagacc tctgcc                                                          16

<210> SEQ ID NO 21
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-intronOPT-RevExPstI"

<400> SEQUENCE: 21
aatctgcagg ggaaaagaga gagtcagtac ctgtctgcct c                               41

<210> SEQ ID NO 22
<211> LENGTH: 5464
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="pugIntronOpt-IDUA"
<220> FEATURE:
<221> NAME/KEY: CDS
<222> LOCATION: (893)..(985)
<220> FEATURE:
<221> NAME/KEY: CDS
<222> LOCATION: (1152)..(1373)

<400> SEQUENCE: 22
gcgcccaata cgcaaaccgc ctctccccgc gcgttggccg attcattaat gcagctggca           60
cgacaggttt cccgactgga aagcgggcag tgagcgcaac gcaattaatg tgagttagct          120
cactcattag gcaccccaca ctttatgctt ccggctcgta tgttgtgtgg aattgtgagc          180
ggataacaat ttcacacagg aaacagctat gaccatgatt acgccaagct cggatcctag          240
agatatactg agtcattagg gactttccaa tgggttttgc ccagtacata aggtcaatag          300
gggtgaatca acaggaaagt cccattggag ccaagtacac tgagtcaata gggactttcc          360
attgggtttt gcccagtaca aaaggtcaat aggggggtgag tcaatgggtt tttcccatta          420
ttggcacgta cataaggtca ataggggtga gtcattgggt ttttccagcc aatttaatta          480
aaacgccatg tactttccca ccattgacgt caatgggcta ttgaaactaa tgcaacgtga          540
ccttaaaacg gtactttccc atagctgatt aatgggaaag taccgttctc gagccaatac          600
acgtcaatgg gaagtgaaag gcagccaaa acgtaacacc gccccggttt tcccctggaa           660
attccatatt ggcacgcatt ctattggctg agctgcgttc tacgtgggta taagaggcgc          720
gaccagcgtc ggtaccgtcg cagtcttcgg tctgaccacc gtagaacgca gatcgaattg          780
atcccgcgca gacactgacc ttcagcgcct cggctccagc gccatggctt ccaaggctcg          840
agctcagtac atcaagagct cgtggagcg cgtgctgaag aacgagcagt ac atg gtg          898
                                                        Met Val
                                                        1 cac ctg act cct gag gag aag tct gcc gtt act gcc ctg tgg ggc aag           946
His Leu Thr Pro Glu Glu Lys Ser Ala Val Thr Ala Leu Trp Gly Lys
  5                  10                  15

| | | |
|---|---|---|
| gtg aac gtg gat gaa gtt ggt ggt gag gcc ctg ggc agg taagtcgacg<br>Val Asn Val Asp Glu Val Gly Gly Glu Ala Leu Gly Arg<br>    20                      25                    30 | | 995 |
| tgggagattc tgcctcggac agagagaaac tctgctgtgt ctgagagttg atctccctat | | 1055 |
| agtgaccctg ccttcttgcc ccgggacgaa atgagagaaa tcgtaacggg agtttacgag | | 1115 |
| gcagacaggt actgactctc tcttttcccc tgcagg ctg ctg gtg gtc tac cct<br>                                                                             Leu Leu Val Val Tyr Pro<br>                                                                                   35 | | 1169 |
| tgg acc cag agg ttc ttt gag tcc ttt ggg gat ctg tcc act cct gat<br>Trp Thr Gln Arg Phe Phe Glu Ser Phe Gly Asp Leu Ser Thr Pro Asp<br>          40                          45                            50 | | 1217 |
| gct gtt atg ggc aac cct aag gtg aag gct cat ggc aag aaa gtg ctc<br>Ala Val Met Gly Asn Pro Lys Val Lys Ala His Gly Lys Lys Val Leu<br> 55                       60                            65 | | 1265 |
| ggt gcc ttt agt gat ggc ctg gct cac ctg gac aac ctc aag ggc acc<br>Gly Ala Phe Ser Asp Gly Leu Ala His Leu Asp Asn Leu Lys Gly Thr<br> 70                       75                            80                            85 | | 1313 |
| ttt gcc aca ctg agt gag ctg cac tgt gac aag ctg cac gtg gat cct<br>Phe Ala Thr Leu Ser Glu Leu His Cys Asp Lys Leu His Val Asp Pro<br>                        90                            95                              100 | | 1361 |
| gag aac ttc agg gtgagtctga tgggcacctc ctgggtttcc ttccctggc<br>Glu Asn Phe Arg<br>                 105 | | 1413 |
| tattctgctc aaccttccta tcagaaaaaa aggggaagcg attctaggga gcagtctcca | | 1473 |
| tgactgtgtg tggagtgttg acaagagttc ggatatttta ttctctactc agaattgctg | | 1533 |
| ctcccccctca ctctgttctg tgttgtcatt tcctctttct ttggtaagct tttaatttcc | | 1593 |
| agttgcattt tactaaatta attaagctgg ttatttactt cccatcctga tatcagcttc | | 1653 |
| ccctcctcct ttcctcccag tccttctctc tctcctctct cttctctaa tcctttcctt | | 1713 |
| tccctcagtt catttcttct tctttgatct acgtttgttt gtcttttaa atattgcctt | | 1773 |
| gtaacttgct cagaggacaa ggaagatatg tccctgtttc ttctcatagc tctcaagaat | | 1833 |
| agtagcataa ttggcttttta tgccagggtg acaggggaag aatatatttt acatataaat | | 1893 |
| tctgtttgac ataggattct tataataatt tgtcagtagt ttaaggttgc aaacaaatgt | | 1953 |
| ctttgtaaat aagcctgcag tatctggtat ttttgctcta cagttatgtt gatggttctt | | 2013 |
| ccatattccc acagctcctg gcaatatga tcgtgattgt gctgggccac cacctgggca | | 2073 |
| aggatttcac ccccgctgca caggctgcct tccagaaggt ggtggctgga gtggccactg | | 2133 |
| ccctggctca caagtaccac taaaccccct ttcctgctct tgcctgtgaa caatggttaa | | 2193 |
| ttgttcccaa gagagcatct gtcagttgtt ggcaaaatga tagacatttg aaaatctgtc | | 2253 |
| ttctgacaaa taaaaagcat ttatgttcac tgcaatgatg ttttaaatta tttgtctgtg | | 2313 |
| tcatagaagg gtttatgcta agttttcaag atacaaagaa gtgagggttc aggtctgacc | | 2373 |
| ttggggaaat aaatgaatta cacttcaaat gtgtgggaca gcaagcagta agccacagat | | 2433 |
| cctattgcca tgccctaaac actcagagaa aaattcaaca aatggtttca tttacacact | | 2493 |
| acattatgat tacattttat gtaaattatt tgttttttc tactcttcca cataaatgtc | | 2553 |
| ttttttttcct cttacctacc cagcacttca cagttctcaa gccaataatt tttcttttgt | | 2613 |
| aaaactacca ttattctcta aacttttccc tctgtgttta ccaagcaaca ttatttatct | | 2673 |
| tttcataaat cctgttgcct tagacagctt cagtagcaat agaggtagga ttaaggagag | | 2733 |
| aatagaagtg ccctgtttgt cataccatgc ctgcacagtc aatagtcact atgggatttc | | 2793 |

```
aaatggcact tgcctggga cctttacact tcacaccata ctctggcttg agttaggagt    2853
taagaatgag agaaatataa gtctagagag aataagaata tctagttttt aaggctcatt    2913
actggggtct tatgaaattt ccataatacc ctgtaaatgg aagcatttat ttttcaata    2973 aatctatctt gaatatccag tgtgggttag gattaaatct ctccttcata cagttggact    3033
gcttttattt atatggagtt actagagtta attcactggc cgtcgtttta caacgtcgtg    3093
actgggaaaa ccctggcgtt acccaactta atcgccttgc agcacatccc ctttcgcca    3153 gctggcgtaa tagcgaagag gcccgcaccg atcgccttc ccaacagttg cgcagcctga    3213
atggcgaatg gcgcctgatg cggtattttc tccttacgca tctgtgcggt atttcacacc    3273
gcatatggtg cactctcagt acaatctgct ctgatgccgc atagttaagc cagccccgac    3333
acccgccaac acccgctgac gcgccctgac gggcttgtct gctcccggca tccgcttaca    3393
gacaagctgt gaccgtctcc gggagctgca tgtgtcagag gttttcaccg tcatcaccga    3453
aacgcgcgag acgaaagggc ctcgtgatac gcctattttt ataggttaat gtcatgataa    3513
taatggtttc ttagacgtca ggtggcactt ttcggggaaa tgtgcgcgga acccctattt    3573
gtttattttt ctaaatacat tcaaatatgt atccgctcat gagacaataa ccctgataaa    3633
tgcttcaata atattgaaaa aggaagagta tgagtattca catttccgt gtcgccctta    3693 ttccctttt tgcggcattt tgccttcctg tttttgctca cccagaaacg ctggtgaaag    3753
taaaagatgc tgaagatcag ttgggtgcac gagtgggtta tcgaactg gatctcaaca    3813 gcggtaagat ccttgagagt tttcgccccg aagaacgttt tccaatgatg agcacttta    3873 aagttctgct atgtggcgcg gtattatccc gtattgacgc cgggcaagag caactcggtc    3933
gccgcataca ctattctcag aatgacttgg ttgagtactc accagtcaca gaaaagcatc    3993
ttacggatgg catgacagta agagaattat gcagtgctgc cataaccatg agtgataaca    4053
ctgcggccaa cttacttctg acaacgatcg gaggaccgaa ggagctaacc gcttttttgc    4113
acaacatggg ggatcatgta actcgccttg atcgttggga accggagctg aatgaagcca    4173
taccaaacga cgagcgtgac accacgatgc ctgtagcaat ggcaacaacg ttgcgcaaac    4233
tattaactgg cgaactactt actctagctt cccggcaaca attaatagac tggatggagg    4293
cggataaagt tgcaggacca cttctgcgct cggcccttcc ggctggctgg tttattgctg    4353
ataaatctgg agccggtgag cgtgggtctc gcggtatcat tgcagcactg gggccagatg    4413
gtaagccctc ccgtatcgta gttatctaca cgacggggag tcaggcaact atggatgaac    4473
gaaatagaca gatcgctgag ataggtgcct cactgattaa gcattggtaa ctgtcagacc    4533
aagtttactc atatatactt tagattgatt taaaacttca ttttaatt aaaaggatct    4593 aggtgaagat cctttttgat aatctcatga ccaaaatccc ttaacgtgag ttttcgttcc    4653
actgagcgtc agaccccgta gaaaagatca aaggatcttc ttgagatcct ttttttctgc    4713
gcgtaatctg ctgcttgcaa acaaaaaaac caccgctacc agcggtggtt tgtttgccgg    4773
atcaagagct accaactctt tttccgaagg taactggctt cagcagagcg cagataccaa    4833
atactgtcct tctagtgtag ccgtagttag gccaccactt caagaactct gtagcaccgc    4893
ctacatacct cgctctgcta atcctgttac cagtggctgc tgccagtggc gataagtcgt    4953
gtcttaccgg gttggactca agacgatagt taccggataa ggcgcagcgg tcgggctgaa    5013
cggggggttc gtgcacacag cccagcttgg agcgaacgac ctacaccgaa ctgagatacc    5073
tacagcgtga gctatgagaa agcgccacgc ttcccgaagg gagaaaggcg gacaggtatc    5133
cggtaagcgg cagggtcgga acaggagagc gcacgaggga gcttccaggg ggaaacgcct    5193
```

| | | |
|---|---|---|
| ggtatcttta tagtcctgtc gggtttcgcc acctctgact tgagcgtcga tttttgtgat | | 5253 |
| gctcgtcagg ggggcggagc ctatggaaaa acgccagcaa cgcggccttt ttacggttcc | | 5313 |
| tggccttttg ctggccttt gctcacatgt tctttcctgc gttatcccct gattctgtgg | | 5373 |
| ataaccgtat taccgccttt gagtgagctg ataccgctcg ccgcagccga acgaccgagc | | 5433 |
| gcagcgagtc agtgagcgag gaagcggaag a | | 5464 |

<210> SEQ ID NO 23
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5SFwd"

<400> SEQUENCE: 23
gccataccac cctgaacg                                                   18

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5SRev"

<400> SEQUENCE: 24
agcttccgag atcagacgag                                                 20

<210> SEQ ID NO 25
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="hGl193-209AS"

<400> SEQUENCE: 25
ccgagcactt tcttgcc                                                    17

<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="U6Rev"

<400> SEQUENCE: 26
aatatggaac gcttcacgaa                                                 20

<210> SEQ ID NO 27
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-NBD1-F1HindIII"

<400> SEQUENCE: 27
attaagcttg tgtgggagat tcttcttcgg acagagagaa actctgctgt g          51

<210> SEQ ID NO 28
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-NBD1-R1"

<400> SEQUENCE: 28
ctgctgtgtc tgaaagaaga tctccctata gtgaccctgc cttaccttct ccgggacgaa    60

<210> SEQ ID NO 29
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-NBD1-R2BamHI"

<400> SEQUENCE: 29
atggatccac ctgtctgcct cgtattcttc cgttacgatt tctctcattt cgtcccgg     58

<210> SEQ ID NO 30
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-mmidua-F1HindIII"

<400> SEQUENCE: 30
attaagcttg tgtgggagat tctgcctcgg acagagagaa actctgctgt g          51

<210> SEQ ID NO 31
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-mmidua-R1"

<400> SEQUENCE: 31
ttcgtcccgg ggcagagaag gcagggtcac tatagggaga tcaactctca gacacagcag    60

<210> SEQ ID NO 32
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="pug-mmidua-R2BamHI"

<400> SEQUENCE: 32
atggatccac ctgtctgcct cgtaaactcc cgttacgatt tctctcattt cgtcccgg     58

<210> SEQ ID NO 33
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="SDM-GL39-SWAPto-NBD1-1"

<400> SEQUENCE: 33
tggtggacaa tatagttctt tgagaaggtg gaatcacatt tggggatctg tccactcc     58

<210> SEQ ID NO 34
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="SDM-GL39-SWAPto-NBD1-2"

<400> SEQUENCE: 34
ccaaatgtga ttccaccttc tcaaagaact atattgtcca ccagcagcct aagggtgg     58

<210> SEQ ID NO 35
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="NBD1PSU-202Fwd"

<400> SEQUENCE: 35
ctggagcctt cagagg    16

<210> SEQ ID NO 36
<211> LENGTH: 19
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="NBD1PSU+40(491-509)Rev"

<400> SEQUENCE: 36
gctcttgcta aagaaattc                                                  19

<210> SEQ ID NO 37
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg
            20                  25                  30

<210> SEQ ID NO 38
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Leu Leu Val Val Tyr Pro Trp Thr Gln Arg Phe Phe Glu Ser Phe Gly
1               5                   10                  15

Asp Leu Ser Thr Pro Asp Ala Val Met Gly Asn Pro Lys Val Lys Ala
            20                  25                  30

His Gly Lys Lys Val Leu Gly Ala Phe Ser Asp Gly Leu Ala His Leu
        35                  40                  45

Asp Asn Leu Lys Gly Thr Phe Ala Thr Leu Ser Glu Leu His Cys Asp
    50                  55                  60

Lys Leu His Val Asp Pro Glu Asn Phe Arg
65                  70

<210> SEQ ID NO 39
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg
            20                  25                  30

<210> SEQ ID NO 40
<211> LENGTH: 74
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Leu Leu Val Val Tyr Pro Trp Thr Gln Arg Phe Phe Glu Ser Phe Gly
1               5                   10                  15

Asp Leu Ser Thr Pro Asp Ala Val Met Gly Asn Pro Lys Val Lys Ala
            20                  25                  30

His Gly Lys Lys Val Leu Gly Ala Phe Ser Asp Gly Leu Ala His Leu
        35                  40                  45

Asp Asn Leu Lys Gly Thr Phe Ala Thr Leu Ser Glu Leu His Cys Asp
    50                  55                  60

Lys Leu His Val Asp Pro Glu Asn Phe Arg
65                  70
```